(12) United States Patent
Brunetti et al.

(10) Patent No.: US 11,224,720 B2
(45) Date of Patent: Jan. 18, 2022

(54) INFUSION SYSTEMS, CONNECTORS FOR USE WITH CATHETER DEVICES, AND RELATED METHODS

(71) Applicants: B. Braun Melsungen AG, Melsungen (DE); B. Braun Medical Inc., Bethlehem, PA (US)

(72) Inventors: Bruce Brunetti, Phillipsburg, NJ (US); Scott Moyer, Green Lane, PA (US); Frank Starner, Nazareth, PA (US); Tom Sutton, Summit, NJ (US); Steve Weber, Northhampton, PA (US); Cheryl Wozniak, Sinking Spring, PA (US); Matthew Bellenoit, Northampton, PA (US); Kevin Woehr, Felsberg (DE); Helmut Freigang, Körle (DE)

(73) Assignees: B. Braun Melsungen AG, Melsungen (DE); B. Braun Medical Inc., Bethlehem, PA (US)

( * ) Notice: Subject to any disclaimer, the term of this patent is extended or adjusted under 35 U.S.C. 154(b) by 586 days.

(21) Appl. No.: 15/757,915

(22) PCT Filed: Sep. 9, 2016

(86) PCT No.: PCT/EP2016/071345
§ 371 (c)(1),
(2) Date: Mar. 6, 2018

(87) PCT Pub. No.: WO2017/042359
PCT Pub. Date: Mar. 16, 2017

(65) Prior Publication Data
US 2018/0339132 A1    Nov. 29, 2018

Related U.S. Application Data

(60) Provisional application No. 62/357,632, filed on Jul. 1, 2016, provisional application No. 62/216,273, filed on Sep. 9, 2015.

(51) Int. Cl.
*A61M 25/00* (2006.01)
*A61M 39/10* (2006.01)
(Continued)

(52) U.S. Cl.
CPC .......... *A61M 25/0097* (2013.01); *A61M 5/14* (2013.01); *A61M 25/02* (2013.01);
(Continued)

(58) Field of Classification Search
CPC .......... A61M 25/0097; A61M 25/0014; A61M 25/02; A61M 39/10; A61M 39/1011;
(Continued)

(56) References Cited

U.S. PATENT DOCUMENTS 3,378,006 A    4/1968  Burke
4,129,128 A    12/1978 McFarlane
(Continued)

FOREIGN PATENT DOCUMENTS

EP    2397180 A1    12/2011
JP    H04-506011 A   10/1992
(Continued)

OTHER PUBLICATIONS

International Search Report and Written Opinion on related PCT application (PCT/EP2016/071345) from International Searching Authority (EPO) dated Nov. 18, 2016.
(Continued)

*Primary Examiner* — Kevin C Sirmons
*Assistant Examiner* — Alexandra Lalonde
(74) *Attorney, Agent, or Firm* — Klein, O'Neil & Singh, LLP

(57) ABSTRACT

Infusion systems and related methods involving a catheter hub and an extension or IV administration set having a male Luer connector for fluid communication with the catheter hub. A support adaptor is provided with the extension or IV
(Continued)

administration set and has a body with a length between first and second ends, and a body wall having a continuous wall surface in a radial direction relative to the length and which defines an exterior of the body. An internal wall of the support adaptor defines a bore with the body wall, wherein the bore has first and second openings. A tubing length is located in the bore and extends out of the second opening. The bore includes first and second bore sections. Optionally, the second bore section is angled relative to the first bore section. A support surface is located beneath the bore, elevation wise.

17 Claims, 15 Drawing Sheets

(51) Int. Cl.
    *A61M 5/14*     (2006.01)
    *A61M 39/12*     (2006.01)
    *A61M 25/02*     (2006.01)

(52) U.S. Cl.
    CPC ........ *A61M 39/10* (2013.01); *A61M 39/1011* (2013.01); *A61M 39/12* (2013.01); *A61M 2025/028* (2013.01); *A61M 2025/0266* (2013.01); *A61M 2039/1038* (2013.01); *A61M 2039/1072* (2013.01); *A61M 2039/1077* (2013.01); *A61M 2205/583* (2013.01); *A61M 2207/00* (2013.01)

(58) Field of Classification Search
    CPC .......... A61M 39/12; A61M 2039/1077; A61M 2039/1088; A61M 2039/1038; A61M 2039/1072; A61M 5/14; A61M 2025/028; A61M 2025/024; A61M 2025/0246; A61M 2025/0206; A61M 2209/088; A61M 2025/0266; A61M 5/148
    See application file for complete search history.

(56) References Cited

U.S. PATENT DOCUMENTS

| | | | |
|---|---|---|---|
| 4,324,236 A | 4/1982 | Gordon et al. | |
| 4,366,817 A | 1/1983 | Thomas | |
| 4,553,961 A | 11/1985 | Pohndorf et al. | |
| D287,882 S | 1/1987 | Glash et al. | |
| D288,005 S | 1/1987 | Glash et al. | |
| 4,698,057 A | 10/1987 | Joishy | |
| D315,822 S | 3/1991 | Ryan | |
| 5,304,144 A | 4/1994 | Brimhall | |
| 5,330,449 A | 7/1994 | Prichard et al. | |
| 5,354,282 A | 10/1994 | Bierman | |
| 5,382,239 A | 1/1995 | Orr et al. | |
| 5,398,679 A * | 3/1995 | Freed ................ | A61M 16/0488 128/207.17 |
| 5,456,671 A | 10/1995 | Bierman | |
| 5,468,228 A | 11/1995 | Gebert | |
| 5,578,013 A | 11/1996 | Bierman | |
| 5,584,874 A | 12/1996 | Rugland et al. | |
| 5,674,201 A | 10/1997 | Steinman | |
| 5,693,032 A | 12/1997 | Bierman | |
| 5,702,371 A | 12/1997 | Bierman | |
| 5,814,021 A | 9/1998 | Balbierz | |
| 5,827,230 A | 10/1998 | Bierman | |
| 5,833,667 A | 11/1998 | Bierman | |
| D408,530 S | 4/1999 | Eliasen et al. | |
| 5,947,931 A | 9/1999 | Bierman | |
| D433,503 S | 11/2000 | Powers et al. | |
| 6,231,547 B1 | 5/2001 | O'Hara | |
| 6,231,548 B1 | 5/2001 | Bassett | |
| 6,290,676 B1 | 9/2001 | Bierman | |
| 6,332,874 B1 | 12/2001 | Eliasen et al. | |
| 6,428,515 B1 | 8/2002 | Bierman et al. | |
| 6,491,664 B2 | 12/2002 | Bierman | |
| D471,979 S | 3/2003 | Wilkinson et al. | |
| 6,554,802 B1 | 4/2003 | Pearson et al. | |
| 6,582,403 B1 | 6/2003 | Bierman et al. | |
| 6,626,437 B2 | 9/2003 | Friend | |
| 6,673,046 B2 | 1/2004 | Bierman et al. | |
| 6,786,892 B2 | 9/2004 | Bierman | |
| 6,827,705 B2 | 12/2004 | Bierman | |
| 6,837,875 B1 | 1/2005 | Bierman | |
| 6,955,659 B1 | 10/2005 | Carter | |
| 6,960,191 B2 | 11/2005 | Howlett et al. | |
| 7,014,627 B2 | 3/2006 | Bierman | |
| 7,112,190 B2 | 9/2006 | Bressler et al. | |
| D539,906 S | 4/2007 | White | |
| D550,353 S | 9/2007 | White | |
| 7,322,963 B2 | 1/2008 | Goh | |
| D567,372 S | 4/2008 | Chesnin | |
| 7,491,190 B2 | 2/2009 | Bierman et al. | |
| D592,303 S | 5/2009 | Chesnin | |
| D613,857 S | 4/2010 | Bierman | |
| D613,858 S | 4/2010 | Bierman | |
| D613,859 S | 4/2010 | Bierman | |
| D613,860 S | 4/2010 | Bierman et al. | |
| 7,744,572 B2 | 6/2010 | Bierman | |
| 7,799,001 B2 | 9/2010 | Bierman | |
| 7,803,138 B2 | 9/2010 | Bressler et al. | |
| D629,514 S | 12/2010 | Bierman | |
| 7,887,515 B2 | 2/2011 | Bierman | |
| 7,967,792 B2 | 6/2011 | Bierman | |
| 8,057,440 B2 | 11/2011 | Bierman | |
| 8,100,862 B2 | 1/2012 | Bierman | |
| 8,177,770 B2 | 5/2012 | Rasmussen et al. | |
| 8,333,735 B2 | 12/2012 | Woehr et al. | |
| 8,357,124 B2 | 1/2013 | Bierman | |
| 8,382,721 B2 | 2/2013 | Woehr et al. | |
| 8,465,458 B2 | 6/2013 | Bierman | |
| 8,475,408 B2 | 7/2013 | Mernoe et al. | |
| 8,585,655 B2 | 11/2013 | Bierman | |
| 8,608,705 B2 | 12/2013 | Peters et al. | |
| 8,636,701 B2 | 1/2014 | Henry et al. | |
| 8,657,791 B2 | 2/2014 | Bierman et al. | |
| 8,679,066 B2 | 3/2014 | Aviles | |
| 8,715,242 B2 | 5/2014 | Helm, Jr. | |
| 8,734,400 B2 | 5/2014 | Ciccone | |
| 8,740,852 B2 | 6/2014 | Aviles | |
| 8,747,360 B2 | 6/2014 | Peterson et al. | |
| 8,834,424 B2 | 9/2014 | Parvatiyar et al. | |
| 9,717,885 B1 * | 8/2017 | Narciso Martinez . | A61M 25/02 |
| D810,287 S | 2/2018 | Bellenoit et al. | |
| 2002/0128604 A1 * | 9/2002 | Nakajima ......... | A61M 39/0693 604/164.01 |
| 2002/0188255 A1 * | 12/2002 | Bierman ............... | A61M 25/02 604/174 |
| 2005/0070849 A1 | 3/2005 | Yang | |
| 2006/0247577 A1 * | 11/2006 | Wright .................. | A61M 5/158 604/174 |
| 2006/0264836 A1 * | 11/2006 | Bierman ............... | A61M 25/02 604/180 |
| 2006/0270994 A1 * | 11/2006 | Bierman ............... | A61M 25/02 604/180 |
| 2006/0276752 A1 | 12/2006 | Bierman et al. | |
| 2007/0106265 A1 * | 5/2007 | Gillis .................... | A61M 39/10 604/534 |
| 2007/0250011 A1 | 10/2007 | Lee | |
| 2008/0027394 A1 | 1/2008 | Bierman | |
| 2008/0243082 A1 | 10/2008 | Goodman | |
| 2009/0036835 A1 | 2/2009 | Bierman | |
| 2009/0149814 A1 | 6/2009 | Bailey et al. | |
| 2010/0100049 A1 * | 4/2010 | Godfrey ............... | A61M 25/02 604/180 |
| 2012/0016312 A1 | 1/2012 | Brown et al. | |
| 2012/0123343 A1 | 5/2012 | Aviles | |
| 2012/0130315 A1 | 5/2012 | Weadock et al. | |
| 2012/0197205 A1 | 8/2012 | Peters | |
| 2012/0232490 A1 * | 9/2012 | Andino ................ | A61M 25/02 604/180 |
| 2013/0345639 A1 | 12/2013 | Spittier | |

(56) References Cited

U.S. PATENT DOCUMENTS

| | | | |
|---|---|---|---|
| 2014/0107584 A1 | 4/2014 | Rosenberg et al. | |
| 2014/0142538 A1 | 5/2014 | Hyman et al. | |
| 2014/0171899 A1 | 6/2014 | Rosenberg et al. | |
| 2014/0249478 A1 | 9/2014 | Bierman et al. | |
| 2014/0276542 A1 | 9/2014 | Ciccone | |
| 2014/0276544 A1 | 9/2014 | Aviles | |
| 2014/0330247 A1 | 11/2014 | Rosenberg et al. | |
| 2014/0343531 A1 | 11/2014 | Larkin | |
| 2015/0250984 A1* | 9/2015 | Humphries | A61M 25/02 604/180 |
| 2019/0321599 A1* | 10/2019 | Burkholz | A61B 5/150992 |

FOREIGN PATENT DOCUMENTS

| | | |
|---|---|---|
| JP | 2000-515393 A | 11/2000 |
| JP | 2002-512864 A | 5/2002 |
| JP | 2009-505735 A | 2/2009 |
| JP | 2012-519551 A | 8/2012 |
| JP | 2013-533023 A | 8/2013 |
| WO | WO 9011795 A1 | 10/1990 |
| WO | WO 9721459 A1 | 6/1997 |
| WO | WO 9955409 A1 | 11/1999 |
| WO | WO 00/12165 A1 | 3/2000 |
| WO | WO 01/52617 A2 | 7/2001 |
| WO | WO 2007024900 A2 | 3/2007 |
| WO | WO 2010102153 A1 | 9/2010 |
| WO | WO 2011162866 A1 | 12/2011 |
| WO | WO 2013086098 | 6/2013 |

OTHER PUBLICATIONS

Office Action from European Patent Office on co-pending EP application (EP16763266.0) dated May 6, 2020.

Extended European Search Report from European Patent Office on co-pending EP application (EP18169425.8) dated Sep. 12, 2018.

Office Action from Japan Patent Office on co-pending JP application (JP 2018-512582) dated Jul. 22, 2020 (dated Aug. 4, 2020).

* cited by examiner

INFUSION SYSTEMS, CONNECTORS FOR USE WITH CATHETER DEVICES, AND RELATED METHODS

FIELD OF ART

The disclosed invention generally relates to intravenous (IV) infusion devices or assemblies, including IV catheters, and connectors of IV administration sets or IV extension lines for use with catheter devices and related methods. In particular, IV catheter assemblies for use with Luer connectors having gap compensation features and catheter assemblies with gap compensation features for use with Luer connectors with or without gap compensation features are disclosed.

BACKGROUND

IV catheters are commonly used for a variety of infusion therapies, including infusing fluids into a patient, withdrawing blood from a patient, or monitoring various parameters of the patient's vascular system. Catheters are typically connected to a catheter adapter that accommodates the attachment of IV tubing known in the art as an IV administration set to the catheter. Following placement of the catheter into the vasculature of a patient, an IV fluid source can be connected to the catheter adapter or catheter hub, sometime by first opening a blood control valve located within the catheter hub. Thus connected, fluid from the IV source can begin flow into a patient through the catheter.

The angle of insertion of the catheter into the patients vein and the length of a typical catheter hub connected with an IV administration set when pushed downwards on the proximal end of the connector can cause the entire connected assembly to tip up on the distal end, which can cause the catheter tube to move within the puncture site and/or cause the catheter to kink off flow, which is undesirable. Consequently, practitioners have been known to add gauze pads or other material under the proximal end of the Luer lock connector to limit or stop the assembly from tipping. Securement dressing and/or adhesive tape are then used to secure the assembly along with the gauze pads to the patient to secure the puncture site. If material is not put under the proximal end of the connector of the IV Administration set, then the administration set cannot be secured to the patient at this point, without causing the above described problem.

SUMMARY

Infusion systems and related methods are disclosed having a catheter hub and a male Luer connector or a male closing cap connectable to the catheter hub. The catheter hub can be part of a catheter assembly with a needle and needle hub and can include a valve, a valve opener, and a needle guard. The male Luer connector can include a collar that is fixed or rotatable relative to a male Luer tip. The collar can have a conically shaped body. The catheter hub can have a body having two centerlines that are angled to one another, or the male Luer connector can have a body having two centerlines that are angled to another, or both the catheter hub and the male Luer connector each can have a body having two centerlines that are angled to one another.

Aspects of the present disclosure include an infusion system comprising: a catheter hub having a catheter tube extending from a distal end thereof; a male Luer connector coupled to the catheter hub; and wherein the catheter hub has a body having two centerlines that are angled to one another, the male Luer connector has a body having two centerlines that are angled to another, or both the catheter hub and the male Luer connector each comprising a body having two centerlines that are angled to one another.

The catheter hub with a body with two centerlines can include a first hub section with a centerline and a second hub section with a centerline and wherein the two centerlines of the first hub section and the second hub section are angled relative to one another.

The first hub section and the second hub section can be singularly formed as a single hub body or made from two hub bodies that are separately formed and subsequently combined or joined.

The infusion system wherein the male connector body can comprise a collar that is rotatable relative to a male Luer tip.

The infusion system wherein the male Luer connector can have a male Luer tip and a tubing coupling each with a centerline.

The infusion system wherein the centerline of the male Luer tip and the centerline of the tubing coupling can be at an angle to one another.

The infusion system wherein the male Luer tip can be concentric with the catheter hub.

The infusion system wherein the catheter hub can comprise a valve and a valve opener.

The infusion system can further comprise a needle guard located inside the catheter hub prior to removal of a needle from the catheter tube.

The infusion system wherein the tubing coupling can comprise a proximal edge, and wherein the proximal edge can be angled radially away from a centerline of the catheter hub.

The infusion system can further comprise gripping portions on the tubing coupling.

The infusion system can further comprise a support feature located externally on the tubing coupling.

The infusion system wherein the support feature can comprise a pair of wings.

The body of the male Luer connector can comprise a collar that is rotatable relative to a male Luer tip or is fixed to the male Luer tip.

The male Luer connector can have a male Luer tip and a tubing coupling each comprising a centerline and wherein the centerline of the male Luer tip and the centerline of the tubing coupling can be at an angle to one another.

The infusion system can further comprise a support feature for supporting the male Luer connector against a surface.

Optionally, part of a collar of the male Luer connector can be supported by the support feature or support adaptor.

The support feature can support a tubing coupling against a surface, can support a collar of a male Luer connector against a surface, or can support both a collar and a tubing coupling against a surface. The surface can be the skin of a patient and the collar can be fixed or a rotatable type, such as a spin-lock collar.

The collar of the infusion system can be conical in configuration.

The conical configuration can be formed by a solid tapering wall or providing a variable gap between two wall layers.

The infusion system can comprise a male closing cap comprising a collar, and wherein the collar can be conical in configuration.

The support feature of the infusion system can be unitarily formed to a tubing coupling of a male Luer connector.

The support feature can have a body wall that is continuous along a radial direction relative to a length or has at least one gap or slit for receiving a tubing.

When the body wall has a gap, adjacent surfaces can overlap so that the gap or slot is physically covered by a section of the body wall so that the exterior wall of the support feature is continuous. The section of the body wall that covers the gap or slot can be pushed apart to expose the gap for installation of the support feature onto a tubing length.

The tubing coupling can comprise a proximal edge and wherein the proximal edge can be angled radially away from a centerline of the catheter hub.

The infusion system can comprise gripping portions on the tubing coupling.

A support feature can be located externally on the tubing coupling. The support feature can comprise a pair of wings.

A further aspect of the present disclosure includes a method of manufacturing an infusion system. The method can comprise the steps: forming a catheter hub with a catheter tube; forming a male Luer connector that is connectable to a proximal opening of the catheter hub; and wherein the catheter hub has a body having two centerlines that are angled to one another, or the male Luer connector has a body having two centerlines that are angled to another, or both the catheter hub and the male Luer connector each comprising a body having two centerlines that are angled to one another.

Yet another aspect of the present disclosure is a catheter assembly comprising a catheter hub, a catheter tube extending distally of the catheter hub, a needle extending distally of a needle hub and through the catheter tube such that a needle tip extends distally of a distal opening of the catheter tube; and wherein the catheter hub has a body having two centerlines that are angled to one another.

The catheter assembly can further comprise a valve comprising at least one slit.

The catheter assembly can further comprise a valve opener for opening the at least one slit when advanced by a male Luer tip.

The catheter assembly can further comprise a needle guard located in the catheter hub, The catheter assembly wherein the needle guard can be located in the catheter hub with a valve and a valve opener.

A still further aspect of the present disclosure is a male Luer connector. Wherein the male Luer connector can include a male Luer tip, a tubing coupling extending in an opposite direction of the male Luer tip, and a collar having internal threads surrounding at least part of the male Luer tip. Wherein the male Luer connector can include a body having two centerlines that are angled to one another.

The male Luer connector wherein the collar can be rotatable relative to the male Luer tip.

The male Luer connector wherein the male Luer tip can have a centerline and the tubing coupling can have a centerline and wherein the two centerlines are angled to one another.

The male Luer connector wherein the tubing coupling can embody a female receptacle for receiving an IV tubing or a male nipple for projecting into an IV tubing.

Aspects of the present disclosure are further understood to include a conically shaped collar, for use with a male Luer connector or a male closing cap, to increase surface contacts with a patient's skin and provide support for an infusion system.

The present disclosure further includes an infusion system comprising a catheter assembly and an extension set or IV administration set. The infusion system can include a catheter hub, having a catheter tube extending from a distal end thereof; an extension set or an IV administration set comprising a male Luer connector comprising a male Luer tip coupled to the catheter hub and a tubing coupling connected to a tubing length extending away from the male Luer tip, said tubing coupling can be spaced from a surface by a set gap. A support feature can be included with the extension set or IV administration set; the support feature can comprise a body with a length between a first end and a second end, a body wall having a continuous wall surface in a radial direction orthogonal to or relative to the length and defining an exterior of the body and an internal wall defining a bore with the body wall.

The bore of the support feature can have a first opening and a second opening having the tubing length located in the bore and extending out the first opening and the second opening. A support surface can locate elevation-wise below the bore, to support a male Luer connector. The support surface can have a slope, such as being wedge shaped. The support feature can be slidable into engagement with the male Luer connector so that the tubing coupling can locate in the bore and contact the internal wall and the set gap can be taken up by the support surface.

Optionally, the internal wall of the support feature can define a support surface that is not sloped or wedge shaped. For example, the support surface can comprise one or more bumps, can comprise sections extending from an enlarged interior of the body wall, or be flat as it extends from the first end to the second end.

A collar can surround the male Luer tip and wherein the collar can be fixed to or rotatable relative to the male Luer tip.

The male Luer tip and the tubing coupling can each comprise a centerline and the two centerlines can be angled relative to one another.

The angle between the two centerlines of the male Luer tip and the tubing coupling can be about 150 degrees to about 175 degrees. In other examples, the range of angle can differ, such as being between 155 degrees to 179 degrees.

The male Luer tip can be concentric with the catheter hub.

The catheter hub can comprise a valve and a valve opener located in an interior cavity of the catheter hub.

A needle guard can be located inside the catheter hub prior to removal of a needle from the catheter tube.

The first opening of the support feature can be larger than the second opening.

The internal wall of the support feature can incline from a first end to a second end. The first opening can be located at the first end.

The internal wall of the support feature can have an undulating surface or ridges.

The support feature can comprise a pair of wings. The wings can extend laterally of the length.

The support feature can comprise a curved upper dome wall surface and a base, and wherein a width at the base relative to a length between the first end and the second end can be wider than a width at the curved upper dome wall surface.

The first opening of the support feature can define a plane and wherein the plane of the first opening can be angled relative to the base by an angle of about 30 degrees to about 75 degrees.

The internal wall of the support feature can define an upper surface of the support surface. The support surface can have a slope. The support surface can be wedged shape.

The upper surface of the internal wall of the support feature can define a plane and wherein the plane of the upper surface can be angled relative to the base by an angle of about 10 degrees to about 35 degrees.

Another aspect of the present disclosure is an infusion system that can have different combinations or alternatives. The infusion system can comprise: a catheter hub having a catheter tube extending from a distal end of a catheter body; an extension set or an IV administration set having a male Luer connector for fluid communication with an open proximal end of the catheter hub; and wherein: (a) the catheter body of the catheter hub has two centerlines that are angled to one another; or (b) the male Luer connector has a body having two centerlines that are angled to one another; or (c) a support feature is provided with the extension set or the IV administration set and wherein the support feature comprises a body with a length between a first end and a second end, a body wall having a continuous wall surface in a radial direction relative to the length and defining an exterior of the body, an internal wall defining a bore with the body wall; the bore having a first opening and a second opening having a tubing length located in the bore and extending out the second opening, the bore comprising a single bore path or comprising a first bore section having a first bore path and a second bore section having a second bore path, which is angled relative to the first bore path by an angle, and a support surface located elevation-wise below the bore; or (d) the male Luer connector comprising a collar surrounding a male Luer tip and the collar being conical in configuration to contact a surface; or (e) a closing cap comprising a collar surrounding a male tip and the collar being conical in configuration to contact a surface; or (f) a combination of two or more of (a), (b), (c), (d), and (e).

The collar can be fixed to or rotatable relative to the male Luer tip or to the male tip.

The male Luer connector can comprise a male Luer tip and a tubing coupling each comprising a centerline and wherein the two centerlines can be angled relative to one another.

The catheter hub can have a first hub section with a centerline and a second hub section with a centerline and wherein the two centerlines of the first hub section and the second hub section can be angled relative to one another.

The tubing coupling can comprise a male nipple or a female receptacle.

The collar can comprise two walls with a variable gap or a wall with a variable thickness to form the conical configuration.

The tubing length can be deflected towards a surface by an interior surface of the second bore section.

The support surface of the support feature can have a slope. The support surface can be wedged shape.

Another aspect of the present disclosure is a method for manufacturing an infusion system that can have different combinations or alternatives. The method of manufacturing the infusion system can comprise: forming a catheter hub having a catheter tube extending from a distal end of a catheter body; forming an extension set or an IV administration set having a male Luer connector for fluid communication with an open proximal end of the catheter hub; and wherein: (a) the catheter body of the catheter hub is formed with a first body section with a centerline and a second body section with a centerline and the two centerlines are angled to one another; or (b) the male Luer connector is formed with a body comprising a tip with a centerline and a tubing coupling with a centerline and wherein the two centerlines are angled to one another; or (c) a support feature is provided with the extension set or the IV administration set and wherein the support feature comprises a body with a length between a first end and a second end, a body wall having a continuous wall surface in a radial direction relative to the length and defining an exterior of the body, an internal wall defining a bore with the body wall; the bore having a first opening and a second opening having a tubing length located in the bore and extending out the second opening, the bore comprising a single bore path or comprising a first bore section having a first bore path and a second bore section having a second bore path, which is angled relative to the first bore path by an angle, and a support surface located elevation-wise below the bore; or (d) the male Luer connector is provided with a collar surrounding a male Luer tip and the collar being conical in configuration to contact a surface; or (e) a closing cap is provided with a collar surrounding a male tip and the collar being conical in configuration to contact a surface; or (f) a combination of two or more of (a), (b), (c), (d), and (e).

Aspects of the present disclosure can further comprise an infusion system comprising; a male Luer connector comprising a body with a male Luer tip at a first end and a tubing coupling at a second end; and a collar located around the male Luer tip; a tubing length having a first end connected to the tubing coupling and a second end connected to a fitting; a support feature is provided with the extension set or the IV administration set and wherein the support feature comprises a body with a length between a first end and a second end, a body wall having a continuous wall surface in a radial direction relative to the length and defining an exterior of the body, an internal wall defining a bore with the body wall; the bore having a first opening and a second opening having a tubing length located in the bore and extending out the second opening, the bore comprising a single bore path or comprising a first bore section having a first bore path and a second bore section having a second bore path, which is angled relative to the first bore path by an angle, and a support surface located elevation-wise below the bore; and wherein the internal wall is inclined from the first opening to the second opening.

Broadly speaking, an infusion system in accordance with aspects of the present disclosure can comprise a catheter assembly and an extension set or IV administration set. The catheter assembly can comprise a hub as described elsewhere herein. The extension set or IV administration set can comprise a male Luer connector as described elsewhere herein. The extension set or IV administration set can comprise a support feature as described elsewhere herein.

A male closing tip as described elsewhere herein can be used with any of the catheter hubs described elsewhere herein.

A further aspect of the present disclosure can include a method of manufacturing an infusion system. The method can comprise: forming a catheter hub with a catheter tube; forming a male Luer connector that is connectable to a proximal opening of the catheter hub; and wherein the catheter hub has a body having two centerlines that are angled to one another, the male Luer connector has a body having two centerlines that are angled to another, a support feature configured for supporting the male Luer connector having a body with a body wall and an internal wall defining a bore having a first opening and a second opening having a tubing length located in the bore and out the first opening and the second opening, or both the catheter hub and the male Luer connector each comprising a body having two centerlines that are angled to one another.

An additional aspect of the present disclosure is an extension set or an IV administration set. The extension set or the IV administration set can comprise: a male Luer connector comprising a body with a male Luer tip at a first end and a tubing coupling at a second end. A collar can be located around the male Luer tip. A tubing length having a first end can connect to the tubing coupling and a second end can connect to a fitting. The fitting can embody any number of commercially available structures. For example, the fitting can include a needleless valve, a Y-site, a universal spike, a drip chamber, a needleless valve with a Y-body, etc. A support feature comprising a body with a length between a first end and a second end can connect to the tubing length. A body wall can have a continuous wall surface in a radial direction orthogonal to or relative to the length and can define an exterior of the body of the support feature. An internal wall can be included defining a bore with the body wall. The bore can have a first opening and a second opening having the tubing length located in the bore and extending out the first opening and the second opening. A support surface can be located elevation-wise below the bore. The internal wall can be inclined from the first opening to the second opening.

Aspects of the present disclosure include an infusion system comprising a catheter hub with a catheter tube attached to a male Luer connector, which can comprise a spin lock collar rotatably coupled to a male Luer tip. The catheter hub, which can be part of a catheter assembly, and the male Luer connector, which can be part of an extension set or an IV administration set, can be provided separately and then subsequently joined or engaged.

A tubing coupling can extend in the opposite direction of the male Luer tip. In an example, the tubing coupling can embody a female receptacle comprising a bore or slot for receiving an end of a tubing, which can be part of an IV administration set or an IV extension line used between the catheter hub and the IV administration set. In other examples, the tubing coupling can embody a male nipple for projecting into an end of the IV tubing.

The catheter hubs described herein can comprise a female Luer taper formed to industry or ISO standard for receiving a male Luer tip or connector. The catheter hub can have a centerline and the male Luer tip can have a centerline and wherein the two centerlines can be angled relative to one another by a small offset angle. For example, the proximal part of the body of the catheter hub or the proximal section of the body of the catheter hub with the female Luer taper can be angled about 1.7 degrees from the centerline of the distal portion of the body. Said another away, the centerline of the proximal portion can be angled to the centerline of the distal portion, which has a common axis with the centerline of the catheter tube by about 1.7 degrees so that the male Luer tip, when inserted into the catheter hub, is angled by the offset relative to the centerline of the distal portion of the catheter hub.

In other examples, the offset angle between the centerline of the distal portion of the catheter hub and the proximal portion of the catheter hub can be other than 1.7 degrees, such as 2 to 6 degrees offset. For a catheter hub with two centerlines with an offset angle of about 1.7 degrees, the catheter hub can be manufactured as a single hub body without resorting to two different hub sections or bodies that are separately manufactured and subsequently assembled.

Thus, an aspect of the present disclosure is a tilted catheter hub having single body or singularly formed hub having two different centerlines and wherein the two centerlines are angled relative to one another, also referred to as an offset angle or angular offset. In an example, the offset angle can be greater than 1 degree, such as 1.2 degrees, 1.5 degrees, or 1.7 degrees.

In some examples, the catheter hub with an angular offset, i.e., two different centerlines that are angled relative to one another, can be usable with male Luer connectors with two different centerlines that are angled relative to another, as further discussed below. Alternatively, the catheter hub can have a single centerline and can be usable with a male Luer connector with two different centerlines that are angled relative to another, also further discussed below.

In some examples, the catheter hub or the body of the catheter hub can have a single centerline and wherein the single centerline of the catheter hub can be concentric with the centerline of the male Luer tip and the two components can have a common centerline or an assembly centerline.

A catheter hub can have a single centerline and be usable with a male Luer connector having an angular offset.

A male Luer connector can have at least two centerlines that are angled relative to one another. For example, a tubing coupling can have a coupling centerline that is angled from a common centerline, and therefore angled from the centerline of the catheter hub and the centerline of a male Luer tip. The offset angle $\alpha 1$ of the coupling centerline can vary within a range of the common centerline. For example, the offset angle $\alpha 1$ can range from about 2 degrees to about 30 degrees to the common centerline. The angle between the two centerlines can be calculated by subtracting 180 degrees from the angle that is based or referenced to a common centerline. Thus, a male Luer connector can have an offset angle $\alpha 1$ of about 2 degrees and the angle between the centerline is about 178 degrees.

In some examples, the angle offset $\alpha 1$ incorporated in a male Luer connector can be greater than 30 degrees, such as 35 degrees. Depending on the length of the tubing coupling and the proximal edge of the tubing coupling relative to a surface, such as to the skin, the angle can vary. In an example, for a given length, the offset angle $\alpha 1$ can be about 24 degrees so that the proximal edge of the tubing coupling can be angled or positioned towards the patient's skin to within about a 2 mm gap, which may be referred to herein as a set gap. However, the offset angle $\alpha 1$, for a given length of the tubing coupling, can be selected so that the proximal edge of the tubing coupling touches the skin, wherein the set gap is zero, or is spaced from the skin by a different value for the set gap, such as 1 mm or greater than 2 mm, such as 3 mm, 4 mm, or greater.

In an example, a set gap, based on the length of a tubing coupling of a male Luer connector and the offset angle $\alpha 1$, is 2 mm, plus or minus 1 mm. This dimension can be selected so that the IV tubing connected to the tubing coupling extends out from the proximal opening of the tubing coupling can project out a small distance before bending against the skin. Thus, in an example, the offset angle $\alpha 1$ utilized in a male Luer connector can be selected so that a tubing length connected to the tubing coupling of the male Luer connector can bridge a set gap and provide support for the proximal end of the tubing coupling and more broadly to the infusion system against the skin. Said another way, an angular offset and a tubing connected to a tubing coupling of a male Luer connector can provide physical support for the proximal edge of the tubing coupling against the skin.

An offset angle can be about 20 degrees to about 26 degrees and the set gap can be about zero to about 4 mm. In some examples, the set gap can be about 4.1 mm to about 7.5 mm. In still other examples, a support for the infusion system at the proximal end of the infusion system can be provided by a center section of the infusion system, such as by the collar of the male Luer connector touching or resting against the skin, in addition to or alternative to the proximal edge of a tubing coupling being supported by a support feature, such as being supported by an IV tubing extending from the tubing coupling or by a support adaptor engaged to the tubing coupling to support the tubing coupling against the skin.

As shown, a collar can have internal threads for threaded engagement with external threads on a catheter hub. The collar can be a spin type that is rotatable relative to a male Luer tip of a male Luer connector. Alternatively, the collar can be a fixed collar and not rotatable relative to the male Luer tip.

A spin lock collar allows a male Luer tip of a male Luer connector to be inserted into a catheter hub and the tubing coupling of a male Luer connector, with an angular offset, to be orientated next to the skin so that a set gap is relatively smaller than if the tubing coupling was orientated away from the skin before the collar is threaded to the external threads of the catheter hub. Thus the infusion system with the spin lock collar and one or more angular offsets allows for the proximal edge of the tubing coupling to be properly orientated relative to the skin before the collar is threaded to the catheter hub. If a tubing length is connected to the tubing coupling, this feature can allow the softer tubing material to contact the skin for a more patient friendly infusion.

A collar in accordance with the present disclosure can include a body comprising a distal end and a proximal end. The body of the collar, at least exteriorly, can be symmetrical about a collar centerline. When so practiced and when in use, the proximal end of the collar can be spaced from the skin by a collar gap. In some examples, the body of the collar can be conically shaped so that the proximal end of the body is larger or wider than the distal end of the body to take up some or all of the collar gap with the skin, such as to close the gap with the skin or touch the skin with the proximal end of the collar. In some examples, the body of the collar can be conically shaped so that one end of the body can be larger or wider than the other end of the body to take up some or all of the collar gap with the skin, such as to close or take up the gap with the skin or touch the skin. The conically shaped collar may be molded as such or may be made as such by a separately formed elastic tapered cushion that is added to, such as placed around, the collar. The male connector and the catheter hub can be made from conventional materials, such as ABS.

A grip impression may be incorporated with the exterior of a tubing coupling of a male Luer connector. For example, the tubing coupling may be sufficiently thick and two diametrically opposed impressions or indentations can be incorporated with the wall or body of the tubing coupling to serve as gripping features. The two grip impressions can provide visual communication to a practitioner regarding where to grip the male Luer connector when assembling the male Luer connector to the catheter hub. The grip impression may be co-molded or insert molded with a different material than the material of the tubing coupling to enhance gripping.

In some examples, a support feature may be added to the tubing coupling, with or without grip impressions. For example, the tubing coupling may be formed with two wings extending laterally of the body of the tubing coupling. The wings can be flexible and/or pliable to yield when pressed against the skin. The support feature, such as the wings or other support adaptor, can be positioned at or near the proximal edge of the tubing coupling on the side of or near the set gap.

When incorporated, a support feature can help to ensure placement or alignment of the proximal edge of the tubing coupling relative to the skin and support the tubing coupling against the skin. The location of the support feature and the shape of the support feature facilitate orienting the side of the tubing coupling closer to the skin before threading the collar to the catheter hub.

The infusion system of the present disclosure may be secured to a patient using an adhesive medical dressing, medical tape or combinations thereof and the offset angle $\alpha 1$ in the male Luer connector, formed by providing at least two centerlines at an angle relative to one another, can allow the proximal end of the infusion system to be positioned closer to the skin than a conventional infusion system without the angular offset $\alpha$. This in turn can allow the infusion system to be secured to the patient with minimal or no set gap, or with a gap that is bridged by a tubing length, to provide a stable system that reduces or eliminates any possibility of moving or disturbing the puncture site.

In an embodiment, two angled centerlines are incorporated in a male Luer connector by forming a male Luer tip with a centerline and a tubing coupling extending from the male Luer tip with a centerline that is angled to the centerline of the male Luer tip. This forms an angle offset within the male Luer connector thereby forming a tilted connector or tilted male Luer connector for minimizing a set gap by an amount compared to when using a male Luer connector without the offset angle $\alpha$.

A male Luer connector of the present disclosure has a male Luer tip, a tubing coupling, and a threaded collar. The threaded collar can be rotatable relative to the Luer tip or the tubing coupling, and can be a spin lock collar. In other examples, the collar can be fixed and not rotatable. The male Luer connector can embody a tilted connector in which the male Luer tip has a center line and the tubing coupling has a centerline and wherein the two centerlines are angled relative to one another by an offset angle $\alpha 1$.

A tubing coupling can optionally include grip impressions formed with the exterior of the tubing coupling. If incorporated, the grip impressions can be continuously formed around the entire circumference of the tubing coupling or can be discontinuous, such as having two opposed impressions on different sides of a centerline. The grip impressions can be unitarily formed with the tubing coupling or separately formed and subsequently attached to the tubing coupling.

A support feature can be provided with a tubing coupling of a male Luer connector. The male Luer connector can have an angular offset or be a standard straight male Luer connector. In an example, the support feature can comprise two wings or flaps extending from a tubing coupling or from a structure attached to the tubing coupling. The support feature can be positioned at or near the proximal edge of a tubing coupling and orientated so that the set gap is supported against the skin.

When wings are incorporated, they can be made longer or shorter or as needed to provide support. The wings can also have joints or weakened lines for adapting to the anatomical features of the back of the hand or arm. When incorporated, the support feature can help to ensure placement or alignment of the proximal edge of the tubing coupling relative to the skin, such as to place the side of the tubing coupling with the support feature closer to the skin, and physically support the tubing coupling against the skin before threading the spin lock collar to the catheter hub. An IV tubing that is part of an extension set or an IV administration set can extend from the tubing coupling.

A male Luer connector can include enlarged grip impressions formed with the tubing coupling of the male Luer connector, such as by forming enlarged wall portions with indentations to serve as gripping means. The tubing coupling can be connected to a tubing section or tubing line, which can be part of an extension set or an IV administration set. Bumps, protrusions, and/or knurls can be included with the grip impressions to enhance gripping.

A support feature can attach or engage the grip impressions of a male Luer connector, at a lower end of a tubing coupling to be placed adjacent the skin. The support feature can embody wings projecting outwardly from a lengthwise axis of an adaptor body for attaching to the male Luer connector. The wings can optionally be omitted. The support feature can be sized and shaped to contact the skin, such as to form a line contact with the skin, to support the tubing coupling against the skin.

The shape of the grip impressions and the location of the support feature when attached to the tubing coupling can provide visual indication or feedback for the user to orientate the tubing coupling so that the proximal edge of the tubing coupling and the support feature face or angle towards the patient when the male Luer tip is inserted into the catheter hub and before tightening the collar to the catheter hub. The grip impressions and the support feature can be unitarily or co-molded to be part of the tubing coupling. In alternative examples, a support feature in the form of a separately formed adaptor having grip impressions and wings may be placed around a tubing coupling to provide the grip and support functions described. For example, an adaptor made from a rubber, plastic or silicone material having a bore can be provided and the tubing coupling inserted into the bore of the adaptor. Optionally, the grip impressions and/or the wings can be omitted from the support feature or support adaptor.

For a support feature embodiment that is separately formed and attached to the tubing coupling noted immediately above in the form of an adaptor, the separately formed adaptor can have a wedge like shape and placed in contact with the tubing coupling of a male Luer connector to support the tubing coupling against the skin, such as to take up the gap normally present between the skin and the tubing coupling. The separately formed adaptor having the wedge shape support can take up the set gap between the proximal edge of a tubing coupling and the skin to provide a physical barrier between the two to support the male Luer connector from rocking up and down relative to the skin.

A separately formed support adaptor of the present disclosure can fit around a tubing coupling of a male Luer connector by forming a bore to receive the tubing coupling, which can have a cylindrical structure or other shaped structures. The structure of the separately formed adaptor can have a continuous body section defining the bore to receive the tubing coupling. The continuous body section of the support adaptor, as the phraseology implies, does not have any slit, gap, or slot to receive a tubing length therethrough. As further discussed below, the tubing length needs to be routed through the two openings of the support feature, via one of the two tubing ends, to connect to the support feature.

In some examples, a male closing cap comprising a male tip and a collar can couple to a catheter hub. In a particular example, the male tip can be inserted into the open proximal end of the catheter hub and the collar can be threadedly engaged to the external threads of the catheter hub.

The male tip of a male closing cap can have a plug for isolating the lumen of the tip, which can close the open proximal end of the catheter hub from fluid flow. The collar can be fixed to the male tip. The collar can have an internal annular collar wall and an external annular collar wall connected to one another by a web and separated along a length by a gap. The male tip and the internal annular collar wall of the male closing cap may be connected to one another by another web.

Internal threads can be provided with the internal annular collar wall of the mail closing cap. A variable gap can be provided between the two walls of the collar to form a conically shaped external collar wall, conically shaped relative to a centerline of the male closing cap. The variable gap between the internal and external annular collar walls may be selected to control the amount of taper, which can bridge or take up space between the collar and the patient, such as take up the set gap.

The conically shaped collar of the male tip may alternatively be tapered by providing a variable wall thickness on one annular wall, such as providing the wall with increasing thickness in the proximal direction to form the conical shape. The one annular wall with the variable wall thickness can resemble the two wall version with the variable gap filled in. In other examples, the collar of the male tip can have a single wall having both internal threads and a variable wall thickness to form the conically shaped collar body.

In yet further embodiments, a spin lock collar, which can rotate relative to the male tip of a male closing cap, can have a relatively constant or straight body or a conically shaped body.

When a catheter tubing is placed in communication with the vasculature of a patient and the catheter hub is to be closed, such as to prevent outward blood flow from the catheter hub, a male closing cap of the present disclosure with a conically shaped collar can be configured to block the proximal opening of the catheter hub, stabilize the catheter hub by providing added surface contact between the collar and a surface, such as the skin, and can stabilize the puncture site to prevent unwanted movement or displacement of the catheter tube from the patient's vein. In some examples, the catheter hub can be a valved catheter hub comprising a valve that closes to restrict or prevent blood flow from flowing in the proximal direction out the catheter hub to provide time for a practitioner to close the proximal end with the male closing cap. The catheter hub can further include a valve opener for opening the valve, when the valve opener is pushed distally by a male Luer tip, such as by a male Luer tip of an infusion line or a syringe tip.

Aspects of the present disclosure further include an infusion system comprising a catheter hub and a male Luer connector attached to the catheter hub. The male Luer connector can include a collar fixed to the male Luer tip, such as not rotatable relative to the male Luer tip. A tubing coupling in the form of a male nipple can be provided at the proximal end of the male Luer connector. The male nipple of the male Luer connector can engage the interior of an IV tubing, which can form part of a tubing line of an extension set or IV administration set. The IV tubing can be configured to wedge in a gap or annular space in between the male nipple and the tubing collar.

A further aspect of the present disclosure is a two-part hub catheter hub, which can comprise a distal hub body or first hub body attached to a proximal hub body or second hub body. The proximal hub body can have a female Luer taper and external threads for threaded engagement with internal threads of a collar of a male Luer connector. The seam where the two hub sections or two hub bodies of the catheter hub attach can be anywhere along an axial position of the catheter hub distal of the Luer taper of the proximal hub body.

The distal hub body of the two-part hub body can have a centerline and the proximal hub body can have a centerline, which can be angled to one another. Thus, the catheter hub with two hub bodies can be a tilted catheter hub in that the proximal hub body can be angled to the distal hub body and the two hub sections can have centerlines that are angled. Said differently, the two-part catheter hub can have two different hub sections with different centerlines having an offset angle α.

In an example, a male Luer connector can have a lengthwise axis that is generally straight and a lumen can form generally around a single centerline. Further, the centerline of the male Luer connector and the centerline of the proximal hub body can be concentric and have a common centerline. The common centerline and the centerline of the distal hub body can be angled to one another. Consequently, where the entire infusion system can normally have a system centerline that is coincident with the centerline of the distal hub body, by incorporating a tilted catheter hub, there can be at least two centerlines that are angled to one another. In an example, the centerline of the distal hub body and the common centerline of the proximal hub body and the male Luer connector can be angled to another.

By angling a proximal hub body relative to a distal hub body of a catheter hub with two hub bodies, a male Luer connector connected to the two-piece catheter hub can shift by the angle offset and move closer towards the skin compared to when no offset angle is utilized. In an example, the proximal edge of a tubing coupling can move closer to the patient's skin due to the angular offset such that the set gap measured between the proximal edge and the skin is reduced compared to similar catheter assemblies with hub bodies that are not tilted or not angled relative to one another.

In an example, the centerline of a proximal hub body can be angled about 5 degrees to about 10 degrees relative to the centerline of a distal hub body. In an embodiment, the angular offset of two centerlines between two hub bodies of a catheter hub is about 8 degrees. However, the range of angular offset can vary and can be less than 5 degrees or greater than 10 degrees. For a particular length and an angle offset between two centerlines a multi-piece catheter hub of about 8 degrees, the proximal edge on a tubing coupling of a male Luer connector from the skin, i.e., the set gap, can be reduced from about 15 mm with no angular offset to about 7 mm. In other examples, the set gap can be smaller than 7 mm, such as 2 mm or 4 mm. The set gap can be made smaller or larger by varying the angular offset and dimensions of the various components.

Aspects of the present disclosure can include a catheter hub, a male Luer connector, or both having an offset angle so that a set gap between a proximal edge of a tubing coupling of a male Luer connector can be reduced compared to similar components without any angle offset. The angle offset can be in the catheter hub only, the male connector only, or both.

An aspect of the present disclosure can further include an apparatus and a system for providing support for a male Luer connector connected to a catheter hub. In an example, the support for the male Luer connector can comprise a structure for bridging a gap between a proximal end of the male Luer connector, such as the proximal end of a tubing coupling, and the patient's skin. By taking up this set gap with a physical barrier, the male Luer connector, which can connect to a proximal opening of the catheter hub, can be kept from rocking up and down relative to a surface, such as relative to a patient's skin.

The physical barrier or support can be called a support feature, structure, or adaptor, which can be used interchangeably. The support feature can comprise forming a catheter hub with at least two sections having two different centerlines that are offset by an offset angle α so that together with a tubing length can provide the physical barrier. The support structure can alternatively be a male Luer connector with at least two sections having two different centerlines that are offset by an offset angle α so that together with a tubing length can provide the physical barrier. The support structure can instead be in the form of a body having a wedge shape adaptor to support the male Luer connector. The body with the wedge shape can be unitarily formed with the male Luer connector or separately formed and subsequently coupled to the male Luer connector. Still alternatively, the support feature can comprise a combination features noted immediately herein.

In some examples, a male Luer connector and/or a support feature can be part of an extension set or an IV administrative set. The support feature can be integral with a male Luer connector or separate from the male Luer connector. For example, a collar for use with a male Luer tip can have a conical or wedge shape to take up a set gap between the skin and a proximal end of the male Luer connector. Alternatively, the collar can be a straight collar and a separate adaptor having a ramp or wedge shape support is placed between the collar and the skin. If a tubing coupling of a male Luer connector extends proximally of a collar, then the support in the form of an adaptor can be attached to the tubing coupling to support the male Luer connector against the skin.

An aspect of the present disclosure can include a method for stabilizing a puncture site having a catheter tube penetrated therethrough, wherein the method can comprise maintaining a male Luer connector at a position relative to the skin of a patient so that the catheter tube is not kinked or bent to restrict flow by more than 20% compared to when the catheter tube is not kinked or bent. The method can comprise using one or more of the support features or structures noted herein.

In an example, an angular offset or offset angle α between two hub sections of a catheter hub (e.g., by utilizing a tilted catheter hub) and a tapered collar can be incorporated so that the collar can be devised to make a line contact, or at least more than a point contact, with the skin of a patient to provide support for the infusion system at the collar. In an example, the collar can be generally constant or straight. In other examples, the exterior profile of the collar can be tapered, such as conically shaped, to improve the surface contacts with the skin to thereby support the infusion system by providing a larger contact surface with the skin compared to a single point contact or a small line contact when the collar is not tapered and/or when an angular offset is not utilized.

A catheter hub provided herein can be a standard one-piece hub body with two sections within the one-piece hub each with a centerline that are angled relative to one another. For example, the centerline of a distal portion of the catheter hub can be angled relative to a second centerline at a proximal portion of the catheter hub. The angular offset between the two centerlines within the one-piece hub body can be about 1.7 degrees with other angles contemplated. Thus, the one-piece catheter hub can be considered a tilted catheter hub in that the catheter hub can have two centerlines that are angled relative to one another.

The one-piece catheter hub with angle offset can be used with a male Luer connector with a single centerline or one that is also tilted, such as having two different centerlines that are angled relative to one another. For example, the one-piece male Luer connector can be tilted and incorporates a conically shaped collar. The tubing coupling of a male Luer connector can be used with the one-piece catheter hub and can embody a male nipple. The collar can be shown fixed to the male Luer tip but may be a spin lock-type collar that can rotate relative to the male Luer tip. A support adaptor can be incorporated to support the tubing coupling and take up any set gap that may be present.

In an example, a male Luer tip of a male Luer connector is concentric with a proximal hub portion of a one-piece catheter hub and the centerline of the proximal portion shares a common centerline with the centerline of the male Luer tip. The common centerline can be angled to the centerline of the distal portion of the catheter hub. Alternatively, the male nipple of a tubing coupling of a male Luer connector can have a centerline that is angularly offset from the common centerline to tilt the proximal edge of the male Luer connector closer to the skin, by reducing the set gap compared to similar components without any angular offset. The angular offset can range from about 4 degrees to about 10 degrees. The angular offset between the centerline of the male nipple and the common centerline can be about 1.7 degrees. The collar can be tapered to match the skin line as close as possible and the variable gap can be adjusted to produce a tapering shape to match the skin line.

In an example, a separately formed support feature can attach to a tubing coupling of a male Luer connector instead of or in addition to utilizing a wedge shaped collar to contact the collar with the skin. The separately formed adaptor can have a wedge-like shape and can place in contact with the tubing coupling and/or against the collar to support the tubing coupling against the skin, such as to take up the set gap normally present between the skin and the tubing coupling.

The separately formed adaptor can have a wedge shape support structure and can take up the set gap between the proximal edge of a tubing coupling and the skin and functions as a physical barrier between the two. The separately formed adaptor can fit around the tubing coupling of a male Luer connector by forming a bore to receive the tubing coupling. The structure of the separately formed adaptor can have a continuous body section defining the bore to receive the tubing coupling via projecting an end of the tubing line through an opening at the two ends of the bore. The tubing coupling can be generally cylindrical in configuration. By installing the support feature onto a tubing length in this fashion, proper installation is assured at the point of assembly of the tubing with the male Luer connector. For example, alignment, orientation, and/or confusion as to how to use the support feature or how to install the support feature can be eliminated.

An infusion system of the present disclosure can comprise a valved catheter hub having a valve located inside a two-part hub body, which can comprise a first hub body and a second hub body. A catheter tube can be placed in a patient's vasculature at a puncture site, such as following successful venipuncture and a needle and needle hub removed from the catheter hub and catheter tube. A valve opener or valve actuator can be slidably disposed in the interior cavity of the catheter hub and can be pushed distally into the valve by the male Luer tip of a male Luer connector to open the valve.

In an alternative embodiment, the catheter hub can be a singularly formed unit having a single hub body without any parting line. The valve can be placed inside the interior of the single hub body and held therein using a groove with one or more shoulders.

Aspects of the valve and valve opener are further described in U.S. Pat. No. 8,333,735, the contents of which are expressly incorporated herein by reference.

A needle guard or tip protector may be incorporated with the catheter hub and removed by a needle and covers the needle tip of the needle when the needle is removed following successful venipuncture. The needle guard can be configured to cooperate with a bump or a crimp, such as a change in profile, on the needle. For example, the change in profile can abut a perimeter defining an opening on a proximal wall of the needle guard to retract the needle guard out from inside the interior cavity of the catheter hub following successful venipuncture. The needle guard or tip protector is also described in the '735 patent. Exteriorly, a pair of wings may be incorporated to a lower section of the hub body of the catheter hub to facilitate securing the catheter hub to the patient.

A male Luer connector with a male Luer tip, a tubing coupling, and a spin lock collar can connect to the valved catheter hub. The male Luer connector can include an angular offset. Thus, the proximal edge of the tubing coupling, which can connect to a tubing section of an extension set or an IV administrative set, can angle towards a surface, such as the skin, and the set gap is reduced compared to a similar infusion system but wherein no offset angle is incorporated between the axis or centerline of the male Luer tip and the centerline of the tubing coupling.

An IV tubing or tubing length connected to the tubing coupling of the male Luer connector with an angular offset can curve or slightly bend against the skin to support the proximal end of the infusion system from rocking or swaying, which can cause the catheter tube to retract or move within the puncture site. In an example, the set gap from the proximal edge of the tubing coupling and the skin can be set by an angular offset of at least two different centerlines of at least two different sections of the infusion system. The set gap can be about 2 mm to about 6 mm with other ranges from zero to 7.5 mm contemplated. In other examples, the set gap can be greater than 2 mm, such as 4 mm or greater, and the set gap is supported by a support feature engaging the tubing coupling.

A separately formed support can attach or engage the tubing coupling instead of or in addition to utilizing a conical shaped collar. Further, the separately formed support can be an adaptor that fits around the tubing coupling, which can connect to a tubing of an extension set or an IV admin set, to support the tubing coupling. The collar can have a conical shape or can be a standard straight collar without a variable wall thickness or a variable gap. The separately formed support, which can comprise a structure having a bore and a ramp or wedge shape body section for supporting the tubing coupling, can be utilized with any of the male Luer connectors discussed elsewhere herein.

A male closing cap with a conically shaped collar can be used with a valved catheter to close the proximal opening of the catheter hub. The collar can touch the skin and support the proximal end of the infusion system from rocking or swaying. The male tip of the male closing cap can seal the open proximal end of the catheter hub but is sufficiently short so as not to push the valve actuator to open the valve.

In some examples, a valved catheter hub can include a catheter hub body that is tilted, i.e., a tilted hub. The tilted hub body can include two different body sections with two different centerlines that are angled to one another.

A valved catheter hub with a titled hub body can include a two-part hub body in which a first hub body has a centerline and a second hub has a second centerline and wherein the two centerlines are angled from one another. In an example, the second hub section can include a cylinder section extending distally of a flange. The cylinder section can be configured to project into the bore of the first hub body. In an example, the projection into the first hub body can be configured to hold or retain a valve between the distal end of the cylinder section and an internal shoulder inside the first hub body.

The second hub body can further comprise a female hub section comprising a female Luer for receiving a male Luer tip of a male Luer connector, which is received by the female Luer and pushes the valve actuator or opener distally forward to open one or more flaps on the valve to open a fluid flow path through the valve. The female hub section can have a centerline that is angled or tilted from the centerline of the cylinder section. The centerline of the cylinder section can be concentric with the centerline of the first hub section. In other words, the cylinder section and the first hub section can have a common centerline.

The offset angle α between the two centerlines of the second hub body may be formed by using two different core pins. The offset angle α between the two centerlines 2 of the second hub body can be about 8 degrees with a range of 1.7 to 24 degrees contemplated. For example, if a smaller offset is desired, the offset angle α can be set to about 1.7 degrees as an example. If a larger offset is desired, the offset angle α can be set to about 24 degrees. Thus, the catheter hub of the present disclosure can include a tilted hub having two different centerlines that are angled relative to one another by an offset angle α.

When a male Luer connector connects to a tilted catheter hub, the proximal edge of a tubing coupling, which can be a male nipple for inserting into a tubing length, can angle towards the skin due to an offset angle α incorporated by the tilted catheter hub. This angling of the proximal edge of the tubing coupling towards the skin establishes a set gap measured between the proximal edge and the skin that is smaller in value than a comparable infusion device in which no offset angle α within the catheter hub is employed. The set gap can be about 4.3 mm for a given length of infusion device and for a given offset angle of about 8 degrees. In other examples, the set gap can be smaller than 4.3 mm, such as 2 mm, and the offset angle can be larger than 8 degrees.

The tilted catheter hub can allow a shoulder on the male Luer connector to rest against the skin and provides another support point for the proximal end of the infusion system. Additional support structures can be provided and extend from the male Luer connector. The additional support structures can be sized and shaped to rest against the skin when the male Luer connector is in use to provide additional supports against the skin.

A set gap can have a range of values and the offset angle of a tilted catheter hub and a tilted male Luer connector can also have a range of offset angle values. Thus, in an example, the infusion system can have two angular offsets, one between two different centerlines of the catheter hub that are angled to one another and the other between two different centerlines of the male Luer connector that are angled to one another.

A male Luer connector of the present embodiment can be a female type receptacle comprising a bore or slot for receiving an end of a tubing, which can be part of an IV administrative set or an extension set. A collar provided with the male Luer tip of the male Luer connector can be a fixed collar and does not spin or rotate relative to the male Luer tip or can be a spin lock collar that can rotate relative to the male Luer tip. The collar can optionally be conically shaped.

The exterior of a collar provided with a male Luer connector can contact the skin and provide another support surface, in addition to an offset angle or in addition to a separately formed support feature, to support, at least in part, the proximal edge of a tubing coupling from rocking or swaying. The tubing coupling can be a receptacle for receiving an end of a tubing length or a male nipple for projecting into an end of a tubing length.

A catheter hub of the present disclosure can include an internal change in profile. The change in profile inside the interior of the catheter hub can be a projection or a recess or a projection adjacent a recess and may be incorporated as a guard engagement surface for engaging a tip protector or a needle guard. The catheter hub with the change in profile can include an offset angle or can be a straight catheter hub without any offset angle.

The internal change in profile can resemble a surface projection or recess in a catheter hub described in U.S. Pat. No. 8,382,721 for engaging a tip protector. The '721 patent is incorporated herein by reference to teach a needle guard and means for engaging the needle guard inside the catheter hub. The catheter hub can be a single hub body, without a seam.

A male Luer connector of the present disclosure can include a body having a male Luer tip on one end of the body and a tubing coupling on the opposite end of the body. The tubing coupling can comprise a male nipple for inserting into an end of a tubing or a female receptacle for receiving an end of the tubing. In the present embodiment, the collar can have a solid wall surface without a variable gap. The solid wall can have a variable wall thickness for forming the tapered surface of the conically shaped collar. The conically shaped collar is configured to contact the skin with a line contact as opposed to a single point contact or a small line contact so as to provide a more stable support system for the infusion system. The collar with the solid wall and tapered surface can be fixed relative to the male Luer tip or be rotatable relative to the male Luer tip.

A catheter assembly of the present disclosure can comprise a catheter hub, a catheter tube extending distally of the catheter hub, a needle extending distally of a needle hub and through the catheter tube such that a needle tip extends distally of a distal opening of the catheter tube. A pair of wings can extend laterally of the catheter hub to provide comfort and additional surfaces for securing the catheter hub to the patient following placement of the catheter tube into the patient's vasculature.

A flashback plug or blood stopper assembly can connect to the needle hub to stop blood flow out the flashback chamber of the needle hub. The flash back plug can be provided at the proximal end the needle hub to allow air to vent but stops blood from spilling out the proximal end of the body of the flash back plug, which can have a chamber and a hydrophobic filter can be assembled in the chamber.

A needle guard or tip protector can be incorporated and can be located in the interior cavity of the hub body of the catheter hub in a ready to use position, which has the needle tip extending distally of the distal opening of the catheter tube. The needle guard can have a proximal wall with a perimeter defining an opening having the needle passing therethrough. Two arms can extend distally of the proximal wall and each can comprise an elbow located distally of the change in profile inside the interior of the hub body in the ready to use position. Placement of the elbows distally of the change in profile can prevent the needle guard from moving in the proximal direction during retraction of the needle following successful venipuncture until the needle tip moves proximally of the two distal walls at the ends of the two arms.

Upon moving the needle tip proximally of the two distal walls following placement of the catheter tube in the vasculature of a patient, the two arms can move radially to reduce the radial profile of the needle guard at the two elbows. Once the radial profile of the needle guard is reduced and is sufficiently smaller than the bore diameter of the interior cavity at the change in profile, the needle guard can move in the proximal direction when pulled proximally by the change in profile on the needle, which can comprise a crimp, a bulge, a material buildup, a sleeve, or combinations thereof, abutting the proximal wall at the perimeter. As the needle retracts in the proximal direction away from the catheter hub, the change in profile can pull the needle guard in the proximal direction out the catheter hub. The needle guard covers the needle tip in a protected position when removed from the catheter hub.

In some examples, a valve and a valve opener can be located inside the catheter hub. Optionally, the needle guard can be located outside of the catheter hub, in a separate guard hub or guard housing. In an example, the needle guard can be located in a hub positioned between the catheter hub and the needle hub.

The catheter hub can be any of the catheter hubs described elsewhere herein. For example, the catheter hub can be a standard hub without an internal change in profile, such as the catheter hub of FIG. 2, can have a tilted hub body with an angular offset α, such as the catheter hub of FIG. 3, or can have a two-part hub body, such as the two-part catheter hub of FIG. 6. Upon placement of the catheter tube into the vasculature of a patient and following removal of the needle and needle guard, any of the various male Luer connectors or male closing caps described elsewhere herein can be used with the catheter hub to either sample fluid or introduce fluid into the catheter hub.

Thus, an aspect of the present disclosure is understood to include a catheter hub having a body with two centerlines that are angled to one another. For example, the distal section of the catheter hub can have a centerline and the proximal section of the catheter hub can have another centerline and wherein the two centerlines can be angled relative to one another. In some examples, the distal and proximal hub sections with two different centerlines can be singularly formed. In other examples, the distal and proximal hub sections can be separately formed and subsequently attached or assembled together using conventional means.

The catheter assembly of the present disclosure can further comprise a valve comprising at least one slit. In some examples, the valves can have three slits defining three flaps, which can be deflected by a valve opener. Thus, the catheter assembly can further comprise a valve opener for opening the at least one slit of the valve when advanced by a male Luer tip, such as by a male Luer connector of the present disclosure, which can have a single centerline or two centerlines that are angled relative to one another.

The catheter assembly can further comprise a needle guard located in the catheter hub, as previously described. The needle guard can have a proximal wall with an opening and the needle can have a change in profile for engaging the proximal wall at the opening. The needle guard can be located in the catheter hub with the valve and the valve opener. For example, the valve opener can have a holding space and at least part of the needle guard can be positioned in the holding space of the valve opener. In other examples, the needle guard can be located in a separate guard housing, such as a hub having a cavity for retaining the needle guard outside of the catheter hub. The guard housing can interact with the catheter hub, such as having a finger abutting or touching the catheter hub in a ready to use position.

A still further aspect of the present disclosure is a male Luer connector. Wherein the male Luer connector can include a male Luer tip, a tubing coupling extending in an opposite direction of the male Luer tip and connected to a tubing length, which can be part of an IV administrative set or an extension set. A collar having internal threads can surround at least part of the male Luer tip. The collar can be fixed and not rotatable or can be movable or rotatable relative to the male Luer tip. The male Luer connector can have a body having two centerlines that are angled to one another. The angle between the two centerlines can be about 155 degrees to about 179 degrees. If 180 degrees, the male Luer connector is understood to not have any angular offset or angle between any two centerlines. An offset angle of 3 degrees from a system or common centerline, as an example, implies an angle between two centerlines of 177 degrees.

A male Luer connector can include a collar and wherein the collar can be straight or can have a wedge shape, with or without a variable gap. The male Luer connector can include a male Luer tip having a centerline and a tubing coupling with a centerline and wherein the two centerlines can be angled to one another. The angle between the two centerlines can be about 155 degrees to about 179 degrees. Alternatively, the male Luer connector can be without any offset angle.

Additionally or alternatively, a separately formed support feature, similar to the support feature discussed with reference to FIG. 1B, can be attached to or engage a tubing coupling of the male Luer connector instead of or in addition to utilizing an angular offset of a catheter hub and/or an angular offset of a male Luer connector. Further, the separately formed support feature can fit around or locate around the tubing coupling of the male Luer connector, which can connect to a tubing of IV administrative set or extension set, to support the tubing coupling and possibly also support part of the collar, which can be a straight collar without a variable wall thickness or a collar with a variable gap or thickness.

The separately formed support feature can comprise a structure having a bore and a wedge shape body section for supporting the tubing coupling of a male Luer connector and can be used with various male Luer connectors discussed elsewhere herein.

The male Luer connector can include a tubing coupling opposite an end with a male tip that can embody a female receptacle for receiving an IV tubing or can embody a male nipple for projecting into an IV tubing. The tubing length can be part of an extension set or an IV administrative set.

Aspects of the present disclosure are further understood to include a conically shaped collar, for use with a male Luer connector or a male closing cap, to increase surface contacts with a patient's skin and provide support for an infusion system. The conically shaped collar can be fixed relative to a male Luer tip or be rotatable relative to the male Luer tip.

Internal threads can be provided with the conically shaped collar. A separately formed support feature can be used with an infusion system comprising a conically shaped collar.

The catheter hubs described herein can have a single centerline or two centerlines or can be formed from at least two hub sections with two centerlines that are angled to one another for use with a male Luer connector with a single centerline or with two centerlines that are angled to one another.

An extension set having a male Luer connector can connect to a catheter hub having a catheter tube accessing the vasculature of a patient at a puncture site. The catheter hub and the male Luer connector can rest against a surface, such as the patient's skin. An extension set can be used with any of the various catheter hubs described herein and the extension set can include any of the male Luer connectors described herein.

The extension set or IV administration set of the present disclosure can include a support feature having a continuous body wall defining a bore and a tubing length passing through the bore and the tubing length attached to a male Luer connector at one end and to a fitting at another end. The support feature can have a ramped or sloped support structure, can slide along the length of the tubing, and can rotate about the length of tubing.

The support feature can slide into contact with the male Luer connector so that a tubing coupling of the male Luer connector projects into the bore of the support feature. The support feature can optionally include gripping features and/or wings. If incorporated, the wings can extend laterally of the body of the support feature, such as laterally of a lengthwise axis near a base of the support feature.

An extension set of the present disclosure can include a tubing coupling at an end of a male Luer connector connected to a first end of a tubing length and a fitting, such as a needleless valve, can connect to a second end of the tubing length. A slide clamp can be provided between the two ends of the tubing to clamp the tubing. A roller clamp may also be included and mounted over the tubing in addition to the slide clamp. If the extension set was instead an IV administration set, the length of tubing can be longer and the fitting could be a universal spike having a drip chamber instead of a needleless.

In some embodiments, a Y-site with a needleless valve or other fittings can be included with the IV administration set or the extension set. The extension set and the IV administration set can still include other components and the set can be customizable as needed to include multiple needleless valves, multiple Y-connectors, or to include other fittings. Thus, the exemplary components described herein for the extension set and IV administration set are not limited.

The male Luer tip of a male Luer connector can connect an extension set to a catheter hub and allows fluid to be administered through the catheter hub and out the catheter tube, such as by injecting fluid with a syringe at the needleless valve into the patient via the catheter hub and catheter tube. A spin lock collar on the male Luer connector can be threaded to the external threads of the catheter hub to more securely hold the male Luer connector to the catheter hub. Optionally, the collar can be omitted and the male Luer tip is used as a Luer slip.

When an infusion system is placed in communication with a patient, the angle between the assembly centerline of a catheter hub and male Luer connector and the surface of the skin can be about 12 degrees to about 16 degrees. If a standard non-angular offset male Luer connector and/or a standard non-angular offset catheter hub are used, the proximal edge of the tubing coupling of the male Luer connector to the surface of the skin, called a set gap, can be about 22 mm to about 26 mm. These ranges can of course vary depending on the length and geometries of the various components. Notwithstanding the range variations, an unsupported set gap can allow the entire infusion system, such as the tubing coupling, to move up and down relative to a surface or the skin, unintentionally or otherwise, so that the set gap can vary from zero to some large gap value relative to the skin. When the tubing coupling is so moved, the catheter tube at the puncture site can bend, displace proximally, and/or kink and obstructs fluid flow through the infusion system, among other problems.

The male Luer connector can be supported at the tubing coupling so that a physical barrier is interposed between the skin and the tubing coupling to take up any gap therebetween. Said differently, the infusion system of the present disclosure can include means for supporting the male Luer connector at the tubing coupling against the skin.

In an example, the catheter hub can be provided with an angular offset α, the male Luer connector can be provided with an angular offset α1, or both the catheter hub and the male Luer connector can be provided with angular offsets α, α1 to relocate the proximal edge of the tubing coupling closer to the skin or touch the skin compared to a prior art infusion system without any angular offsets. As described above, an angular offset can be incorporated in a catheter hub and/or in a male Luer connector by forming a structure with at least two sections each having a centerline that are angled relative to one another.

A support feature in the form of a separately formed adaptor may be placed around the tubing coupling to provide support. For example, following placement of the catheter tube into the vasculature of the patient at the puncture site, the adaptor can slide under the tubing coupling to take up any gap that may be present between the skin and the proximal edge of the tubing coupling to physically support the male Luer connector from possible rocking up and down relative to the skin at the proximal end of the tubing coupling.

The support feature can be used with the tubing coupling of a male Luer connector with or without an angular offset. For example, if the male Luer connector is a standard connector without any angular offset α, then the adaptor can be configured to take up a typical set gap of about 22 mm to about 26 mm to physically support the tubing coupling against the skin. If the male Luer connector incorporates an angular offset α1 so that the proximal edge of the tubing coupling is repositioned closer to the skin, then the support adaptor only has to take up a relatively smaller set gap, typically less than the range of 22 mm to 26 mm, to physically support the tubing coupling against the skin. In an example, the support adaptor can be sized and shaped to take up a range of set gaps by incorporating a ramped surface, similar to a wedge or a tapered shim, to take up any slack of a certain range, such as between 2 mm and 30 mm. The ramped or wedge shaped structure allows the gap between the tubing coupling and a surface, such as the skin, to be taken up in increments of the slope of the ramped structure. Optionally, the support surface can be other than a continuous sloped surface. For example, the support surface can have a series of projections for supporting the tubing coupling.

The support, support feature, or adaptor, used interchangeably, can be a molded plastic piece having a body with a generally boot-shaped side elevation. The body can instead be molded or formed from an elastomer, for example from rubber or silicone. The body can have a base or base wall, a first end, a second end and a body wall with a curved upper dome wall surface. The body can comprise a support opening accessible from the first end and a through opening accessible from the second end.

The body wall can be continuous, such as being a continuous wall. By continuous, the body wall, including the curved upper dome wall surface, can be without a gap, a slit or a slot extending through the wall to permit a tubing length to engage the support feature through the gap, slit, or slot. The body wall therefore has a continuous wall surface in a radial direction orthogonal to or relative to a length between the first end and the second end of the body. The body wall defines an exterior of the body.

A through bore can be defined by the body wall and an internal wall between the support opening and the through opening, which can also be referred to as a first opening and a second opening, respectively. Further, because the adaptor can be oriented so that the first opening is closer to a male Luer connector and the second opening further away when located on a tubing of an IV administration set or extension set, the first opening may also be referred to as the distal opening the second opening as the proximal opening. As disclosed, a tubing length can only connect to the support feature or adaptor by passing an end of the tubing length through both the first and second openings since there is no gap, slit or slot in the continuous body wall. Once the tubing length is located within the bore, the support feature is rotatable about the tubing length and the tubing length is located in the bore that is bounded by a continuous wall around the entire circumference of the bore. Optionally, the extension set and IV administration set described herein can be without the separately formed support feature. By installing the support feature onto a tubing length in this fashion, proper installation is assured at the point of assembly of the tubing with the male Luer connector. For example, alignment, orientation, and/or confusion as to how to use the support feature or how to install the support feature can be eliminated.

The through opening or proximal opening of the support can have an opening diameter of about 4 mm to about 5.5 mm, or as necessary to accommodate a typical tubing diameter of an IV admin set or an extension set. The support opening or distal opening can be sized to be larger than a diameter of the largest cross-section of a tubing coupling, in the order of about 15% or larger, such as 50% larger or 75% larger than the tubing coupling. As further discussed below, a tubing line of an IV admin set or extension set can pass through the bore of the support and the support can be configured to slide under the tubing coupling of a male Luer connector to support the tubing coupling against a patient's skin.

The support opening can be defined by an inclined perimeter, which resembles an exponential slope along a side view so as to define a wide support opening that is angled. The wide support opening can be sized and shaped to readily receive a proximal end of a tubing coupling when the support adaptor or feature slides under a male Luer connector to support the tubing coupling.

The wide support opening can be sized and shaped to accommodate some misalignment between the distal opening and the proximal end of a tubing coupling while still allow the two to mate. The first opening or support opening of the support feature can define a plane and wherein the plane can be angled relative to the base by an angle of about 20 degrees to about 80 degrees. In a particular example, the angle between the plane defined by the first opening and the base is from about 35 degrees to about 75 degrees, such as 45 degrees to 65 degrees.

In an example, the internal wall can extend from the first end to the second end of the body and slopes elevation-wise upwardly, as it extends to the second end. A radius or bevel can be provided at the proximal end of the bore next to the through opening so as to define a reduced opening at the through opening compared to the bore diameter adjacent the through opening.

The bore can be bounded by a retaining lip or shoulder. In an example, the retaining lip or shoulder is configured to stop the tubing coupling of a male Luer connector from moving further proximally beyond the lip but the tubing is allowed to pass through the second or proximal opening. The radius or bevel may be configured to compliment the bevel on the proximal end of the tubing coupling, as shown in FIG. 23.

In an example, the internal wall of the support feature can undulating as it inclines from the first end towards the second end. In other examples, the internal wall can be generally flat as it inclines. The internal wall, which can define a support surface, can optionally be flat and not sloped or embodies a plurality of spaced apart projections. In still other examples, knurls or ridges may be provided on the upper surface of the internal wall to provide latching points or resting points for the tubing coupling as the tubing coupling is received inside the bore. Optionally, the inside surface of the curved upper dome or the inside surface of the two sides or both can incorporate undulating surfaces, knurls or ridges to provide latching points or resting points for the tubing coupling.

In an example, the bore and the surface contour of the internal wall of the support feature can be sized and shaped to snuggly receive a proximal end of a male Luer connector, such as to snuggly receive a tubing coupling. For example, the bore and the surface contour of the internal wall can be sized and shaped to snuggly receive Model No. 1234 male Luer connector from Company XYZ, wherein the model number and the company can represent any of the various manufacturers of commercially available male Luer connectors.

In an example, the bore can taper or can be approximately frustoconical as it extends from the first end to the second end. Optionally, the bore is a straight bore. Further, the inclined surface of the internal wall and the base of the support adaptor can define a ramp or wedge shaped structure. The wedge shaped support can be located elevation-wise below the bore. The upper surface for the wedge shape support can define part of the bore. The ramp or wedge shaped structure can be configured to function as a shim to fill up or take up space between the tubing coupling of a male Luer connector and a surface, such as a patient's skin, to physically support the tubing coupling against the surface. Optionally, the internal wall provides a support surface that is not inclined or not continuous, such as formed by a plurality of bumps.

The wedge shaped structure of the support adaptor can act as a shim with a variable thickness to take up different set gaps between the proximal edge of a tubing coupling and the skin, from about a 2 mm set gap up to about a 24 mm set gap to about a 30 mm set gap. However, the set gap range that the support adaptor can support is not limited as the structure of the support adaptor or feature can be modified to support a larger range, such by making the support feature longer lengthwise and/or the sloped internal wall steeper.

When in use and as the wedge shaped structure supports the tubing coupling of a male Luer connector, the internal wall and the body wall defining the bore of the adapter can secure the tubing coupling from lateral movement, upward movement, or both. For example, the interior surface defining the bore can confine the tubing coupling from movement.

In some examples, the internal wall of the support feature can function as a support surface and can be generally planar, flat, not continuous, have a plurality of bumps, or combinations thereof.

The upper surface of the internal wall of the support feature can define a plane and wherein the plane of the upper surface can be angled relative to the base. The angle between the plane of the upper surface and the base can be about 5 degrees to about 45 degrees with all values in between being contemplated. To provide a more gradual inclined support surface, the angle between the plane of the upper surface and the base can be about 15 degrees to about 35 degrees.

A void space may be formed in the support to reduce materials to mold the support and therefore reduce costs. The void space can also introduce additional resiliency to the body of the support. The resiliency of the support may otherwise be controlled through material selection and durometer. The void space can optionally be omitted, such as by molding a solid body. The void space, when incorporated, can be defined by the interior surface of the base and the lower surface of the internal wall, which can also divide the void space and the bore.

In an example, the void space, when incorporated, extends from a void space opening at a second end towards a first end of the body. The first end of the void space can be a closed end. Because the void space can be bounded by the sloped internal wall and the base, the void space can have a wedge shape similar to the wedge shaped support structure for supporting the male Luer connector. However, the void space can have a different shape than the shape of the support structure. Optionally, the void space can be provided with ribs to reinforce the internal wall.

The undulating surface of the internal wall may comprise different angles of inclination from the first end towards the second end of the body. The internal wall may have an initial steep inclined upper surface, called the entry region. The entry region may serve to facilitate capture of the tubing coupling of a male Luer connector and assist in guiding it deeper into the bore. Further in the bore, the internal wall can have a central or middle region and an end region. In use and depending on how far the support adaptor is pushed over a male Luer connector to receive a tubing coupling, the tubing coupling of the male Luer connector can rest against the entry region, the middle region, the end region, or between two or more of the regions.

In an example, the middle region can take up a greater set gap than the entry region because it is located elevation-wise further up the sloped internal wall than the entry region. In an example, the end region can take up a greater set gap than the middle region because it is located elevation-wise further up the sloped internal wall than the middle region.

The internal wall can have a generally concave top surface and slopes upward from the first end towards the second end to receive the proximal end of a male Luer connector and guide it into the bore.

The support feature can have different widths when viewing down the length of the body of the support feature. The base has a width and the curved upper dome wall surface of the body wall has a width, which can be smaller than the width at the base. The width of the base can be about 30% to about 100% wider than the width of the curved upper dome wall surface. In other examples, the width of the base can be greater than 100% of the width of the upper dome wall surface.

The wider dimension at the base can indicate which end of the support feature is to be positioned against the skin. As dimensioned, the relatively wider base can provide a stable surface area against tilting and for providing a greater contact area with a patient for patient comfort. For example, when applying adhesive to secure the support feature to the patient, the wider base resists tilting or tipping. A foam pad or cushion may be added to the lower exterior surface of the base for added patient comfort. Optionally, a pair of wings can be provided extending laterally from the two sides of the body, from near the base.

In an example, the curved upper dome wall surface of the body of the adaptor is continuous along a radial direction, which is orthogonal to the lengthwise axis or length of the support adaptor. The base as well as the sides of the body can also be continuous without any slit or slot. Because of the continuous body wall, including a continuous upper dome wall surface and continuous base, the adaptor must be mounted onto a tubing length of an extension set or an IV administration set by passing an end of the tubing length through both the distal opening and the proximal opening to be located in the bore.

In an example, there is no side slot or channel in the support to otherwise mount the support to the tubing, or vice versa, via from a side of a tubing length. Said differently, at least one end of a tubing length must be routed through the bore and the two openings of the support to mount or assemble the support to an IV admin set or extension set with a continuous body wall. The continuous nature of the upper dome surface and of the body wall can require the support adaptor to be assembled and provided as part of an extension set or IV administration set with a tubing length inside a bore of the support adaptor in a packaged or manufactured state, especially with the tubing section secured at its two ends. Less preferably, the tubing length can be detachable from a fitting or from a male Luer connector of an extension set or IV administration set to route through the bore and the two openings of the support feature and then re-connected.

Thus, an aspect of the present disclosure is understood to include an extension set or an IV administration set comprising a male Luer connector at a first end of a tubing length and a fitting at a second end of the tubing length, and wherein the male Luer connector has a tubing coupling having a support structure for supporting the tubing coupling against a patient's skin, when the extension set or the IV administration set is used with a catheter hub having a catheter tube. In an example, the support structure can be unitarily formed with the tubing coupling. In another example, the support structure can be separately formed and movable into contact with the tubing coupling to support the tubing coupling against the patient's skin. The support structure can optionally include a pair of wings.

The support structure can comprise an angular offset within the catheter hub so that an end of a tubing coupling of a male Luer connector connected to the catheter hub is moved closer to the skin due to the angular offset.

In another example, the support structure can comprise an angular offset within a male Luer connector so that an end of a tubing coupling of the male Luer connector is moved closer to the skin due to the angular offset.

In yet another example, the support structure can comprise a support feature sized and shape to function as a shim to take up any space or gap between a proximal end of a tubing coupling of a male Luer connector and a surface, such as the skin. The support feature can be unitarily formed with the tubing coupling of a male Luer connector or be separately formed and movable into contact with the tubing coupling. The separately formed support feature can comprise a body comprising a bore bounded by a continuous wall and having a first opening and a second opening at the ends of the bore. The first opening can be larger than the second opening and can be an angled opening. In yet other examples, the support structure can comprise a combination of structures described herein.

The second or proximal opening of the support feature can be generally centrally positioned relative to the curved upper dome wall surface of the body wall and relative to the two sides of the body.

The void space opening to a void space within the body of the support feature can have an irregular shaped opening having many sides and angles. In other examples, the void space opening can be round, square, or polygonal.

When viewing the support feature down the lengthwise axis of the support feature, the first or distal opening can be resemble a trapezoid with the lower perimeter section closer to the base being wider than the upper perimeter section closer to the upper dome surface. Thus, the first or distal opening can not only incline, the perimeter of the first opening can also taper inwardly at it inclines.

An extension set or an IV administration set of the present disclosure can include a support feature or support adaptor. Although applicable to both sets, the following discussion is relative to an extension set. The extension set of the present disclosure can include a support adaptor having a tubing length passing through the bore and the two openings of the body. The support adaptor can be the similar to the adaptor of FIGS. 18-21. The support adaptor can be located along a tubing length at a before "B" position away from the tubing coupling of a male Luer adaptor and movable to an after "A" position, or engaged position, in contact with and supporting the male Luer adaptor. In the before "B" position, the support adaptor is rotatable relative to the tubing length and the tubing length is located within the bore bounded by a continuous wall.

In an example, the catheter hub can be a standard hub with a single system centerline and the male Luer connector can be a standard connector with a single connector centerline. In other words, neither component incorporates an angular offset. Thus, in the infusion position, the proximal edge of a tubing coupling of a male Luer connector can be spaced from the skin by a set gap while maintaining the catheter tube along a relatively straight axis so as not to restrict flow through the catheter tube.

To take up the set gap and support a tubing coupling of a male Luer connector against the skin, the support adaptor can slide distally relative to a catheter hub from position B to position A to take up the set gap. During this movement, the length of tubing is allowed to pass through the bore between the support opening and the through opening. The support adaptor can have an upper dome wall surface, which can have a continuous wall surface without any slit or slot. In the engaged position, at position A of the support feature, the tubing coupling can be physically supported against a surface, such as the skin of a patient.

If the catheter hub of the infusion system has an angular offset, the male Luer connector has an angular offset, or both the catheter hub and the male Luer connector have angular offsets, then the support adaptor for supporting the male Luer connector can be unitarily formed to the male Luer connector or can be separately formed and can comprise or can incorporate a slit or slot to enable mounting the support adaptor onto the tubing length of the extension set or IV admin set by passing the tubing length through the slit or slot on the support adaptor.

Where an angular offset is incorporated and where a separately formed support feature is used, a tubing length can slide through a gap, slit, or slot and not have to pass through the two openings of the support feature to mount the support feature to the tubing. Thus, where a slit or a slot is provided with a support adaptor or feature, the support adaptor can be added to the tubing length of an extension set or an IV administration set after the tubing length has been connected at the tubing's two ends.

The support adaptor or feature is slidable along the tubing into an engaged position or after position A in contact with the tubing coupling of the male Luer connector, at the proximal end of the tubing coupling. In the engaged position between the support feature and a male Luer connector, the tubing coupling can enter the support opening at the first end of the body. The support adaptor can move over the tubing coupling to support the tubing coupling and take up the set gap between the proximal edge of the tubing coupling and the skin. Depending on the dimension of the set gap, the support adaptor can move over the tubing coupling so that the tubing coupling rests against the entry region, the middle region, or the end region of the internal wall of the support adaptor. The tubing coupling can optionally rests between two or more of the regions inside the bore.

The support adaptor or feature can move a maximum amount over the tubing coupling until the proximal end of the tubing coupling contacts the lip or shoulder inside the bore near the second end of the body. The amount of engagement between the support adaptor or feature and the tubing coupling can be selected by the practitioner to provide the most optimum alignment for the catheter tube at the puncture site. Once engaged at a desired position, securement tape or adhesive may be applied over the catheter hub, the male Luer connector, the tubing adaptor, or combinations thereof to maintain the catheter tube at the desired alignment or angle with the tubing coupling supported by the support feature.

The support adaptor may be composed of any material compatible with human contact, but will typically be composed of a plastic, typically a thermoplastic material suitable for injection molding. The plastic may be comprised of one or more different polymers, such as polyolefins. In one embodiment, the body of the stabilizer is composed of polyethylene, and in particular LDPE. The support adaptor may alternatively be made form a rubber or silicone material.

The support adaptor of the present disclosure can be elongated and the bore, formed by a continuous body wall, incorporates an angular offset $\alpha 2$. The bore with the angular offset can be provided with a first bore section having a first bore centerline and a second bore section having a second bore centerline, which can be angled relative to the first bore centerline by an angle of from about 140 degrees to about 179 degrees. The first bore centerline can be collinear with the common centerline of the catheter hub, the male Luer connector, or be angled to the common centerline. In an example, the angle between the first and second bore centerlines is from about 150 degrees to about 170 degrees.

As the first bore section and the second bore section can have undulating surfaces or curves but still extend along a general direction, the first bore section 442A and the second bore section 442B can be described as having a first bore path and a second bore path, respectively, which can be understood to include some bending, non-linear sections, or linear sections. The bore therefore can have a first bore section having a first bore path and a second bore section having a second bore path and wherein the two bore paths can be angled relative to one another.

The two bore paths being at an angle to one another can be employed to change the direction of a tubing length extending out a tubing coupling to generally conform to the two bore paths. In other examples, there can be more than two bore sections within the bore with more than two bore paths to angle or bend the tubing along more discrete paths within the bore.

The proximal end of the tubing coupling of a male Luer connector can fit snuggly within the bore or the bore inside diameter can be larger than the tubing coupling and not grip the exterior of the tubing coupling. When in contact with a male Luer connector, the tubing coupling of the male Luer connector can be positioned within the first bore section while the tubing length can extend through the second bore section having the second bore centerline and out the through opening at the second end of the support adaptor.

The inside diameter of the second bore section can be larger than the outside diameter of the tubing length so that the exterior of the tubing length is not gripped by the interior surface of the second bore section. Alternatively, only part of the second bore section is sized to snugly grip the exterior of the tubing length or the entire second bore section snugly grips the exterior of the tubing length.

In some examples, the second bore section can have a second bore path that is parallel to the bottom surface of the body of the support feature and wherein the second bore path can be angled relative to the first bore path of the first bore section. When so configured, the through opening at the second end of the support feature can be made or sized to be wider or larger than the rest of second bore section, at least wider or larger in the lower direction elevation-wise to allow the tubing to bend towards the patient's skin as an adhesive dressing is applied. This can act as a stress relief to avoid kinking off flow through tubing extending out the enlarged through opening. In an example, the through opening can enlarge from the inside diameter of the second bore section in the proximal direction, similar to an expander or enlarger. In another example, a proximal end of the second bore section can have a frustoconical shape.

As configured, the tubing length can be deflected towards the surface, such as the skin of a patient when the infusion system is in use for IV access, by the extended bore, and specifically by the second bore section with the second centerline. The tubing length can contact an upper interior surface of the bore to be deflected towards the skin by the upper interior surface. However, the tubing length can contact other interior surface areas of the bore to deflect towards the skin. The angle of the second bore centerline can be selected to deflect the tubing length towards the surface a gradual amount from its normal bend or a steeper amount from its normal bend to close the gap between the tubing and the skin. By incorporating a support adaptor with a bore with an angular offset to direct the bend of the tubing length, this feature can eliminate the risk of kinking off the flow through the tubing and allows full coverage by a sterile adhesive dressing.

Thus, aspects of the present infusion system can include a number of features described herein. The infusion system can comprise: a catheter hub having a catheter tube extending from a distal end of a catheter body; an extension set or an IV administration set having a male Luer connector for fluid communication with an open proximal end of the catheter hub; and wherein: (a) the catheter body of the catheter hub has two centerlines that are angled to one another; (b) the male Luer connector has a body having two centerlines that are angled to another; (c) a support feature is provided with the extension set or the IV administration set and wherein the support feature comprises a body with a length between a first end and a second end, a body wall having a continuous wall surface in a radial direction orthogonal to or relative to the length and defining an exterior of the body, an internal wall defining a bore with the body wall; the bore having a first opening and a second opening having a tubing length located in the bore and extending out the first opening and the second opening, the bore can be straight with a single bore centerline or the bore can include a first bore section having a first bore centerline and a second bore section having a second bore centerline, which is angled relative to the first bore centerline by an angle, and a support surface is located elevation-wise below the bore; (d) a male closing cap comprising a collar fixed to a male tip and the collar being conical in configuration to contact a surface at an angle; or (e) combinations of (a), (b), (c), and (d). The combinations of (a), (b), (c), and (d) are broadly construed to mean any combination. For example, the combination can mean any two or more of (a), (b), (c), and (d).

Method of manufacture and method of use of the infusion systems, catheter assemblies, extension sets, IV admiration sets, and components thereof are within the scope of the present disclosure.

BRIEF DESCRIPTION OF THE DRAWINGS

These and other features and advantages of the present devices, systems, and methods will become appreciated as the same becomes better understood with reference to the specification, claims and appended drawings wherein:

DETAILED DESCRIPTION

The detailed description set forth below in connection with the appended drawings is intended as a description of the presently preferred embodiments of catheter assemblies, connectors, and infusion systems provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

In the following description, numerous specific details are set forth to provide a more thorough description of the invention. It will be apparent, however, to one skilled in the pertinent art, that the invention may be practiced without all of these specific details. In other instances, well known features have not been described in detail so as not to obscure the invention. The claims following this description are what define the metes and bounds of the invention.

Figure 1:
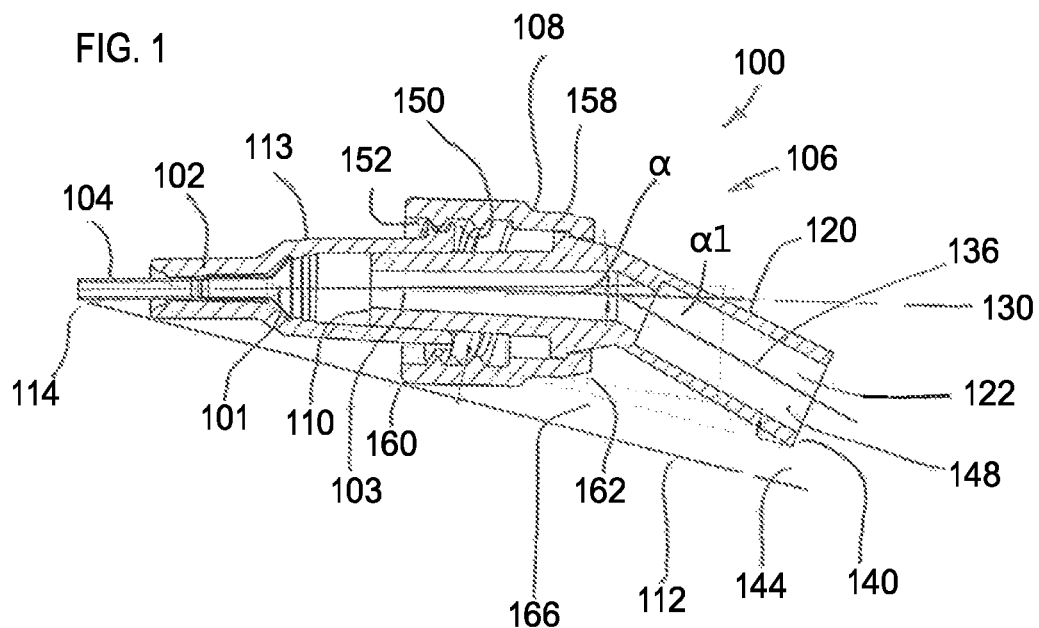
FIG. 1 is a schematic cross-sectional side view of an infusion system provided in accordance to a first aspect of the present disclosure.

With reference now to FIG. 1, an infusion system 100 is shown comprising a catheter hub 102 with a catheter tube 104 attached to a male Luer connector 106, which comprises a spin lock collar 108 rotatably coupled to a male Luer tip 110. A tubing coupling 120 extends in the opposite direction of the male Luer tip 110. In an example, the tubing coupling 120 embodies a female receptacle comprising a bore or slot 122 for receiving an end of a tubing (not shown), which can be part of an IV administration set or an IV extension line used between the catheter hub and the IV administration set. In other examples, such as in the embodiment of FIG. 3, the tubing coupling 120 can embody a male nipple 128 for projecting into an end of the IV tubing.

The catheter hub 102 may be part of a catheter assembly comprising a needle hub and a needle and wherein the needle hub and needle have been removed from the catheter hub 102 and the catheter tube 104, such as following successful venipuncture and the catheter tube is placed into the vasculature of a patient. This applies to other embodiments disclosed herein. The catheter hub 102 of the present embodiment and other catheter hubs described elsewhere herein can comprise a female Luer taper formed to industry or ISO standard for receiving a male Luer tip or connector. In the present embodiment and elsewhere, the patient's skin 112 is represented by a line that the infusion system 100 rests against and the puncture site is indicated with element 114. The catheter hub 102 has a centerline 101 and the male Luer tip 110 has a centerline 103 and wherein the two centerlines are angled relative to one another by a small offset angle. For example, the proximal part of the body 113 of the catheter hub or the proximal section of the body 113 of the catheter hub 102 with the female Luer taper can be angled about 1.7 degrees from the centerline of the distal portion of the body 113. Said another away, the centerline 101 of the proximal portion can be angled to the centerline of the distal portion, which has a common axis with the centerline of the catheter tube 104 by about 1.7 degrees so that the male Luer tip 110, when inserted into the catheter hub 102, is angled by the offset relative to the centerline of the distal portion of the catheter hub.

In other examples, the offset angle between the centerline of the distal portion of the catheter hub and the proximal portion of the catheter hub can be other than 1.7 degrees, such as 2 to 6 degrees offset. For a catheter hub with two centerlines with an offset angle of about 1.7 degrees, the catheter hub can be manufactured as a single hub body without resorting to two different hub sections or bodies that are separately manufactured and subsequently assembled. Thus, an aspect of the present disclosure is a tilted catheter hub having single body or hub having two different centerlines and wherein the two centerlines are angled relative to one another, also referred to as an offset angle or angular offset. In an example, the offset angle can be greater than 1 degree, such as 1.2 degrees, 1.5 degrees, or 1.7 degrees.

In some examples, the catheter hub with an angular offset, i.e., two different centerlines that are angled relative to one another, is usable with male Luer connectors with two different centerlines that are angled relative to another, as further discussed below. Alternatively, the catheter hub has a single centerline and is usable with a male Luer connector with two different centerlines that are angled relative to another, also further discussed below.

In some examples, the catheter hub 102 or the body 113 of the catheter hub 102 has a single centerline 101 and wherein the single centerline 101 of the catheter hub 102 is concentric with the centerline 103 of the male Luer tip 110 and the two components have a common centerline or an assembly centerline 130. Thus, although the catheter hub 102 of FIG. 1 is shown with an angular offset of about 1.7 degrees between the distal catheter portion and the proximal catheter hub portion, for purposes of the following discussions, the catheter hub 102 of FIG. 1 is assumed to have a single centerline 101, similar to the catheter hub 102 of FIG. 2, and the male Luer tip 110 of the male Luer connector 106 has a common centerline with the single centerline of the catheter hub 102.

As shown, the male Luer connector 106 has at least two centerlines that are angled relative to one another. For example, the tubing coupling 120 has a coupling centerline 136 that is angled from the common centerline 130, and therefore angled from the centerline of the catheter hub 102 and the centerline 103 of the male Luer tip 110. The offset angle α1 of the coupling centerline 136 can vary within a range of the common centerline 130. For example, the offset angle α1 can range from about 2 degrees to about 24 degrees. In other examples, the angle offset α1 can be greater than 24 degrees, such as 26 degrees or 32 degrees. Depending on the length of the tubing coupling 120 and the proximal edge 140 of the tubing coupling 120 relative to the skin 112, the angle can vary. In an example, for a given length, the offset angle α1 is about 24 degrees so that the proximal edge 140 can be angled towards the patient's skin 112 to within about a 2 mm gap, which may be referred to herein as a set gap 144. However, the offset angle α1, for a given length of the tubing coupling 120, can be selected so that the proximal edge 140 of the tubing coupling 120 touches the skin 112 or is spaced from the skin 112 by a different value for the set gap 144, such as 1 mm or greater than 2 mm, such as 3 mm, 4 mm, or greater.

In the example shown, the set gap 144, based on the length of the tubing coupling 120 and the offset angle α1, is 2 mm, plus or minus 1 mm. This dimension can be selected so that the IV tubing (now shown) that extends out from the proximal opening or female receptacle 148 of the tubing coupling 120 can project out a small distance before bending against the skin 112. Thus, in an example, the offset angle α1 can be selected so that the IV tubing connected to the tubing coupling can bridge the set gap 144 and provide support for the proximal end of the tubing coupling 120 and more broadly to the infusion system 100. The offset angle can be about 20 degrees to about 26 degrees and the set gap 144 can be about zero to about 4 mm. In other examples, the set gap 144 can be about 4.1 mm to about 7.5 mm. In still other examples, a support for the infusion system 100 at the proximal end of the infusion system can be provided by a center section of the infusion system, such as by the collar 108 of the male Luer connector 106 touching or resting against the skin 112, in addition to or alternative to the proximal edge 140 of the tubing coupling 120 or the IV tubing extending from the tubing coupling 120.

As shown, the collar 108 has internal threads 150 for threaded engagement with external threads 152 on the catheter hub 102. The collar 108 is preferably a spin type that is rotatable relative to the male Luer tip 110, as previously discussed. Less preferably, for the present embodiment, the collar 108 is a fixed collar and not rotatable relative to the male Luer tip. In the present embodiment, the spin lock collar 108 allows the tip 110 of the male Luer connector 106 to be inserted into the catheter hub 102 and the tubing coupling 120 angled so that the tubing extending from the male Luer connector is located next to the skin 112 and the set gap 144 is as small as possible before threading the collar 108 to the external threads 152, such as shown in the engaged position of FIG. 1. Thus the infusion system 100 allows the softer tubing to contact the skin 112 for a more patient friendly infusion.

Figure 2:
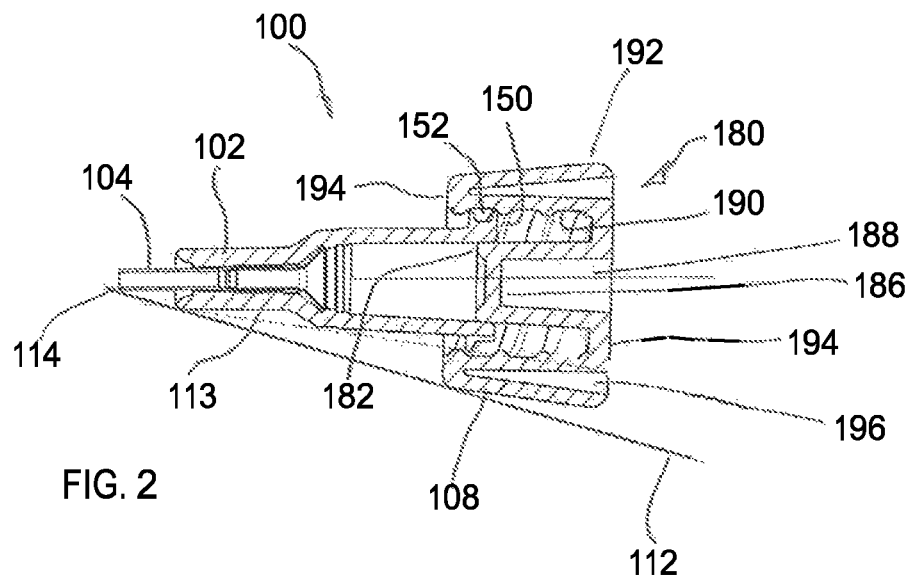
FIG. 2 is a schematic cross-sectional side view of an infusion system provided in accordance to a second aspect of the present disclosure.

In an example, the collar 108 has a body 158 comprising a distal end 160 and a proximal end 162. The body 158 of the collar, at least exteriorly, can be symmetrical about a collar centerline. When so practiced, the proximal end 162 of the collar 108 can be spaced from the skin 112 by a collar gap 166. In some examples, the body 158 of the collar 108 can be conically shaped so that the proximal end 162 of the body 158 is larger or wider than the distal end 160 of the body to take up some or all of the collar gap 166 with the skin 112, such as to close the gap with the skin or touch the skin with the proximal end of the collar. An exemplary conically shaped collar is shown in FIG. 2 and further discussed below. The conically shaped collar 108 may be molded as such or may be made as such by a separately formed elastic tapered cushion that is added to, such as placed around, the collar 108. The male connector and the catheter hub can be made from conventional materials such as ABS.

In an alternative embodiment, a grip impression may be incorporated to the exterior of the tubing coupling 120. For example, the tubing coupling 120 may be sufficiently thick and two diametrically opposed impressions or indentations are incorporated to the wall or body of the tubing coupling 120 to serve as gripping features. The two grip impressions will provide visual communication to a practitioner regarding where to grip the male Luer connector 106 when assembling the male Luer connector to the catheter hub 102.

In another alternative embodiment, a support feature may be added to the tubing coupling 120, with or without grip impressions. For example, the tubing coupling 120 may be formed with two wings extending laterally of the body of the tubing coupling 120. The wings can be flexible and/or pliable to yield when pressed against the skin 112. The support feature, such as wings, can be positioned at or near the proximal edge 140 of the tubing coupling 120 on the side of or near the set gap 144. When incorporated, the support feature helps to ensure placement or alignment of the proximal edge 140 of the tubing coupling 120 relative to the skin 112, such as to place the side of the tubing coupling with the support feature closer to the skin before threading the collar 108 to the catheter hub 102.

The infusion system 100 may be secured to the patient using an adhesive medical dressing, medical tape or combinations thereof and the offset angle α1 in the male Luer connector 106, formed by providing at least two centerlines at an angle relative to one another, allows the proximal end of the infusion system 100 to be positioned closer to the skin than a conventional infusion system without the offset angle α. This in turn allows the infusion system 100 to be secured to the patient with minimal or no set gap 144, or with a gap that is bridged by the IV tubing, to provide a stable system that reduces or eliminates any possibility of moving or disturbing the puncture site 114. In the embodiment shown, the two angled centerlines are incorporated by forming a male Luer tip 110 with a centerline and a tubing coupling 120 extending from the male Luer tip with a centerline that is angled to the centerline of the male Luer tip. This forms an angle offset within the male Luer connector thereby forming a tilted connector or tilted male Luer connector for minimizing the set gap 144 compared to when using a male Luer connector without the offset angle α.

Figure 1A:
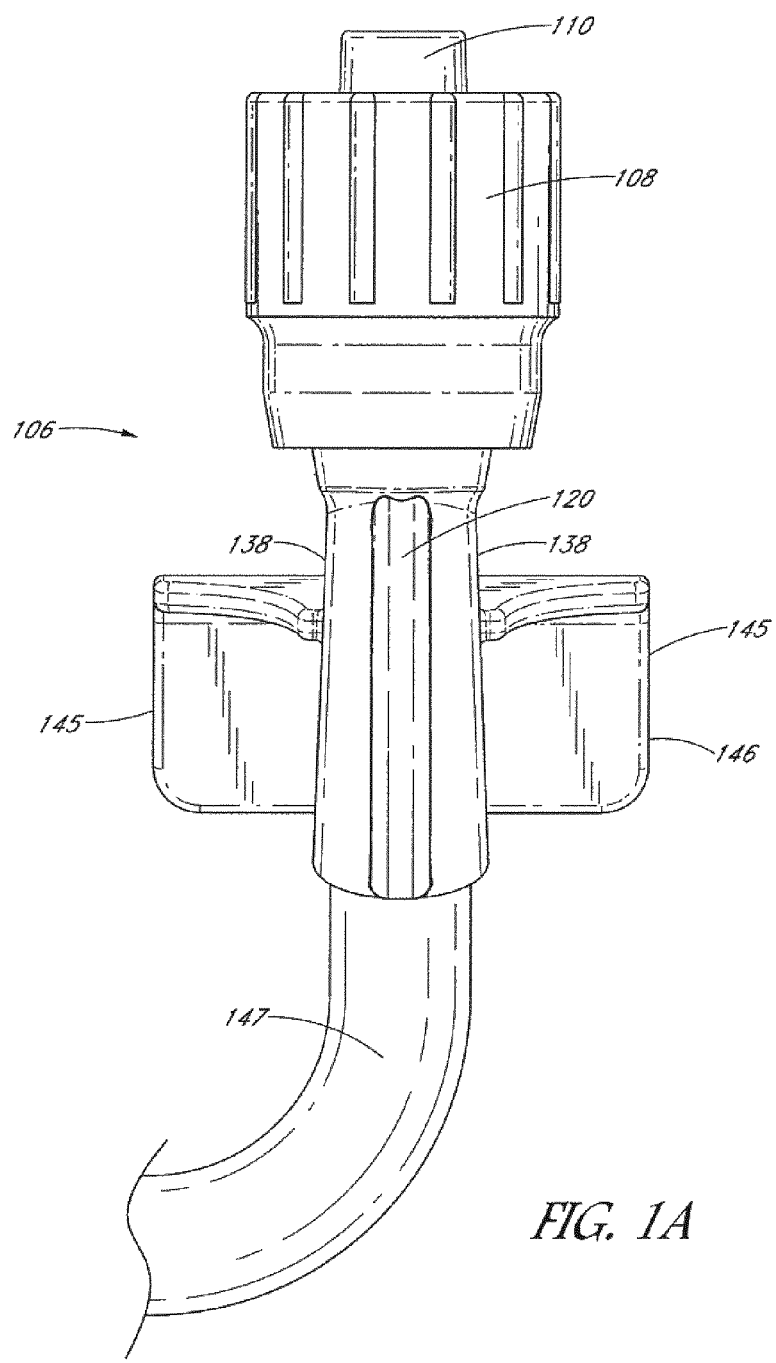
FIG. 1A is a schematic top plan view of a male Luer connector provided in accordance to a third aspect of the present disclosure and FIG. 1B is a cross-sectional side view of the male Luer connector coupled to a catheter hub.

FIG. 1A is a schematic drawing top view of a male Luer connector 106 in accordance with aspects of the present disclosure. The male Luer connector 106 has a male Luer tip 110, a tubing coupling 120, and a threaded collar 108. The threaded collar can be rotatable relative to the Luer tip or tubing coupling, and can be a spin lock collar. The male Luer connector 106 can embody a tilted connector in which the male Luer tip has a center line and the tubing coupling has a centerline and wherein the two centerlines are angled relative to one another by an offset angle, similar to the male Luer connector 106 of FIG. 1. As shown, the tubing coupling 120 has grip impressions 138 formed with the exterior of the tubing coupling. The grip impressions can be continuously formed around the entire circumference of the tubing coupling 120 or can be discontinuous, such as having two opposed impressions on different sides of a centerline.

A support feature 146 can be provided with the tubing coupling 120. As shown, the support feature 146 comprises two wings or flaps 145 extending from the tubing coupling. The support feature 146, such as wings, can be positioned at or near the proximal edge 140 of the tubing coupling 120 (FIG. 1) on the side of or near the set gap 144. Although the wings 146 are shown schematically to be as wide as the threaded collar 108, they can be made longer or shorter and can also have joints or weakened lines for adapting to the anatomical features of the back of the hand or arm. When incorporated, the support feature helps to ensure placement or alignment of the proximal edge 140 of the tubing coupling 120 relative to the skin 112, such as to place the side of the tubing coupling with the support feature 146 closer to the skin before threading the spin lock collar 108 to the catheter hub 102 (FIG. 1). An IV tubing 147 extends from the tubing coupling 120.

Figure 1B:
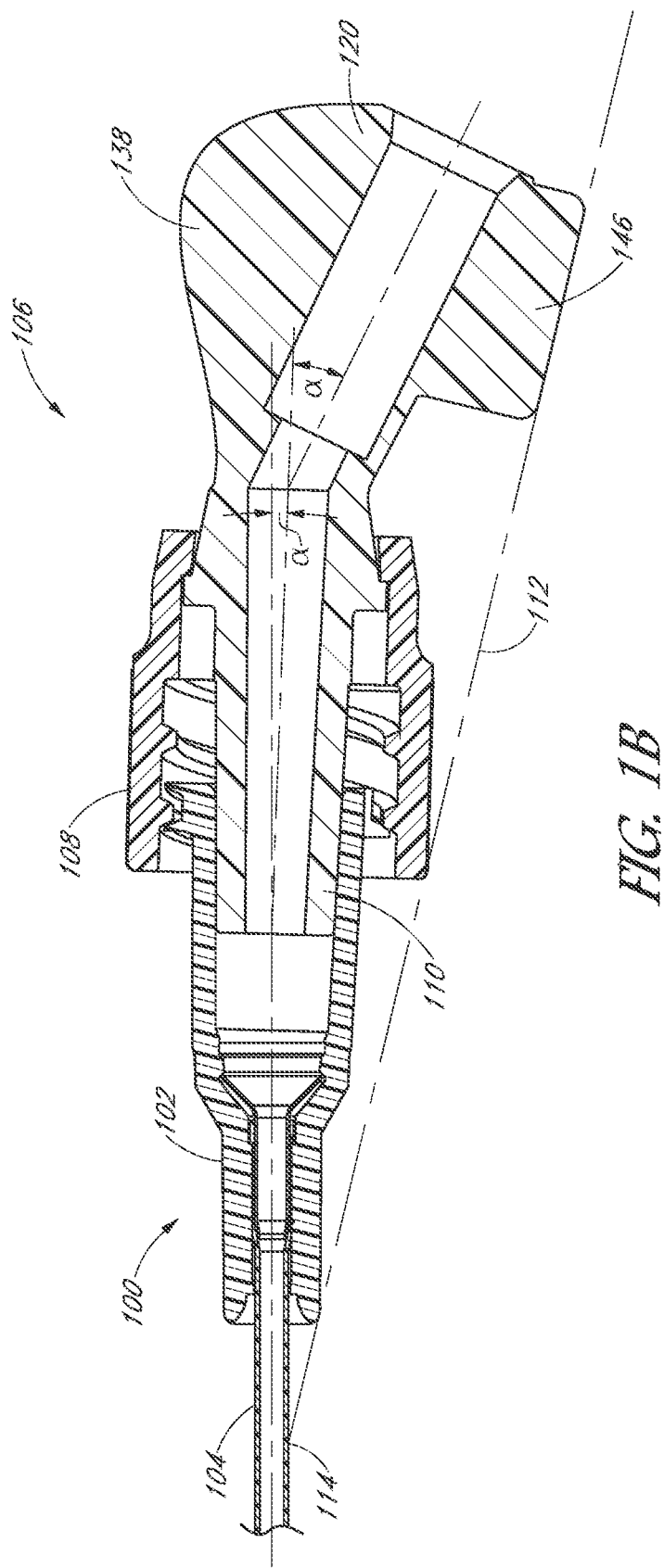

FIG. 1B is a cross-sectional side view showing an infusion system 100 comprising a catheter hub 102 coupled to a male Luer connector 106. The catheter hub 102 can be similar to the catheter hub of FIG. 1 comprising a catheter tube 104 penetrating a puncture site 114. The male Luer connector 106 can be similar to the male Luer connector of FIG. 1A, which comprises a spin lock collar 108 mounted about a male Luer tip 110 and having a tubing coupling 120 extending from the male Luer tip 110. The male Luer connector 106 is further shown with enlarged grip impressions 138 formed with the tubing coupling 120, such as by forming enlarged wall portions with indentations to serve as gripping means. The tubing coupling 120 can be connected to a tubing section or tubing line, which can be part of an extension set or an IV administration set, as previously discussed.

A support feature 146 is shown attached to the grip impressions 138, at a lower end to be placed adjacent the skin 112. The support feature 146 can embody wings 145 as previously discussed projecting outwardly from a lengthwise axis of the connector. The support feature 146 can be sized and shaped to contact the skin 112, such as to form a line contact with the skin. The shape of the grip impressions 138 and the location of the support feature 146 can provide visual indication or feedback for the user to orientate the tubing coupling 120 so that the support feature 146 faces or angles towards the patient 112 when inserting the male Luer tip 110 into the catheter hub 102 and before tightening the collar 108 to the catheter hub 102. The grip impressions 138 and the support feature 146 can be unitarily or co-molded to be part of the tubing coupling 120. In alternative examples, a separately formed adaptor having grip impressions and wings may be placed around a cylindrical tubing coupling 120 to provide the grip and support functions described herein. For example, an adaptor made from a rubber, plastic or silicone material having a bore can be provided and the cylindrical tubing coupling inserted into the bore of the adaptor. Optionally, the grip impressions and/or the wings can be omitted from the support feature or adaptor 146.

For a support feature 146 embodiment that is separately formed and attached to the tubing coupling 120 noted immediately above in the form of an adaptor, the separately formed adaptor can have a wedge like shape and placed in contact with the tubing coupling of a male Luer connector to support the tubing coupling against the skin, such as to take up the gap normally present between the skin and the tubing coupling. In other words, the separately formed adaptor having the wedge shape can take up the set gap 144 (FIG. 1) between the proximal edge 140 of the tubing coupling 120 and the skin 112 to provide a physical barrier between the two to support the male Luer connector from rocking up and down relative to the skin. The separately formed support adaptor can fit around the cylindrical tubing coupling 120 by forming a bore to receive the cylindrical tubing coupling 120. The structure of the separately formed adaptor can have a continuous body section defining the bore to receive the cylindrical tubing coupling 120. The continuous body section, as the phraseology implies, does not have any slit, gap, or slot to receive a tubing length from a side. As further discussed below, the tubing length needs to be routed through two openings of the support feature, via one of the two tubing ends, to connect to the support feature.

With reference now to FIG. 2, a male closing cap 180 comprising a male tip 182 and a collar 108 is coupled to the catheter hub 102. In particular, the male tip 182 is inserted into the open proximal end of the catheter hub 102 and the collar 108 is threadedly engaged to the external threads 152 of the catheter hub 102. The male tip 182 has a plug 186 for isolating the lumen 188 of the tip 182, which closes the open proximal end of the catheter hub 102 from fluid flow. As previously described and applicable elsewhere as here, the system 100 shown is understood to be in fluid communication with a patient, such as after removal of a needle and needle hub following successful venipuncture. As further discussed below, a needle guard can be incorporated so that when the needle is removed, the tip of the needle is guarded by the needle guard to prevent a needle stick injury.

As shown, the collar 108 is fixed to the male tip 182. The collar has an internal annular collar wall 190 and an external annular collar wall 192 connected to one another by a web 194. The male tip 182 and the internal annular collar wall 190 may be connected to one another by another web 194. Internal threads 150 are provided with the internal annular collar wall 190. A variable gap 196 is provided between the two walls 190, 192 to form a conically shaped external collar wall, conically shaped relative to a centerline of the male closing cap. The variable gap 196 may be selected to control the amount of taper, which can bridge or take up space between the collar 108 and the patient, as represented by the line 112. The conically shaped collar 108 may alternatively be tapered by providing a variable wall thickness on the exterior annular wall 192, such as providing the wall with increasing thickness in the proximal direction to form the conical shape. In other examples, the collar 108 has a single wall having both the internal threads 150 and wall (195) with a variable wall thickness to form the conically shaped collar body, as shown in FIG. 13.

Figure 13:
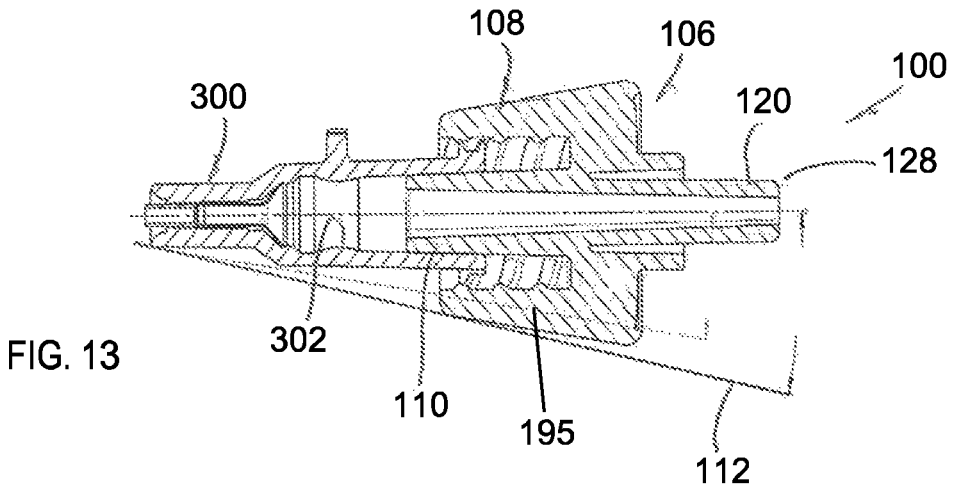
FIG. 13 is a schematic cross-sectional side view of an infusion system provided in accordance to a fourteenth aspect of the present disclosure.

In yet further embodiments, a spin lock collar 108 as in FIG. 1, which can rotate relative to the male Luer tip, can have a relatively constant or straight body as in FIG. 1 or a conically shaped body as described above and shown in FIG. 2 and elsewhere, such as FIG. 13.

As shown in FIG. 2, when the catheter tubing 104 is placed inside the vasculature of a patient and the catheter hub 102 is to be closed, such as to prevent outward blood flow from the catheter hub, the present male closing cap 180 with a conically shaped collar 108 is configured to block the proximal opening of the catheter hub, stabilize the catheter hub 102 by providing added surface contact between the collar 108 and the skin 112, and can stabilize the puncture site 114 to prevent unwanted movement or displacement of the catheter tube from the patient's vein. In some examples, the catheter hub 102 is a valved catheter hub comprising a valve that closes to restrict or prevent blood flow from flowing in the proximal direction out the catheter hub to provide time for a practitioner to close the proximal end with the male closing cap 180, such as the valved catheter hub of FIGS. 6 and 7.

Thus, a catheter hub having a body with two centerlines can include a first hub section with a centerline and a second hub section with a centerline and wherein the two centerlines of the first hub section and the second hub section are angled relative to one another. The first hub section and the second hub section can be singularly formed as a single hub body as shown or can be made from two hub bodies that are subsequently combined or joined, as discussed below with reference to FIGS. 3, 4, and 6-10.

Figure 3:
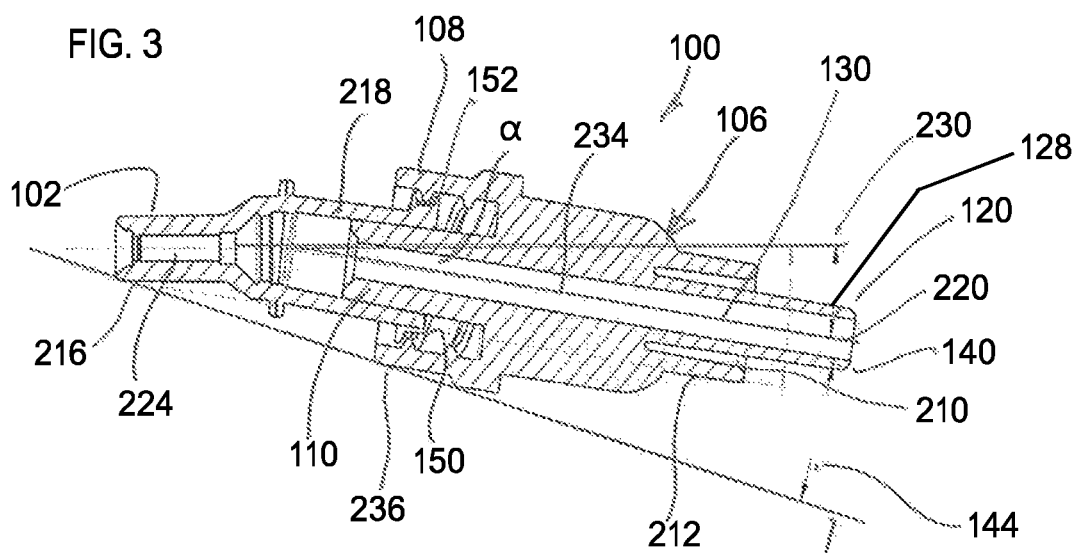
FIG. 3 is a schematic cross-sectional side view of an infusion system provided in accordance to a fourth aspect of the present disclosure.

With reference now to FIG. 3, an infusion system 100 comprising a catheter hub 102 and a male Luer connector 106 attached to the catheter hub is shown. The catheter hub 102 is shown without a catheter tube, which is understood to be part of the catheter hub 102 but not shown for clarity. In the present embodiment, the male Luer connector 106 has a collar 108 fixed to the male Luer tip 110. A tubing coupling 120 in the form of a male nipple 128 is provided at the proximal end of the connector for engaging the interior of an IV tubing, which can form part of a tubing line of an extension set. The IV tubing is configured to be wedged in the gap or annular space 210 in between the male nipple 128 and the tubing collar 212.

The catheter hub 102 shown is a two-part hub, which comprises a distal hub body or first hub body 216 attached to a proximal hub body or second hub body 218. The proximal hub body 218 has a female Luer taper and external threads 152 for threaded engagement with the internal threads 150 of the collar 108. The seam where the two hub sections or two hub bodies attach can be anywhere along an axial position of the catheter hub 102 distal of the Luer taper.

As shown, the distal hub body 216 has a centerline 224 and the proximal hub body 218 has a centerline, which are angled to one another. Thus, the catheter hub 102 is a tilted catheter hub in that the proximal hub body 218 is angled to the distal hub body 216 and the two hub sections have centerlines that are angled. Said differently, the catheter hub has two different hub sections with different centerlines having an offset angle α.

The male Luer connector 106 has a lengthwise axis that is generally straight and the lumen 220 is formed generally around a single centerline. Further, the centerline of the male Luer connector 106 and the centerline of the proximal hub body 218 are concentric and have a common centerline 130. The common centerline 130 and the centerline 224 of the distal hub body 216 are angled to one another. Consequently, where the entire infusion system 100 normally has a system centerline 230 that is coincident with the centerline 224 of the distal hub body 216, in the present embodiment, by incorporating a tilted catheter hub, there are at least two centerlines that are angled to one another. In particular, the centerline 224 of the distal hub body 216 and the common centerline 130 of the proximal hub body 218 and the male Luer connector 106 are angled to another. By angling the proximal hub body 218 relative to the distal hub body 216, the male Luer connector 106 is shifted by the angle offset towards the skin. In particular, the proximal edge 140 of the tubing coupling 120 is moved closer to the patient's skin 112 such that the set gap 144 measured between the proximal edge 140 and the skin 112 is reduced compared to similar catheter assemblies with hub bodies that are not tilted or not angled relative to one another.

In an example, the centerline 234 of the proximal hub body 218 can be angled about 5 degrees to about 10 degrees relative to the centerline 224 of the distal hub body 216. In a particular embodiment, the angular offset of the two centerlines 224, 234 between the two hub bodies 216, 218 is about 8 degrees. For a particular length and an angle offset between the two centerlines 224, 234 of about 8 degrees, the proximal edge 140 on the tubing coupling 120 from the skin 112, i.e., the set gap 144, can be reduced from about 15 mm with no angular offset to about 7 mm. In other examples, the set gap 144 can be smaller than 7 mm, such as 2 mm or 4 mm. The set gap 144 can be made smaller or larger by varying the angular offset and dimensions of the various components, as further discussed below. Thus, aspects of the present disclosure is understood to include a catheter hub, a connector, or both having an offset angle so that the set gap can be reduced compared to similar components without the disclosed angle offset. The angle offset can be in the catheter hub only, the male connector only, or both.

An aspect of the present disclosure is further understood to include an apparatus and a system for providing support for a male Luer connector 106 connected to a catheter hub 102. In an example, the support for the male Luer connector 105 can comprise a structure for bridging a gap between a proximal end of the male Luer connector, such as the proximal end of the tubing coupling 120, and the patient's skin 112. By taking up this gap with a physical barrier, the male Luer connector 106, which can connect to a catheter hub, can be kept from rocking up and down relative to a surface, such as relative to a patient's skin.

The physical barrier can be called a support feature, structure, or adaptor, which can be used interchangeably. The support feature can comprise forming a catheter hub with at least two sections having two different centerlines that are offset by an offset angle α so that together with a tubing length can provide the physical barrier. The support structure can alternatively be a male Luer connector with at least two sections having two different centerlines that are offset by an offset angle α1 so that together with a tubing length can provide the physical barrier. The support structure can be in the form of a body having a wedge shape adaptor to support the male Luer connector. The body with the wedge shape can be unitarily formed with the male Luer connector or separately formed and subsequently coupled to the male Luer connector. Still alternatively, the support feature can comprise a combination features noted immediately herein.

In some examples, a male Luer connector and/or a support feature can be part of an extension set or an IV administrative set. The support feature can be integral with a male Luer connector or separate from the male Luer connector. For example, a collar for use with a male Luer tip can have a conical or wedge shape to take up a set gap between the skin and a proximal end of the male Luer connector, as discussed above with reference to FIG. 3. Alternatively, the collar can be a straight collar and a separate adaptor having a ramp or wedge shape is placed between the collar and the skin, as further discussed below and discussed above with reference to FIG. 1B. If a tubing coupling of a male Luer connector extends proximally of a collar, then the support in the form of an adaptor can be attached to the tubing coupling to support the male Luer connector against the skin.

An aspect of the present disclosure therefore can include a method for stabilizing a puncture site 114 having a catheter tube 104 penetrated therethrough, wherein the method can comprise maintaining a male Luer connector 106 at a position relative to the skin of a patient so that the catheter tube 104 is not kinked or bent to restrict flow by more than 20% compared to when the catheter tube is not kinked or bent. The method can comprise using one or more of the support features or structures noted herein.

The angular offset or offset angle α between the two hub sections of the catheter hub (e.g., by utilizing a tilted catheter hub) and a tapered collar can be incorporated so that the collar 108 can be devised to make a line contact 236, or at least more than a point contact, with the skin 112 to provide support for the infusion system at the collar. In the example shown in FIG. 3, the collar 108 is generally constant or straight. In other examples, the exterior profile of the collar 108 can be tapered, such as conically shaped, to improve the surface contacts with the skin 112 to thereby support the infusion system by providing a larger contact surface with the skin compared to a single point contact or a small line contact when the collar is not tapered and/or when an angular offset is not utilized.

Figure 4:
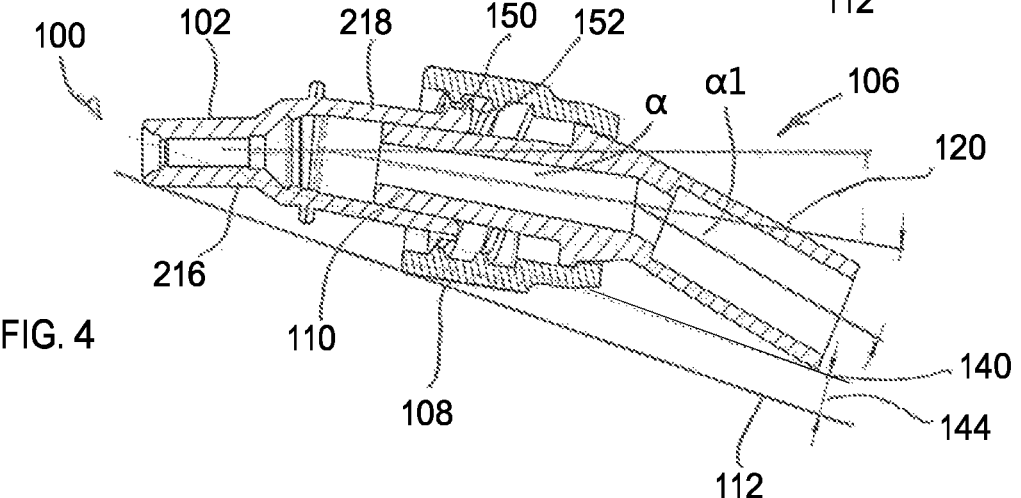
FIG. 4 is a schematic cross-sectional side view of an infusion system provided in accordance to a fifth aspect of the present disclosure.

FIG. 4 is a cross-sectional side view of yet another infusion system 100 provided in accordance with aspects of the present disclosure. The present infusion system 100 is similar to a combination of the systems of FIG. 1 and FIG. 3. As shown, the catheter hub 102 is a tilted catheter hub and comprises a distal hub body 216 and a proximal hub body 218. The male Luer connector 106 is similar to the male Luer connector of FIG. 1. Thus, the present embodiment utilizes a spin lock collar 108 that is rotatable around a male Luer tip 110. Other variables described with reference to the male Luer connector 106 of FIG. 1 are applicable to the present embodiment.

Figure 5:
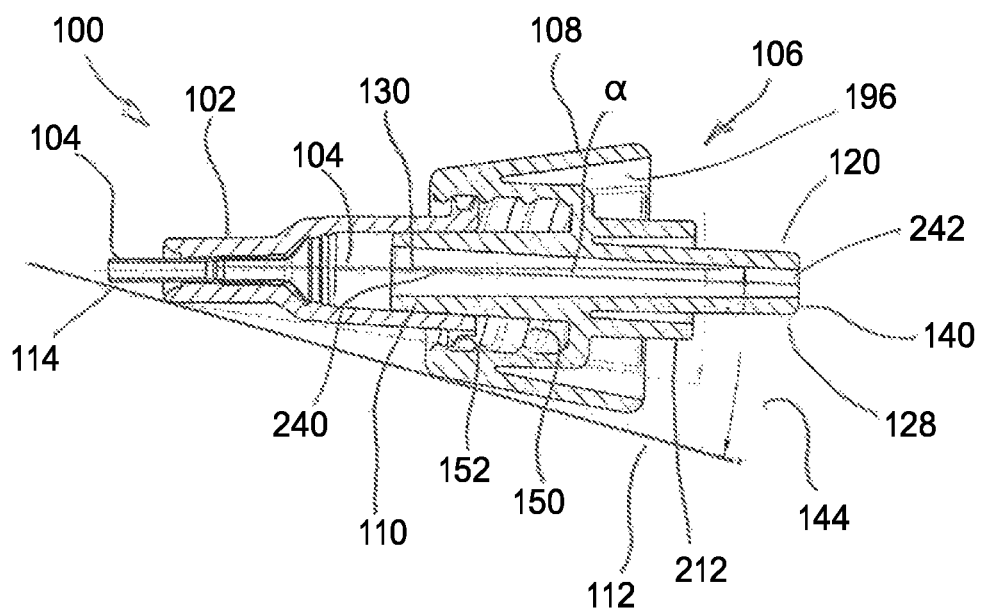
FIG. 5 is a schematic cross-sectional side view of an infusion system provided in accordance to a sixth aspect of the present disclosure.

FIG. 5 is a cross-sectional side view of yet another infusion system 100 provided in accordance with aspects of the present disclosure. The present infusion system 100 is similar to a combination of the systems of FIG. 1, FIG. 2, and FIG. 3. As shown, the catheter hub 102 can be a standard one-piece hub body with two centerlines 101, 240 that are angled relative to one another. For example, the centerline 101 of the distal portion of the catheter hub 102 can be angled relative to a second centerline 240 at the proximal portion of the catheter hub 102, similar to that shown in FIG. 1. As shown, the angular offset between the two centerlines is about 1.7 degrees with other angles contemplated. Thus, the catheter hub 102 can be considered a tilted catheter hub 102 in that the catheter hub has two centerlines that are angled relative to one another. The catheter hub 102 can be used with a male Luer connector 106 with a single centerline or one that is also tilted, such as having two different centerlines that are angled relative to one another. For example, the male Luer connector 106 can be tilted as shown in FIG. 1 and incorporates a conically shaped collar 108, similar to the collar of FIG. 2. The tubing coupling 120 can embody a male nipple 128, similar to the embodiment of FIG. 3. The collar 108 is shown fixed to the male Luer tip 110 but may be a spin lock-type collar that can rotate relative to the male Luer tip 110.

In the present embodiment, the male Luer tip 110 is concentric with the proximal hub portion of the catheter hub 102 and the centerline 240 of the proximal portion shares a common centerline 130 with the centerline of the male Luer tip 110. The common centerline 130 can be angled to the centerline 101 of the distal portion of the catheter hub. Alternatively, the male nipple 128 of the tubing coupling 120 can have a centerline that is angularly offset from the common centerline 130 to tilt the proximal edge 140 of the male Luer connector 106 closer to the skin 112, by reducing the set gap 144 compared to similar components without any angular offset. The angular offset can range from about 4 degrees to about 10 degrees. As shown, the angular offset between the centerline 242 of the male nipple 128 and the common centerline 130 is about 1.7 degrees. In this embodiment the collar 108 is set to match the skin line 112 as close as possible and the variable gap 196 can be adjusted to produce a tapering shape to match the skin line.

Similar to the embodiment of FIG. 1B, a separately formed support feature 146 can be attached to the tubing coupling 120 instead of or in addition to utilizing a wedge shaped collar 108. The separately formed adaptor can have a wedge like shape and placed in contact with the tubing coupling 120, and/or against the collar 108, to support the tubing coupling against the skin, such as to take up the gap normally present between the skin and the tubing coupling. In other words, the separately formed adaptor having the wedge shape can take up the set gap 144 (FIG. 1) between the proximal edge 140 of the tubing coupling 120 and the skin 112 and functions as a physical barrier between the two. The separately formed adaptor can fit around the cylindrical tubing coupling 120 by forming a bore to receive the cylindrical tubing coupling 120. The structure of the separately formed adaptor can have a continuous body section defining the bore to receive the cylindrical tubing coupling 120 via projecting an end of the tubing line through an opening at the two ends of the bore.

Figure 6:
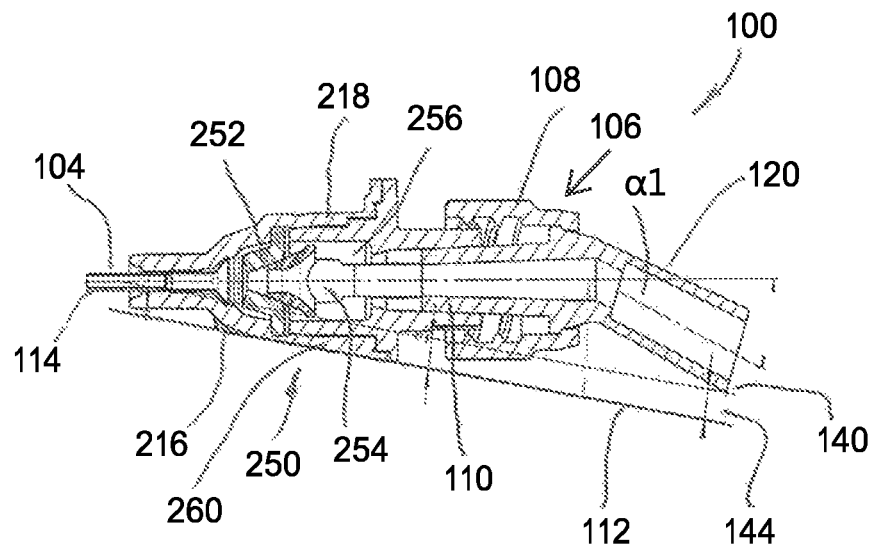
FIG. 6 is a schematic cross-sectional side view of an infusion system provided in accordance to a seventh aspect of the present disclosure.

With reference now to FIG. 6, an alternative infusion system 100 comprising a valved catheter hub 250 having a valve 252 located inside a two-part hub body is shown, which comprises a first hub body 216 and a second hub body 218. The catheter hub 250 is shown with a catheter tube 104 placed in a patient's vasculature at a puncture site 114, as previously discussed, such as following successful venipuncture and a needle and needle hub removed from the catheter hub and catheter tube. A valve opener or valve actuator 254 is slidably disposed in the interior cavity 256 of the catheter hub 250 and is pushed distally into the valve 252 by the male Luer tip 110 of the male Luer connector 106 to open the valve 252. Aspects of the valve 252 and valve opener 254 are further described in U.S. Pat. No. 8,333,735, the contents of which are expressly incorporated herein by reference. In an alternative embodiment, the catheter hub 250 is a singularly formed unit having a single hub body without any parting line. The valve 252 can be placed inside the interior of the single hub body and held therein using a groove with one or more shoulders.

A needle guard or tip protector may be incorporated with the catheter hub 250 and removed by the needle, and covers the needle tip, when the needle is removed following successful venipuncture. The needle guard can be configured to cooperate with a bump or a crimp, such as a change in profile, on the needle. For example, the change in profile can abut a perimeter defining an opening on a proximal wall of the needle guard to retract the needle guard out from inside the interior cavity of the catheter hub following successful venipuncture. The needle guard or tip protector is also described in the '735 patent. Exteriorly, a pair of wings 260 (shown only in cross section) may be incorporated to a lower section of the hub body to facilitate securing the catheter hub 250 to the patient.

The male Luer connector 106 has a male Luer tip 110, a tubing coupling 120, and a spin lock collar 108, similar to the male Luer connector 106 discussed with reference to FIG. 1. Thus, the proximal edge 140 of the tubing coupling 120, which can connect to a tubing section of an extension set or an IV administrative set, is angled towards the skin 112 and the set gap 144 is reduced compared to a similar infusion system but wherein no offset angle is incorporated between the axis or centerline of the male Luer tip 110 and the centerline of the tubing coupling 120. This allows an IV tubing (not shown) connected to the tubing coupling 120 of the male Luer connector 106 to be curved or slightly bent against the skin 112 to support the proximal end of the infusion system 100 from rocking or swaying, which can cause the catheter tube 104 to retract or move within the puncture site 114. In an example, the set gap 144 can be set by an angular offset of at least two different centerlines of at least two different sections of the infusion system 100 of FIG. 6. The set gap 144 can be about 2 mm to about 6 mm with other ranges from zero to 7.5 mm contemplated.

Like the embodiment of FIG. 5, a separately formed support 146 can attach to the tubing coupling 120 instead of or in addition to utilizing a conical shaped collar 108. Further, the separately formed support 146 can be an adaptor that fits around the tubing coupling 120, which can connect to a tubing of an extension set or an IV admin set, to support the tubing coupling. The collar 108 can have a conical shape or can be a standard straight collar without a variable wall thickness or a variable gap. The separately formed support 146, which can comprise a structure having a bore and a ramp or wedge shape body section for supporting the tubing coupling 120, can be utilized with any of the male Luer connectors 106 discussed elsewhere herein.

Figure 7:
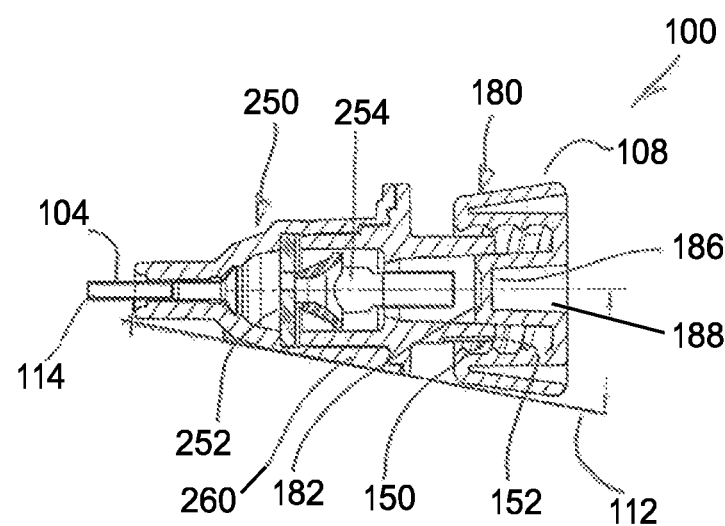
FIG. 7 is a schematic cross-sectional side view of an infusion system provided in accordance to an eighth aspect of the present disclosure.

With reference now to FIG. 7, an infusion system 100 comprising a male closing cap 180 comprising a male tip 182 and a conically shaped collar 108 is coupled to the catheter hub 250. In particular, the male tip 182 is inserted into the open proximal end of the catheter hub 250 and the internal threads 152 of the collar 108 are threadedly engaged to the external threads 150 of the catheter hub 250. The male tip 182 has a plug 186 for isolating the lumen 188 of the tip 182, which closes the open proximal end of the catheter hub 250. In an example, the catheter hub 250 can be similar to the catheter hub of FIG. 6 and the male closing cap 180 can be similar to the male closing cap of FIG. 2. By incorporating the conically shaped collar 108 with the valved catheter 250, the collar 108 can touch the skin 112 and support the proximal end of the infusion system 100 from rocking or swaying. Note that the tip of the male closing cap seals the open proximal end of the catheter hub but is sufficiently short so as not to push the valve actuator to open the valve 252. The valve 252 is shown in a closed position.

Figure 8:
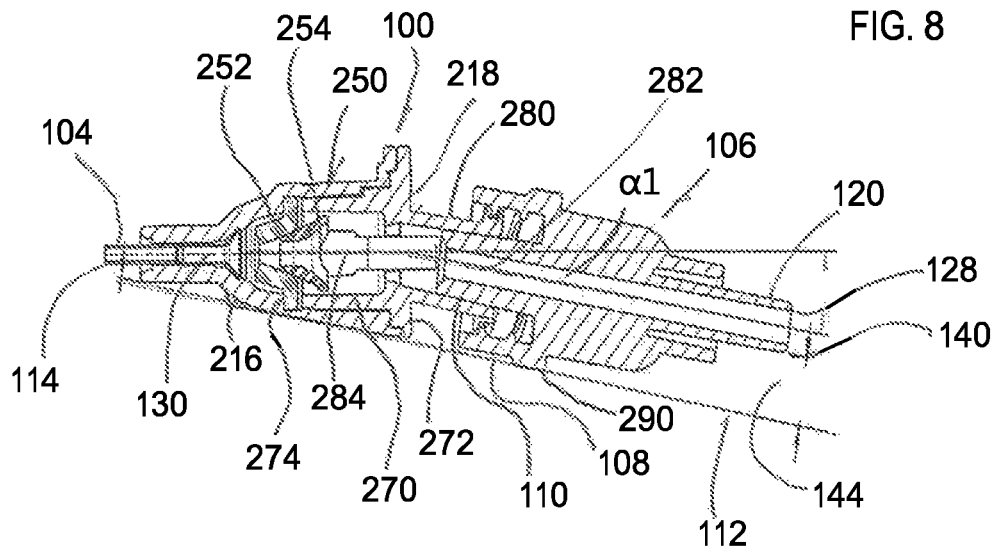
FIG. 8 is a schematic cross-sectional side view of an infusion system provided in accordance to a ninth aspect of the present disclosure.

FIG. 8 shows an infusion system 100 comprising a catheter hub 250 coupled to a male Luer connector 106, which can be similar to the male Luer connector of FIG. 3. The catheter hub 250 is a valved type, similar to the catheter hub of FIG. 6. However, in the present embodiment, the catheter hub is a tilted hub in which the first hub body 216 has a centerline and the second hub 218 has a second centerline and wherein the two centerlines are angled from one another. In an example, the second hub section 218 has a cylinder section 270 extending distally of a flange 272. The cylinder section 270 is configured to project into the bore of the first hub body 216. In an example, the projection into the first hub body 216 is configured to hold or retain a valve 252 between the distal end of the cylinder section 270 and an internal shoulder 274 inside the first hub body 216.

The second hub body 218 further comprises a female hub section 280 comprising a female Luer for receiving a male Luer tip 110 of the male Luer connector 106, which is received with the female Luer and pushes the valve actuator or opener 254 distally forward to open one or more flaps on the valve 252 to open a fluid flow path through the valve. As shown, the female hub section 280 has a centerline 282 that has been angled or tilted from the centerline 284 of the cylinder section 270. The centerline 284 of the cylinder section 270 is concentric with the centerline of the first hub section 216. In other words, the cylinder section 270 and the first hub section 216 have a common centerline 130. The offset angle between the two centerlines 282, 284 of the second hub body 218 may be formed by using two different core pins. The offset angle α between the two centerlines 282, 284 can be about 8 degrees with a range of 1.7 to 24 degrees contemplated. For example, if a smaller offset is desired, the offset angle α can be set to about 1.7 degrees as an example. If a larger offset is desired, the offset angle α can be set to about 24 degrees. Thus, the catheter hub 250 is understood to be a tilted hub having two different centerlines that are angled relative to one another by an offset angle α.

In the example shown, when the male Luer connector 106 is connected to the catheter hub 250, the proximal edge 140 of the male nipple 128 is angled towards the skin 112 due to the offset angle α incorporated by the tilted catheter hub 250. This angling of the proximal edge 140 towards the skin 112 establishes a set gap 144 measured between the proximal edge 140 and the skin 112 that is smaller in value than a comparable infusion device 120 in which no offset angle α within the catheter hub is employed. As shown, the set gap 144 is about 4.3 mm for a given length of infusion device 100 and for a given offset angle of about 8 degrees. In other examples, the set gap 144 can be smaller than 4.3 mm, such as 2 mm, and the offset angle can be larger than 8 degrees. The tilted catheter hub 250 allows the shoulder 290 on the male Luer connector 106 to rest against the skin 112 and provides another support point for the proximal end of the infusion system 100.

Additionally or alternatively, a separately formed support 146, as described above with reference to FIG. 1B, can attach to the tubing coupling 120 instead of or in addition to utilizing the angular offset of FIG. 8. Further, the separately formed support 146 can fit around the tubing coupling 120, which can connect to a tubing of an extension set or an IV admin set, to support the tubing coupling. The separately formed support 146 can also support the collar 108, which can be a conventional straight collar without a variable wall thickness or a variable gap or a collar with a conical shape. The separately formed support 146 can embody an adaptor and can comprise a structure having a bore and a ramp or wedge shape body section for supporting the tubing coupling 120 and can be used with various male Luer connectors 106 discussed elsewhere herein.

Figure 9:
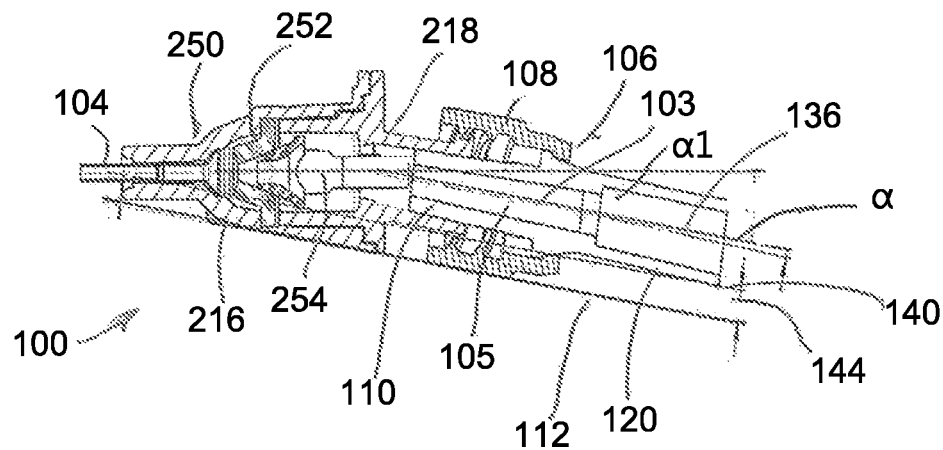
FIG. 9 is a schematic cross-sectional side view of an infusion system provided in accordance to a tenth aspect of the present disclosure.

FIG. 9 shows yet another infusion system 100 in accordance with aspects of the present disclosure. The system 100 comprises a catheter hub 250 and a male Luer connector 106 coupled to the catheter hub. The catheter hub 250 can be a tilted hub type similar to the catheter hub of FIG. 8. The male Luer connector 106 can be similar to the male Luer connector of FIG. 1 comprising a spin lock collar 108 located around a male Luer tip 110 and distal of a tubing coupling 120. However, the angle offset α1 between the centerline 103 of the male Luer tip 110 and the centerline 136 of the tubing coupling 136 in the present embodiment is smaller compared to the angle offset of the male Luer connector 106 of FIG. 1. In the present embodiment, the angle offset is about 1 to about 3 degrees. By incorporating the angle offset, the proximal edge 140 of the tubing coupling 120 is moved closer to the skin 112 and the set gap 144 is reduced compared to similar infusion systems having no offset angle or only a tilted catheter hub but not also a tilted male Luer connector with an offset angle. The set gap 144 in the present embodiment is about 2 mm when the offset angle of the tilted catheter hub is about 8 degrees and the offset angle of the male Luer connector is about 1.5 degrees. In other examples, the set gap can have a different value and the offset angle of the tilted catheter hub and the tilted male Luer connector can be different. Thus, the present embodiment has two angular offsets, one between two different centerlines of the catheter hub 250 that are angled to one another and the other between two different centerlines of the male Luer connector 106 that are angled to one another.

Figure 10:
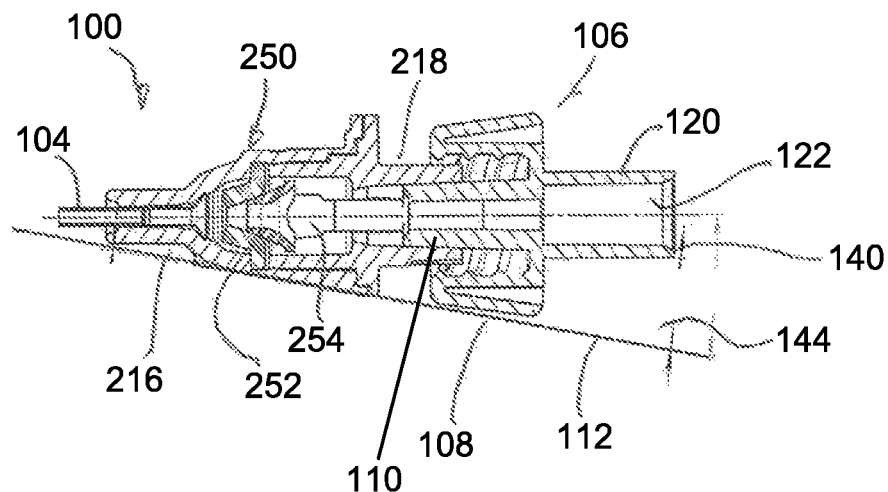
FIG. 10 is a schematic cross-sectional side view of an infusion system provided in accordance to an eleventh aspect of the present disclosure.

FIG. 10 shows an infusion system 100 in accordance with further aspects of the present disclosure. The system 100 comprises a catheter hub 250 and a male Luer connector 106 coupled to the catheter hub. The catheter hub 250 of the present embodiment can be similar to the valved catheter hub 250 of FIG. 6. The male Luer connector 106 of the present embodiment is similar to the male Luer connector 106 of FIG. 5 except the tubing coupling 120 is a female type receptacle comprising a bore or slot 122 for receiving an end of a tubing (not shown), which can be part of an IV administrative set or an extension set. The collar 108 shown is a fixed collar and does not spin or rotate relative to the male Luer tip 110, although such spin lock collar can be incorporated. In the present embodiment, the collar 108 is conically shaped, as discussed with respect to the collar of FIG. 2. As shown, the exterior of the collar 108 contacts the skin 112 and provides another support surface for the infusion system and supports, at least in part, the proximal edge 140 from rocking or swaying. The set gap 144 is shown with about a 5 mm to 6 mm gap between the proximal edge 140 and the skin 112. In other examples, an offset angle can be incorporated with the catheter hub 250, the male Luer connector 106, or both to reduce the set gap 144 to about 2 mm.

Figure 11:
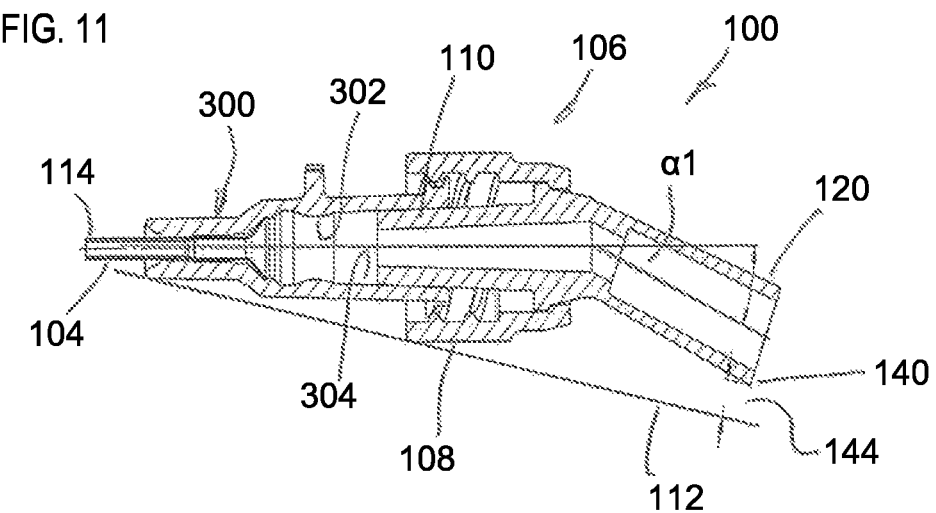
FIG. 11 is a schematic cross-sectional side view of an infusion system provided in accordance to a twelfth aspect of the present disclosure.

FIG. 11 shows an infusion system 100 in accordance with further aspects of the present disclosure. The system 100 comprises a catheter hub 300 and a male Luer connector 106 coupled to the catheter hub. The present catheter hub 300 is somewhat similar to the catheter hub 102 of FIG. 2 with a single centerline and with the exception of an internal change in profile 302 to the interior wall surface 304 of the catheter hub 300. The internal change in profile 302 can be a projection or a recess or a projection adjacent a recess and may be incorporated as a guard engagement surface for engaging a tip protector or a needle guard. The internal change in profile 302 can resemble a surface projection or recess in a catheter hub described in U.S. Pat. No. 8,382,721 for engaging a tip protector. The '721 patent is incorporated herein by reference to teach a needle guard and means for engaging the needle guard inside the catheter hub. The catheter hub 300 shown can be a single hub body, without a seam.

The male Luer connector 106 of FIG. 11 can resemble the male Luer connector of FIG. 1. Further, the spin lock collar 108 can incorporate a conically shaped outer contour to provide a greater surface contact with the skin 112, such as a tangential contact, as opposed to a point contact or a short line contact shown.

Figure 12:
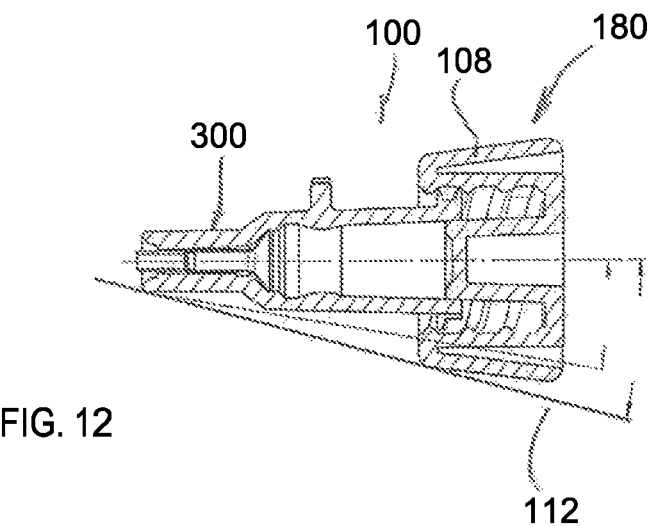
FIG. 12 is a schematic cross-sectional side view of an infusion system provided in accordance to a thirteenth aspect of the present disclosure.

FIG. 12 shows an infusion system 100 in accordance with further aspects of the present disclosure. The system 100 comprises a catheter hub 300 and a male closing cap 180 coupled to the catheter hub 300. The present catheter hub 300 is similar to the catheter hub of FIG. 11. The present male closing cap 180 can be similar to the male closing cap of FIG. 2. The angle of the collar 108 can be increased to be tangential with the skin line 112.

FIG. 13 shows an infusion system 100 in accordance with further aspects of the present disclosure. The system 100 comprises a male Luer connector 106 coupled to the catheter hub 300. The present catheter hub 300 is similar to the catheter hub of FIG. 11. The present male Luer connector 106 can be similar to the male Luer connector of FIG. 5 and comprises a male nipple 128. In the present embodiment, the collar 108 has a solid wall surface without a variable gap 196 for forming the tapered surface of the conically shaped collar. The conically shaped collar is configured to contact the skin 112 with a line contact as opposed to a single point contact or a small line contact so as to provide a more stable support system for the infusion system 100.

Figure 14:
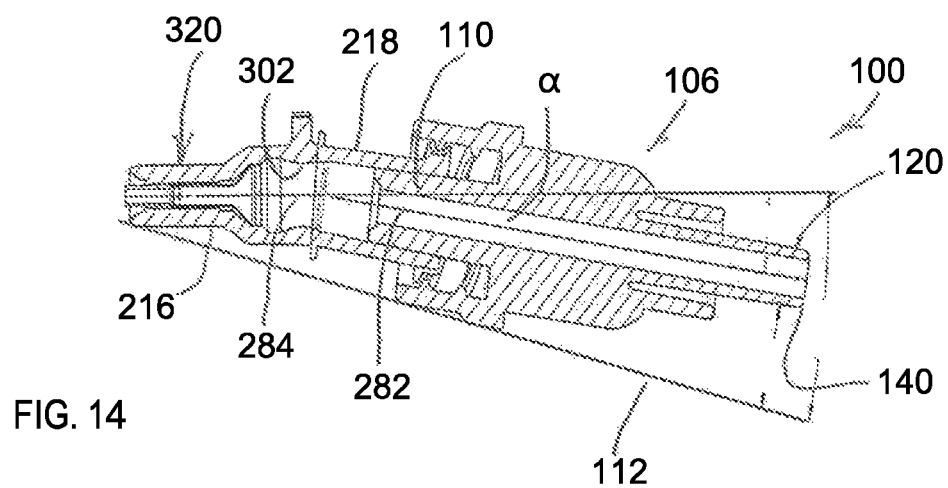
FIG. 14 is a schematic cross-sectional side view of an infusion system provided in accordance to a fifteenth aspect of the present disclosure.

FIG. 14 shows an infusion system 100 in accordance with further aspects of the present disclosure. The system 100 comprises a male Luer connector 106 coupled to the catheter hub 320. The present catheter hub 320 is somewhat similar to the catheter hub 300 of FIG. 11 except that the present hub incorporates an offset angle and is therefore a tilted catheter hub. In an example, the catheter hub 320 comprises a first hub body or section 216 joined to second hub body or section 218. The first hub body 216 can have a centerline 284 and the second hub body 218 can have a centerline 282 that is angled to one another such that the two centerlines have an offset angle α between them. In an example, the two hub sections can be joined at or near the internal change in profile 302. In the present embodiment, the second hub body 218 incorporate a separate Luer hub, as shown with reference to the multi-part hub of FIG. 3.

The catheter hub 320 is configured for use with a tip protector or needle guard, similar to the catheter hub 300 of FIG. 11. In other words, a needle guard is configured to engage with the internal change in profile 302 of the catheter hub and to be pulled or retracted by a change in profile on a needle following successful venipuncture.

The male Luer connector 106 of the present embodiment is similar to the male Luer connector of FIG. 3.

Figure 15:
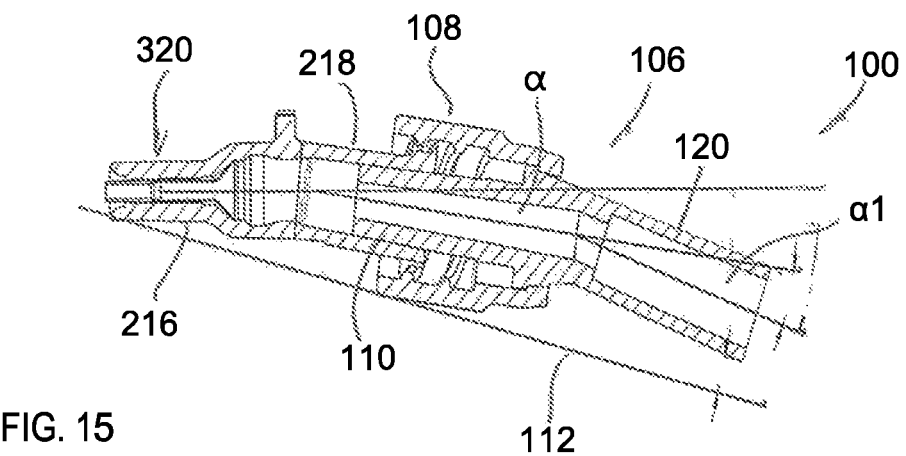
FIG. 15 is a schematic cross-sectional side view of an infusion system provided in accordance to a sixteenth aspect of the present disclosure.

FIG. 15 shows an infusion system 100 in accordance with further aspects of the present disclosure. The system 100 comprises a male Luer connector 106 coupled to the catheter hub 320. The present catheter hub 320 is similar to the catheter hub of FIG. 14. The present male Luer connector 106 can be similar to the male Luer connector of FIG. 3 and comprises a spin lock collar 108. Due to the catheter hub 320 being tilted, the angle offset of the male Luer connector 106 can be less than that of the male Luer connector of FIG. 4 and the spin lock collar 108 is more tangentially aligned with the skin line 112. Thus, the present embodiment has two angular offsets, one between two different centerlines of the catheter hub 320 that are angled to one another and the other between two different centerlines of the male Luer connector 106 that are angled to one another.

Figure 16:
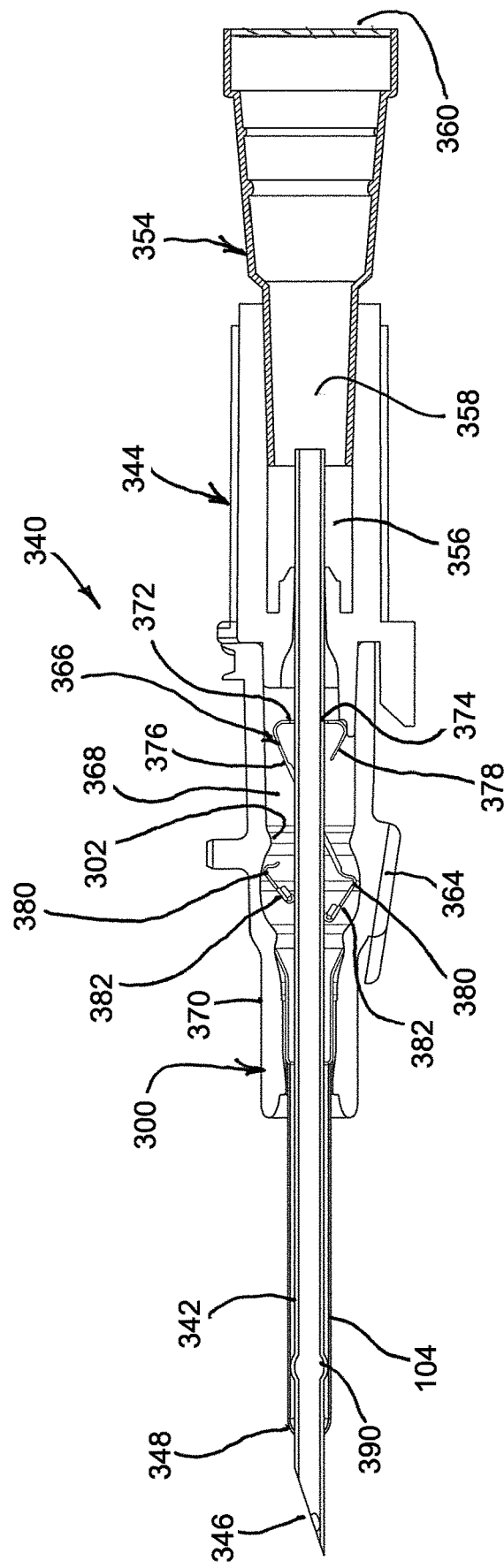
FIG. 16 is a cross-sectional side view of a catheter assembly usable with the extension set and IV administration set of the present disclosure.

With reference now to FIG. 16, a catheter assembly 340 is shown comprising a catheter hub 300, a catheter tube 104 extending distally of the catheter hub 300, a needle 342 extending distally of a needle hub 344 and through the catheter tube 104 such that a needle tip 346 extends distally of a distal opening 348 of the catheter tube 104. A pair of wings 364 can extend laterally of the catheter hub 300 to provide comfort and additional surfaces for securing the catheter hub 300 to the patient following placement of the catheter tube 104 into the patient's vasculature.

A flashback plug or blood stopper assembly 354 can be connected to the needle hub 344 to stop blood flow out the flashback chamber 356 of the needle hub 344. The flash back plug 354 can be provided at the proximal end the needle hub 344 to allow air to vent but stops blood from spilling out the proximal end of the body of the flash back plug 354, which has a chamber 358 and a hydrophobic filter 360 is assembled in the chamber.

A needle guard or tip protector 366 can be incorporated and can be located in the interior cavity 368 of the hub body 370 in the ready to use position of FIG. 16, which has the needle tip extending distally of the distal opening of the catheter tube. The needle guard 366 can have a proximal wall 372 with a perimeter 374 defining an opening having the needle passing therethrough. Two arms 376, 378 can extend distally of the proximal wall 372 and each comprising an elbow 380 located distally of the change in profile 302 inside the interior of the hub body 370. Placement of the elbows 380 distally of the change in profile 302 prevents the needle guard 366 from moving in the proximal direction during retraction of the needle 342 following successful venipuncture until the needle tip 346 moves proximally of the two distal walls 382 at the ends of the two arms 376, 378.

Upon moving proximally of the two distal walls, the two arms can move radially to reduce the radial profile of the needle guard at the two elbows 380. Once the radial profile of the needle guard 366 is reduced and is sufficiently smaller than the bore diameter of the interior cavity 368 at the change in profile 302, the needle guard 366 can move in the proximal direction when pulled proximally by the change in profile 390 on the needle 342, which can comprise a crimp, a bulge, a material buildup, a sleeve, or combinations thereof, abutting the proximal wall 372 at the perimeter 374. As the needle 342 retracts in the proximal direction away from the catheter hub 300, the change in profile 390 can pull the needle guard 366 in the proximal direction out the catheter hub.

In some examples, a valve and a valve opener, such as the valve 252 and valve opener 254 of FIGS. 6-10, can be located inside the catheter hub 300 of FIG. 16, as described in U.S. Pat. No. 8,333,735, previously incorporated by reference.

Although the catheter hub 300 of FIG. 16 is described resembling the catheter hub 300 of FIGS. 11-13, the catheter hub 300 of FIG. 16 can be any of the other catheter hubs described elsewhere herein. For example, the catheter hub 300 of FIG. 16 can be a standard hub without an internal change in profile, such as the catheter hub 102 of FIG. 2, can have a tilted hub body with an angular offset α, such as the catheter hub 102 of FIG. 3, or can have a two-part hub body, such as the two-part catheter hub 250 of FIG. 6. Upon placement of the catheter tube 104 into the vasculature of a patient and following removal of the needle 342 and needle guard 366, any of the various male Luer connectors 106 or male closing caps 180 described elsewhere herein can be used with the catheter hub 300 to either sample fluid or introduce fluid into the catheter hub.

Thus, an aspect of the present disclosure is understood to include a catheter hub having a body with two centerlines that are angled to one another. For example, the distal section of the catheter hub can have a centerline and the proximal section of the catheter hub can have another centerline and wherein the two centerlines can be angled relative to one another. In some examples, the distal and proximal hub sections with two different centerlines can be singularly formed. In other examples, the distal and proximal hub sections can be separately formed and subsequently attached or assembled together using conventional means.

The catheter assembly can further comprise a valve comprising at least one slit. In some examples, the valves can have three slits defining three flaps, which can be deflected by a valve opener. Thus, the catheter assembly can further comprise a valve opener for opening the at least one slit of the valve when advanced by a male Luer tip, such as by a male Luer connector of the present disclosure, which can have a single centerline or two centerlines that are angled relative to one another.

The catheter assembly can further comprise a needle guard located in the catheter hub, as previously described. The needle guard can have a proximal wall with an opening and the needle can have a change in profile for engaging the proximal wall at the opening. The needle guard can be located in the catheter hub with the valve and the valve opener. For example, the valve opener can have a holding space and at least part of the needle guard can be positioned in the holding space of the valve opener. In other examples, the needle guard can be located in a separate guard housing, such as a hub having a cavity for retaining the needle guard outside of the catheter hub. The guard housing can interact with the catheter hub, such as having a finger abutting or touching the catheter hub in a ready to use position.

A still further aspect of the present disclosure is a male Luer connector. Wherein the male Luer connector can include a male Luer tip, a tubing coupling extending in an opposite direction of the male Luer tip and connected to a tubing length, which can be part of an IV administrative set or an extension set. A collar having internal threads can surround at least part of the male Luer tip. The collar can be fixed and not rotatable or can be movable or rotatable relative to the male Luer tip. The male Luer connector can have a body having two centerlines that are angled to one another. The angle between the two centerlines can be about 150 degrees to about 175 degrees. If 180 degrees, the male Luer connector is understood to not have any angular offset or angle between any two centerlines.

The male Luer connector can include a collar and wherein the collar can be straight or can have a wedge shape, with or without a variable gap. The male Luer connector can include a male Luer tip having a centerline and a tubing coupling with a centerline and wherein the two centerlines can be angled to one another. The angle between the two centerlines can be about 155 degrees to about 179 degrees.

Additionally or alternatively, a separately formed support feature, similar to the support feature discussed with reference to FIG. 1B, can be attached to the tubing coupling of the male Luer connector instead of or in addition to utilizing an angular offset of a catheter hub and/or an angular offset of a male Luer connector. Further, the separately formed support feature can fit around the tubing coupling of the male Luer connector, which can connect to a tubing of IV administrative set or extension set, to support the tubing coupling and possibly also support part of the collar, which can be a straight collar without a variable wall thickness or a collar with a variable gap or thickness. The separately formed support feature can comprise a structure having a bore and a wedge shape body section for supporting the tubing coupling and can be used with various male Luer connectors discussed elsewhere herein.

The male Luer connector can include a tubing coupling opposite an end with a male tip that can embody a female receptacle for receiving an IV tubing or can embody a male nipple for projecting into an IV tubing. The tubing length can be part of an extension set or an IV administrative set.

Aspects of the present disclosure are further understood to include a conically shaped collar, for use with a male Luer connector or a male closing cap, to increase surface contacts with a patient's skin and provide support for an infusion system. The conically shaped collar can be fixed relative to a male Luer tip or be rotatable relative to the male Luer tip. Internal threads can be provided with the conically shaped collar.

The catheter hubs described herein can have a single centerline or two centerlines or can be formed from at least two hub sections with two centerlines that are angled to one another for use with a male Luer connector with a single centerline or with two centerlines that are angled to one another.

Figure 17:
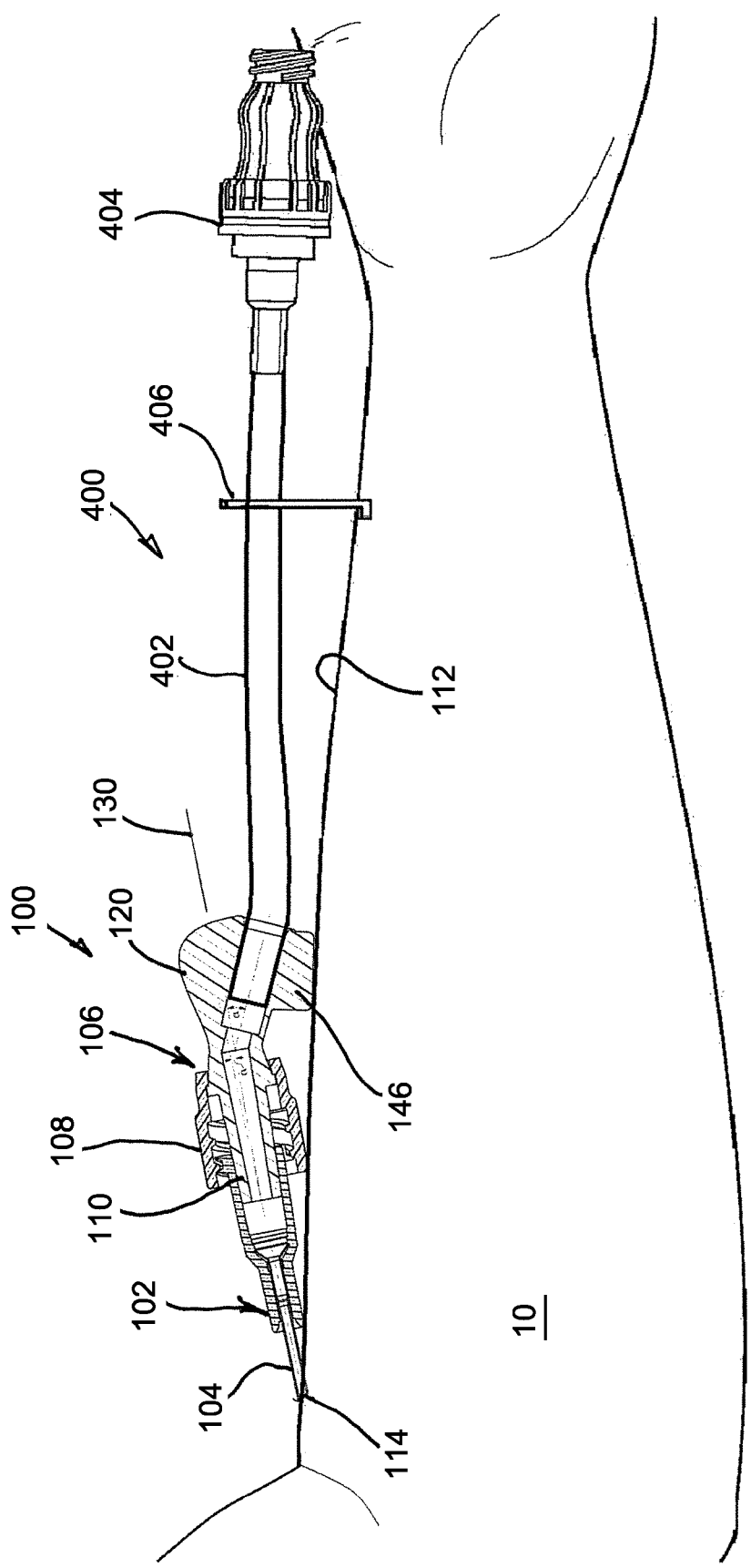
FIG. 17 is partial cross-sectional and elevation view of an infusion system of the present disclosure comprising a catheter hub and an extension set.

With reference now to FIG. 17, the infusion system 100 of FIG. 1B is shown with an extension set 400 and with the catheter tube 104 accessing the vasculature of a patient 10 at a puncture site 114. The catheter hub 102 and the male Luer connector 106 are shown resting against a surface, such as the patient's skin 112. Although the infusion system 100 of FIG. 1B is shown with the extension set 400, it is understood that any of the various catheter hubs and male Luer connectors described in FIGS. 1-15 can be used.

As shown, the tubing coupling 120 of the male Luer connector 106 can connect to a first end of a tubing length 402 and a fitting 404, such as a needleless valve, can connect to a second end of the tubing length 402. A slide clamp 406 can be provided between the two ends of the tubing 402 to clamp the tubing. A roller clamp (not shown) may also be included and mounted over the tubing 402 in addition to the slide clamp 406. If the extension set 400 shown in FIG. 17 was instead an IV administration set, the length of tubing 402 would be longer and the fitting 404 would be a universal spike having a drip chamber instead of the needleless valve shown. In other embodiments, a Y-site with a needleless valve or other fittings can be included with the IV administration set or the extension set. The extension set 400 and the IV administration set can still include other components and can be customizable as needed to include multiple needleless valves, multiple Y-connectors, or to include other fittings. Thus, the exemplary components described herein for the extension set 400 and the IV administration set are not limited.

As shown, the male Luer tip 110 connects the extension set 400 to the catheter hub 102 and allows fluid to be administered through the catheter hub 102 and out the catheter tube 104, such as by injecting fluid with a syringe at the needleless valve 404 into the patient 10 via the catheter hub and catheter tube. The spin lock collar 108 is threaded over the external threads of the catheter hub 102 to more securely hold the male Luer connector 106 to the catheter hub. Optionally, the collar can be omitted and the male Luer tip 110 is used as a Luer slip.

As previously alluded, the angle between the assembly centerline 130 of a catheter hub and male Luer connector and the surface of the skin 112 is about 5 degrees to about 15 degrees. If a standard non-angular offset male Luer connector and/or a standard non-angular offset catheter hub are used, the proximal edge 140 (FIG. 1) of the tubing coupling 120 to the surface of the skin 112, previously described herein as the set gap 144, is about 22 mm to about 26 mm. These ranges can of course vary depending on the length and geometries of the various components. Notwithstanding the range variations, an unsupported set gap 144 can allow the entire infusion system 100, such as the tubing coupling 120, to move up and down relative to a surface, unintentionally or otherwise, so that the set gap 144 can vary from zero to some large gap value relative to the skin 112. When the tubing coupling is so moved, the catheter tube 104 at the puncture site 114 can bend, displace proximally, and/or kink and obstructs fluid flow through the infusion system, among other problems.

As shown in FIG. 17 and previously described, the male Luer connector 106 can be supported at the tubing coupling 120 so that a physical barrier is interposed between the skin 112 and the tubing coupling 120 to take up any gap therebetween. Said differently, the infusion system 100 of the present disclosure includes means for supporting the male Luer connector 106 at the tubing coupling 120 against the skin 112.

In an example, the catheter hub 300 is provided with an angular offset α, the male Luer connector 106 is provided with an angular offset α1, or both the catheter hub and the male Luer connector are provided with angular offsets α, α1 to relocate the proximal edge of the tubing coupling 120 closer to the skin or touch the skin compared to a prior art infusion system without any angular offsets. As described above, an angular offset α can be incorporated in a catheter hub and/or in a male Luer connector by forming a structure with at least two sections each having a centerline that are angled relative to one another.

Although the tubing 402 is shown bent back to a position parallel to the skin in FIG. 17, as described above, the relatively soft tubing can bend at the exit angle under its own weight and touch the skin to form part of the stabilizing platform of the IV infusion system. Also a skilled artisan will appreciate that the tubing 402 can normally be looped to extend the needleless valve in the same direction as the catheter tubing. Thus FIGS. 17 and 22 can be viewed as intermediate positions and not as final positions, respectively. The skilled artisan will also note that the puncture site pictured in FIGS. 17 and 22 would not be at the inside of the elbow. These figures are simplified to show the relevant features of the invention.

As discussed above with reference to the embodiment of FIG. 1B, a support feature 146 in the form of a separately formed adaptor may be placed around the tubing coupling 120 to provide support. For example, following placement of the catheter tube 104 into the vasculature of the patient 10 at the puncture site 114, the adaptor 146 can slide under the tubing coupling 120 to take up any gap that may be present between the skin and the proximal edge of the tubing coupling to physically support the male Luer connector from possible rocking up and down relative to the skin at the proximal end of the tubing coupling.

The support feature 146 can be used with the tubing coupling of a male Luer connector 106 with or without an angular offset. For example, if the male Luer connector 106 is a standard connector without any angular offset α, then the adaptor 146 can be configured to take up a typical set gap of about 22 mm to about 26 mm to physically support the tubing coupling 120 against the skin 112. If the male Luer connector 106 incorporates an angular offset α1 so that the proximal edge of the tubing coupling 112 is repositioned closer to the skin, then the support adaptor 146 only has to take up a relatively smaller set gap 144, typically less than the range of 22 mm to 26 mm, to physically support the tubing coupling against the skin. In an example, the support adaptor 146 can be sized and shaped to take up a range of set gaps by incorporating a ramped surface, similar to a wedge or a tapered shim, to take up any slack of a certain range, such as between 2 mm and 30 mm. The ramped or wedge shaped structure allows the gap between the tubing coupling and a surface, such as the skin, to be taken up in increments of the slope of the ramped structure. Optionally, the internal wall of the support feature 146 defines a support surface that is not sloped or wedge shaped. For example, the support surface can comprise a plurality of spaced apart bumps or projections or be flat.

Figure 18:
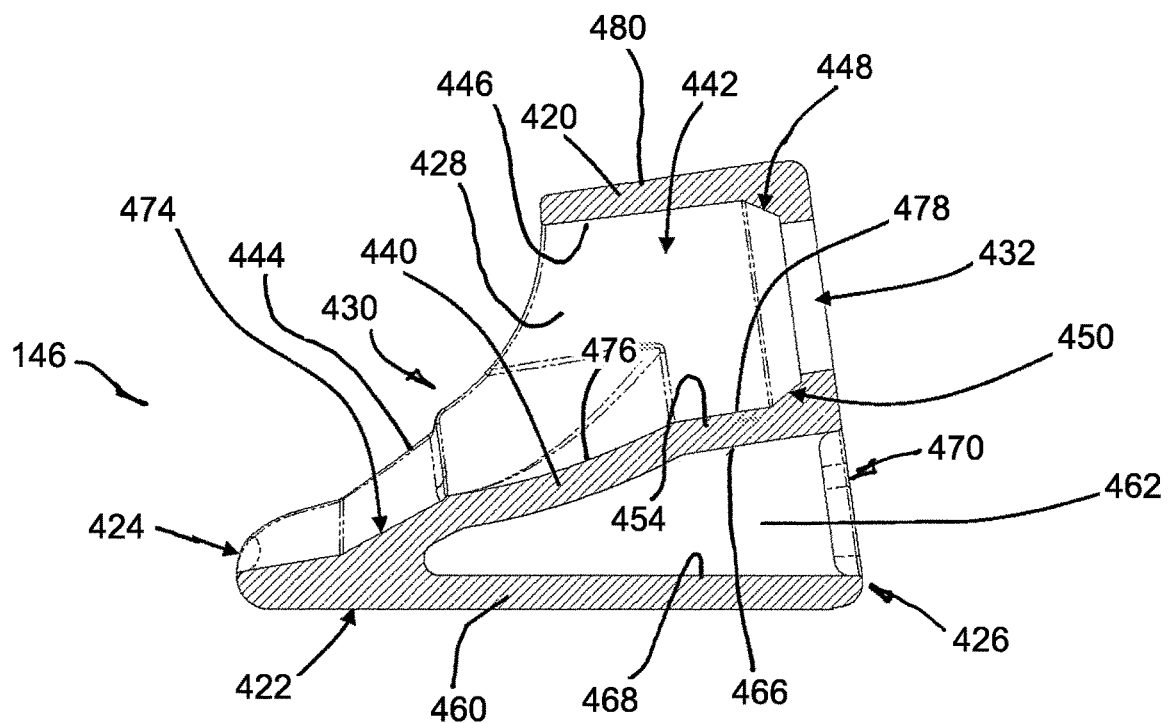
FIGS. 18-21 are different views of a support feature or support adaptor usable with an infusion system, such as with an extension set or IV administration set.
Figure 19:
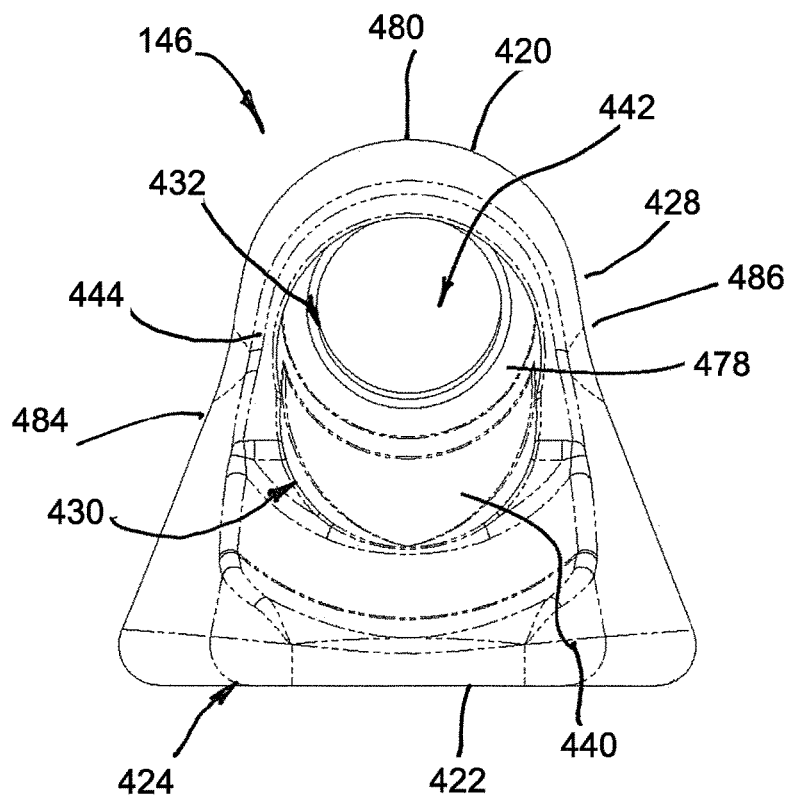

With reference now to FIG. 18, a cross-sectional side view of a support feature 146 in the form of an adaptor described with reference to FIG. 1B is shown. The support, support feature, or adaptor 146, used interchangeably, can be a molded plastic piece having a body 420 with a generally boot-shaped side elevation. The body can instead be molded or formed from an elastomer, for example from rubber or silicone. The body 420 has a base or base wall 422, a first end 424, second end 426 and a body wall 428 with a curved upper dome wall surface 480 (FIG. 19). The body 420 comprises a support opening 430 accessible from the first end 424 and a through opening 432 accessible from the second end 426. The body wall 428 can be continuous, such as being a continuous wall. By continuous, the body wall, including the curved upper dome wall surface 480, can be without a gap, a slit or a slot extending through the wall to permit a tubing length to engage the support feature through the gap, slit, or slot. The body wall 428 therefore has a continuous wall surface in a radial direction relative to a length between the first end 424 and the second end 426 of the body 420. The body wall 428 defines an exterior of the body 420. The wall surface having the through opening 432 can be vertical compared to a surface, such as the skin, or can slant or angled relative to the surface.

A through bore 442 is defined by the body wall 428 and an internal wall 440 between the support opening 430 and the through opening 432, which can also be referred to as a first opening and a second opening, respectively. Further, because the adaptor 146 is to be oriented so that the first opening 430 is closer to a male Luer connector and the second opening 432 further away when located on a tubing of an IV administration set or extension set, the first opening may also be referred to as the distal opening the second opening as the proximal opening. As disclosed, a tubing length can only connect to the support feature or adaptor 146 by passing an end of the tubing length through both the first and second openings 430, 432 since there is no gap, slit or slot in the continuous body wall. Once the tubing length is located within the bore 442, the support feature 146 is rotatable about the tubing length and the tubing length is located in the bore 442 that is bounded by a continuous wall around the entire circumference of the bore.

Alternatively, support feature 146 can be longer than shown and have a bore that extends the length of the longer body and wherein the bore of the extended body can have an angular offset α2, similar in concept as previously described embodiments. In this way, the tubing 402 extending out the tubing coupling can be angled towards the patients skin by the angular offset of the longer support feature and close the gap between tubing 402 and the patient, such as to a smaller gap or to zero. This can eliminate the risk of kinking off the flow through the tubing 402 and allow full coverage by a sterile adhesive dressing. A support feature with an extended length with an angular offset is further discussed below with reference to FIG. 23A.

The through opening or proximal opening 432 of the support 146 can have an opening diameter of about 4 mm to about 5.5 mm, or as necessary to accommodate a typical tubing diameter of an IV admin set or an extension set. The support opening or distal opening 430 can be sized to be larger than a diameter of the largest cross-section of a tubing coupling, in the order of about 15% or larger, such as 50% larger or 75% larger than the tubing coupling. As further discussed below, a tubing line of an IV admin set or extension set can pass through the bore 442 of the support 146 and the support is configured to slide under the tubing coupling of a male Luer connector (FIGS. 1 and 17) to support the tubing coupling against a patient's skin. Optionally, part of a collar of the male Luer connector can also be supported by the support feature or support adaptor.

The support opening 430 is defined by an inclined perimeter 444, which resembles an exponential slope along a side view so as to define a wide support opening 430 that is angled. The wide support opening 430 is sized and shaped to readily receive a proximal end of a tubing coupling when the support adaptor or feature 146 slides under the male Luer connector 146 to support the tubing coupling. The wide support opening 430 is sized and shaped to accommodate some mis-alignment between the opening 430 and the proximal end of the tubing coupling while still allow the two to mate, as further discussed below. The first opening or support opening 430 of the support feature 146 defines a plane and wherein the plane is angled relative to the base 422 by an angle of about 20 degrees to about 80 degrees. In a particular example, the angle between the plane defined by the first opening 430 and the base 422 is from about 35 degrees to about 75 degrees, such as 45 degrees to 65 degrees.

Figure 23:
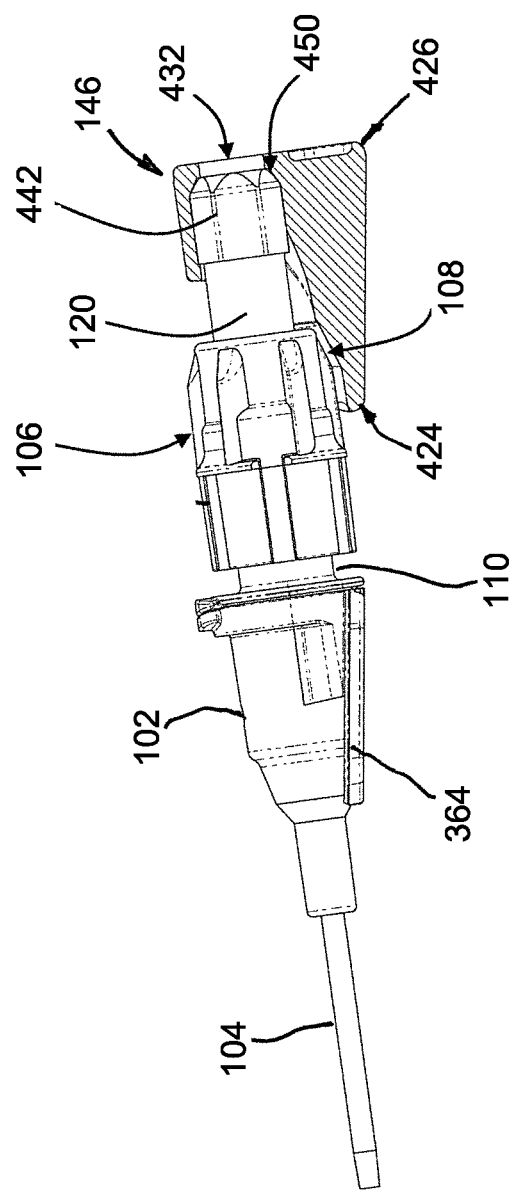
FIG. 23 is a partial cross-sectional and elevation view of a support feature or support adaptor located below a male Luer connector without the tubing of the extension set or IV administration set.

In an example, the internal wall 440 can extend from the first end 424 to the second end 426 of the body 420 and slopes upwardly, elevation-wise, as it extends to the second end 426. A radius or bevel 448 can be provided at the end of the bore 442 next to the through opening 432 so as to define a reduced opening at the through opening 432 compared to the bore diameter adjacent the through opening. The bore is bounded by a retaining lip or shoulder 450. In an example, the retaining lip or shoulder 450 is configured to stop the tubing coupling of a male Luer connector from moving further proximally beyond the lip 450 but the tubing is allowed to pass through the second or proximal opening 432. The radius or bevel 448 may be configured to compliment the bevel on the proximal end of the tubing coupling, as shown in FIG. 23.

In an example, the internal wall 440 of the support feature 146 is undulating as it inclines from the first end 424 towards the second end 426. In other examples, the internal wall can be generally flat as it inclines. In still other examples, knurls or ridges may be provided on the upper surface 454 of the internal wall 440 to provide latching points or resting points for the tubing coupling as the tubing coupling is received inside the bore 442, as further discussed below. Optionally, the inside surface 446 of the curved upper dome 480 or the inside surface of the two sides 484, 486 (FIG. 19) or both can incorporate undulating surfaces, knurls or ridges to provide latching points or resting points for the tubing coupling.

In an example, the bore 442 and the surface contour of the internal wall 440 can be sized and shaped to snuggly receive a proximal end of a male Luer connector, such as to snuggly receive a tubing coupling. For example, the bore 442 and the surface contour of the internal wall 440 can be sized and shaped to snuggly receive Model No. 1234 male Luer connector from Company XYZ, wherein the model number and the company can represent any of the various manufacturers of commercially available male Luer connectors.

In an example, the bore 442 tapers or is approximately frustoconical as it extends from the first end 424 to the second end 426. Further, the inclined surface of the internal wall 440 and the base 422 defines a ramp or wedge shaped structure 460. The wedge shaped support 460 is located elevation-wise below the bore 442. The upper surface for the wedge shape support can define part of the bore. The ramp or wedge shaped structure 460 is configured to function as a shim to fill up or take up space between the tubing coupling of a male Luer connector and a surface, such as a patient's skin, to physically support the tubing coupling against the surface.

Optionally, the internal wall 440 of the support feature 146 defines a support surface 460 that is not sloped or wedge shaped. For example, the support surface can comprise one or more bumps, can comprise sections extending from an enlarged interior of the body wall, or be flat as it extends from the first end to the second end.

The support surface 460 of the support adaptor 146 can act as a shim with a variable thickness to take up different set gaps between the proximal edge of a tubing coupling and the skin, from about a 2 mm set gap up to about a 24 mm set gap to about a 30 mm set gap. However, the set gap range that the support adaptor 146 can support is not limited as the structure of the support adaptor or feature 146 can be modified to support a larger range. When in use and as the support surface 460 supports the tubing coupling of a male Luer connector, the internal wall 440 and the body wall 428 defining the bore of the adapter 146 can secure the tubing coupling from lateral movement, upward movement, or both.

As shown, the upper surface 454 of the internal wall 440 defines a plane and wherein the plane of the upper surface 454 can be angled relative to the base 422. The angle between the plane of the upper surface 454 and the base 422 can be about 5 degrees to about 45 degrees with all values in between being contemplated. To provide a more inclined support surface, the angle between the plane of the upper surface 454 and the base 422 can be about 15 degrees to about 35 degrees.

A void space 462 may be formed in the support 146 to reduce materials to mold the support and therefore reduce costs. The void space 462 can also introduce additional resiliency to the body of the support. The resiliency of the support may otherwise be controlled through material selection and durometer. The void space can optionally be omitted, such as by molding a solid body. The void space 462, when incorporated, can be defined by the interior surface 468 of the base 422 and the lower surface 454 of the internal wall 440, which also divides the void space 462 and the bore 442. In an example, the void space 462 extends from a void space opening 470 towards the first end 424, which can be a closed end. Because the void space 462 is bounded by the sloped internal wall 440 and the base 422, the void space has a wedge shape similar to the wedge shaped support structure 460. However, the void space 462 can have a different shape than the shape of the support structure 460. The support structure or surface 460 can also have a shape other than a slope or a wedge. Optionally, the void space can be provided with ribs to reinforce the internal wall 440.

The undulating surface of the internal wall 440 may comprise different angles of inclination from the first end 424 towards the second end 426. In the embodiment shown in FIG. 18, the wall may have an initial steep inclined upper surface illustrated at 474, called the entry region. The entry region 474 may serve to facilitate capture of the tubing coupling of a male Luer connector and assist in guiding it deeper into the bore 442. Further in the bore 442, the internal wall 440 has a central or middle region 476 and an end region 478. In use and depending on how far the support adaptor 146 is pushed over a male Luer connector to receive the tubing coupling, the tubing coupling of the male Luer connector can rest against the entry region 474, the middle region 476, the end region 478, or between two or more of the regions. In an example, the middle region can take up a greater set gap than the entry region because it is located further up the sloped internal wall than the entry region. In an example, the end region can take up a greater set gap than the middle region because it is located further up the sloped internal wall than the middle region. As the bore 442 can have undulating surfaces, the bore can be considered to have a bore path that extends in the same general direction. The bore 442 can also have a centerline through the bore path. As shown, the bore 442 has a single bore path extending in the same general direction.

FIG. 19 is a front view of the support 146 of FIG. 18, looking at the support opening 430 at the first end 424 towards the through opening 432 at the second end 426 (FIG. 18). Note that the internal wall 440 has a generally concave top surface 454 and slopes upward from the first end 424 to receive the proximal end of a male Luer connector and guide it into the bore 442. Also clearly shown is the relative widths of the base 422 and of the curved upper dome wall surface 480 of the body wall 428. The width of the base 422 can be about 30% to about 100% wider than the width of the curved upper dome wall surface 480. In other examples, the width of the base can be greater than 100% of the width of the upper dome wall surface, for example by extending wings from the base 422. The wider dimension at the base 422 can indicate which end of the support feature 146 is to be positioned against the skin. As dimensioned, the relatively wider base 422 provides a stable surface area against tilting and for providing a greater contact area with a patient for patient comfort. For example, when applying pressure sensitive adhesive to secure the support feature, the wider base 422 resists tilting or tipping.

In an example, the curved upper dome wall surface 480 of the body 420 of the adaptor 146 is continuous along a radial direction relative to the lengthwise axis or length of the support adaptor 146. The base 422 as well as the sides 484, 486 of the body 420 can also be continuous without any slit or slot. Because of the continuous body wall 428, including a continuous upper dome wall surface 480 and continuous base 422, the adaptor must be mounted onto a tubing length of an extension set or an IV administration set by passing an end of the tubing length through both the distal opening 430 and the proximal opening 432. There is no side slot or channel in the support 146 to otherwise mount the support 146 to the tubing, or vice versa, via from a side of a tubing length. Said differently, at least one end of a tubing length must be routed through the bore 442 and the two openings 430, 432 of the support 146 to mount or assemble the support 146 to an IV admin set or extension set. Thus, because of the continuous nature of the upper dome surface 480 and the body wall 428, the support adaptor 146 must be assembled and provided as part of an extension set or IV administration set in a packaged or manufactured state. Less preferably, the tubing length can be detachable from a fitting or from a male Luer connector of an extension set or IV administration set to route through the bore 442 and two openings 430, 432 of the support feature 146 and then re-connected.

Thus, an aspect of the present disclosure is understood to include an extension set or an IV administration set comprising a male Luer connector at a first end of a tubing length and a fitting at a second end of the tubing length, and wherein the male Luer connector has a tubing coupling having a support structure for supporting the tubing coupling against a patient's skin, when the extension set or the IV administration set is used with a catheter hub having a catheter tube. In an example, the support structure can be unitarily formed with the tubing coupling. In another example, the support structure can be separately formed and movable into contact with the tubing coupling to support the tubing coupling against the patient's skin. The support structure can optionally include a pair of wings.

The support structure can comprise an angular offset within the catheter hub so that an end of a tubing coupling of a male Luer connector connected to the catheter hub is moved closer to the skin due to the angular offset.

In another example, the support structure can comprise an angular offset within a male Luer connector so that an end of a tubing coupling of the male Luer connector is moved closer to the skin due to the angular offset.

In yet another example, the support structure can comprise a support feature sized and shape to function as a shim to take up any space or gap between a proximal end of a tubing coupling of a male Luer connector and a surface, such as the skin. The support feature can be unitarily formed with the tubing coupling or be separately formed and movable into contact with the tubing coupling. The separately formed support feature can be similar to the support feature disclosed in FIGS. 18 and 19, which can comprise a body comprising a bore bounded by a continuous wall and having a first opening and a second opening at the ends of the bore. The first opening can be larger than the second opening and can be an angled opening. In yet other examples, the support structure can comprise a combination of structures described herein.

Figure 20:
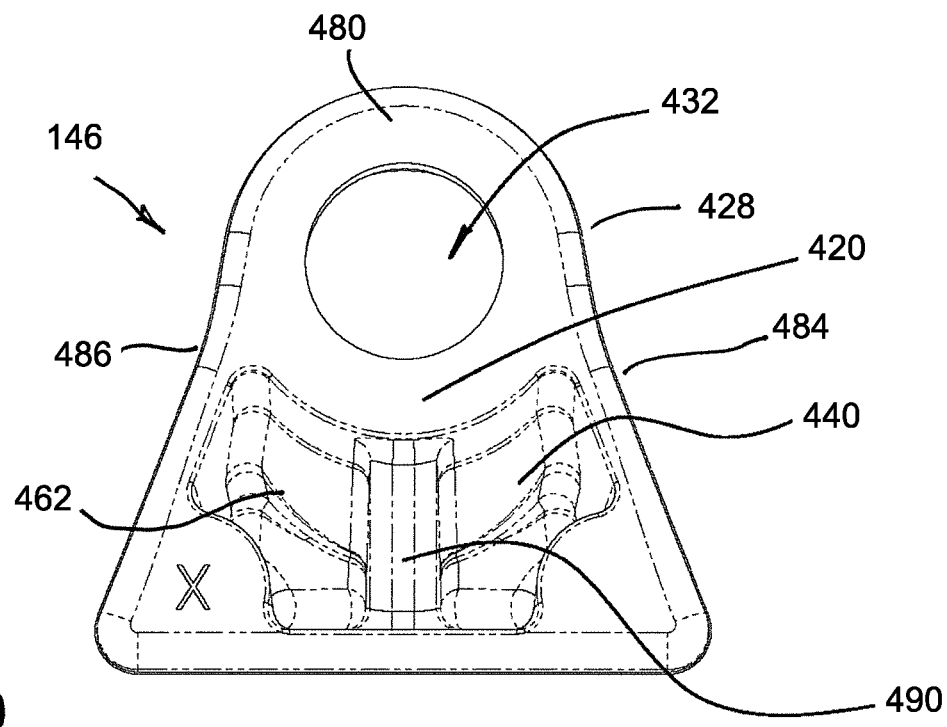

FIG. 20 illustrates a rear view of the support adaptor 146 of FIG. 18, looking from the second end 426 toward the first end 424 with the various shaped features shown in dashed lines representing hidden lines. As illustrated, the second or proximal opening 432 is generally centrally positioned relative to the curved upper dome wall surface 480 of the body wall 428 and relative to the two sides 484, 486. Also shown is the void space opening 470 and the void space 462 inside the opening. The void space opening 470 has an irregular shaped opening having many sides and angles. In other examples, the void space opening 470 can be round, square, or polygonal. The dashed-lines shown in FIG. 20 include many line extensions and curves, including an elongated bar 490 representing the contour of the upper 454 and lower 466 surfaces of the internal wall 440.

Figure 21:
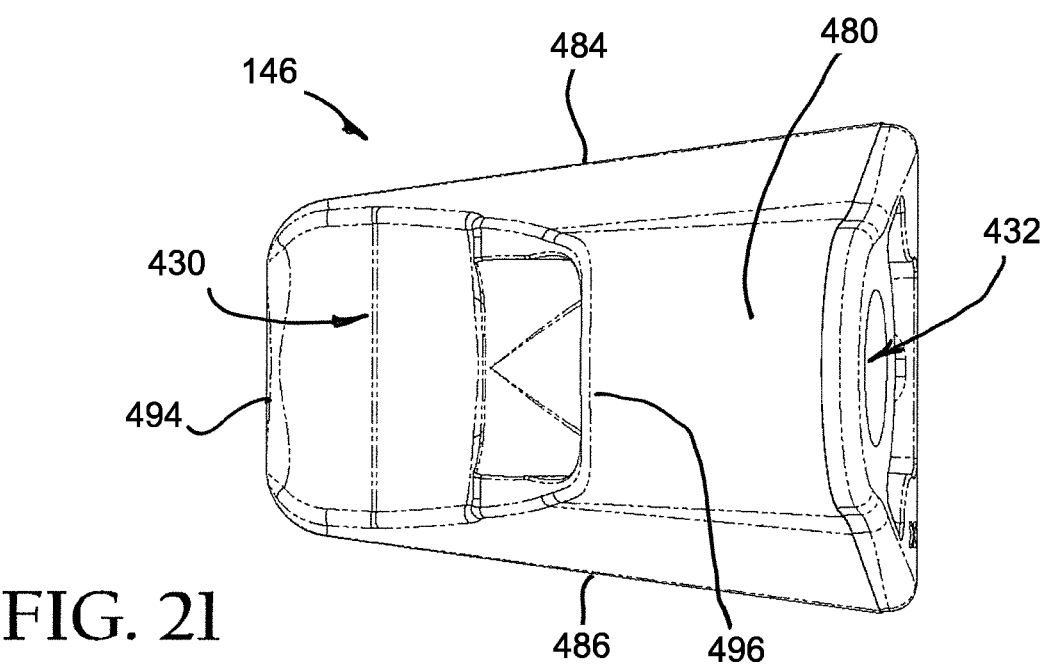

FIG. 21 is a top view of the support adaptor 146 of FIG. 18, looking down at the upper dome surface 480 and at the first or distal opening 430. From the perspective shown, the first or distal opening 430 can resemble a trapezoid with the lower perimeter section 494 closer to the base 422 being wider than the upper perimeter section 496 closer to the upper dome surface 480. Thus, the first or distal opening 430 is not only inclined (FIG. 18), the perimeter 444 of the first opening can also taper inwardly at it inclines.

Figure 22:
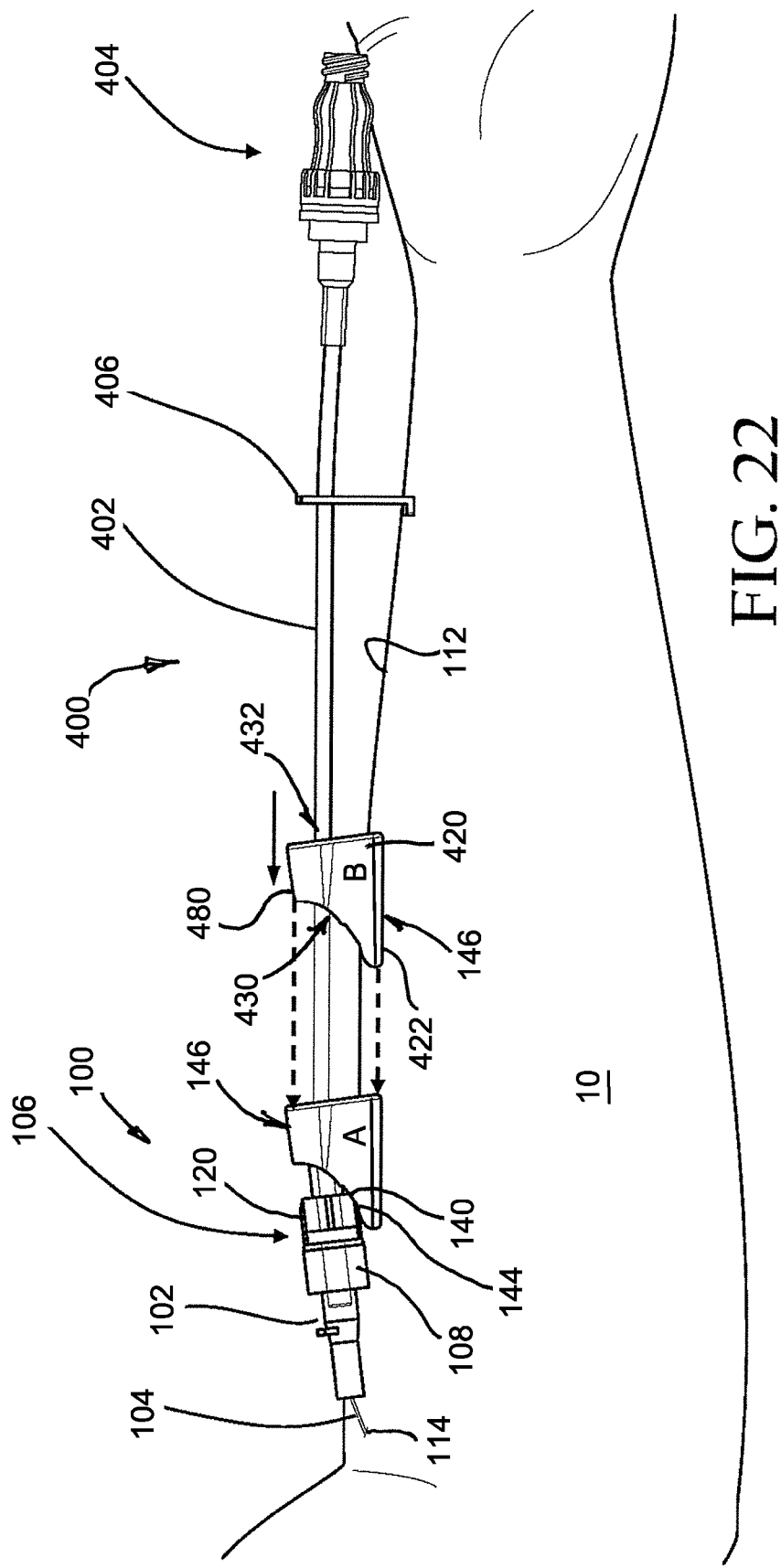
FIG. 22 is a side elevation view of an infusion system of the present disclosure comprising a catheter hub and an extension set with a support feature supporting a male Luer connector.

With reference now to FIG. 22, an infusion system 100 is shown with the catheter tube 104 accessing the vasculature of a patient 10 at a puncture site 114 and the catheter hub 102 and male Luer connector 106 resting against the patient's skin 112, similar to that of FIG. 17. The infusion system 100 is shown with an extension set 400. The catheter hub and the male Luer connector of the infusion system 100 can represent any of the various catheter hubs and male Luer connectors described elsewhere herein, including in the embodiments with one or more offset angles. In other examples, the extension set 400 can instead be an IV administration set, which can have a universal spike with a drip chamber.

Also shown with the extension set 400 of FIG. 22 is a support adaptor 146 having a tubing length 402 passing through the bore and the two openings 430, 432 of the body 420. The support adaptor 146 can be the similar to the adaptor of FIGS. 18-21. The support adaptor 146 can be located along the tubing length 402 at a before "B" position away from the tubing coupling 120 of the male Luer adaptor 106 and movable to an after "A" position, or engaged position, in contact with and supporting the male Luer adaptor, as further discussed below. In the before "B" position, the support adaptor 146 is rotatable relative to the tubing length and the tubing length is located within the bore bounded by a continuous wall.

In the present example, the catheter hub 102 is a standard hub with a single system centerline and the male Luer connector 106 is a standard connector with a single connector centerline. In other words, neither component incorporates an angular offset. Thus, in the infusion position of FIG. 22, the proximal edge 140 of the tubing coupling 120 of the male Luer connector 106 is spaced from the skin 112 by a set gap 144 while maintaining the catheter tube 104 along a relatively straight axis so as not to restrict flow through the catheter tube. To take up the set gap and support the tubing coupling 120 against the skin 112, the support adaptor 146 can slide distally relative to the catheter hub 102 from position B to position A to take up the set gap. During this movement, the length of tubing 402 is allowed to pass through the bore between the support opening 430 and the through opening 432. As previously described, the support adaptor has an upper dome wall surface 480, which has a continuous wall surface without any slit or slot. In the engaged position, at position A of the support feature 146, the tubing coupling 120 is physically supported against the skin 112.

Alternatively as described above, the support feature 146 can be longer so that the bore 442 extends the length of the longer body and has a similar angular offset α as previously described catheter hubs and male Luer connectors, which can be used for the same advantages as described for the previous embodiments. In this way, the tubing 402 can be angled towards the patient's skin and closing the gap between tubing 402 and the patient to zero or close to zero. This extended body with an angular offset α can eliminate the risk of kinking off the flow through the tubing 402 and allow full coverage by a sterile adhesive dressing. Aspects of an extended support feature 146 are further described below with reference to FIG. 23A.

If the catheter hub has an angular offset, the male Luer connector has an angular offset, or both the catheter hub and the male Luer connector have angular offsets, then the support adaptor 146 can comprise or can incorporate a slit or slot in order to mount the support adaptor onto the tubing length of the extension set or IV admin set by passing the tubing length through the slit or slot on the support adaptor. In other words, where an angular offset is incorporated, a tubing length can slide through a gap, slit, or slot and not have to pass through the two openings 430, 432 of the support feature to mount the support feature to the tubing. Thus, where a slit or a slot is provided with a support adaptor or feature 146, such as the support adaptor of FIGS. 18-21, the support adaptor 146 can be added to the tubing length of an extension set or an IV administration set after the tubing length has been connected at the tubing's two ends.

The support adaptor or feature 146 is slidable along the tubing 402 into an engaged position or after position A in contact with the tubing coupling 120 of the male Luer connector 106, at the proximal end of the tubing coupling. With continued reference to FIG. 22 and further reference to FIGS. 18-21, in the engaged position, the tubing coupling 120 enters the support opening 430 at the first end 424 of the body 420. The support adaptor 146 can move over the tubing coupling 120 to support the tubing coupling and take up the set gap 144 between the proximal edge of the tubing coupling and the skin. Depending on the dimension of the set gap 144, the support adaptor 146 can move over the tubing coupling 120 so that the tubing coupling rests against the entry region 474, the middle region 476, or the end region 478 of the internal wall 440 of the support adaptor 146.

The support adaptor or feature 146 can also move a maximum amount over the tubing coupling 120 until the proximal end of the tubing coupling contacts the lip or shoulder 450 inside the bore 442 near the second end 426. The amount of engagement between the support adaptor or feature and the tubing coupling can be selected by the practitioner to provide the most optimum alignment for the catheter tube 104 at the puncture site 114. Once engaged at a desired position, securement tape or adhesive may be applied over the catheter hub, the male Luer connector, the tubing adaptor, or combinations thereof to maintain the catheter tube at the desired alignment or angle with the tubing coupling supported by the support feature.

FIG. 23 is a side elevation view of an infusion system 100 comprising a catheter hub 102, a catheter tube 104, and a male Luer connector 106 comprising a male Luer tip 110, a spin lock collar 108 that is rotatable relative to the male Luer tip 110, and a tubing coupling 120. A support adaptor 146 is shown pushed against the tubing coupling 120 so that the tubing coupling projects into the bore 442 of the support adaptor and rests against the lip or shoulder 450 at the second end 426 of the body 420, similar to that shown in FIG. 22. In other examples, the proximal end of the tubing coupling 120 can be spaced from the lip or shoulder 450. As shown and with further reference to FIG. 18, the proximal end of the tubing coupling 120 rests against the end region 48 of the internal wall while the collar 108 rests against the entry region 474 of the internal wall. The present support adaptor 146 is also shown without a void space with such space contemplated. A tubing line has been omitted from FIG. 23 but is understood to be part of the extension set extending out the proximal end of the tubing coupling 420 and out the through opening 432 of the support adaptor. The proximal end of the tubing coupling 120 can fit snuggly within the bore 442 or the inside diameter of the bore 442 can be larger than the tubing coupling and not grip the exterior of the tubing coupling.

The support adaptor 146 may be composed of any material compatible with human contact, but will typically be composed of a plastic, typically a thermoplastic material suitable for injection molding. The plastic may be comprised of one or more different polymers, such as polyolefins. In one embodiment, the body of the stabilizer is composed of polyethylene, and in particular LDPE. The support adaptor 146 may alternatively be made form a rubber or silicone material.

Figure 23A:
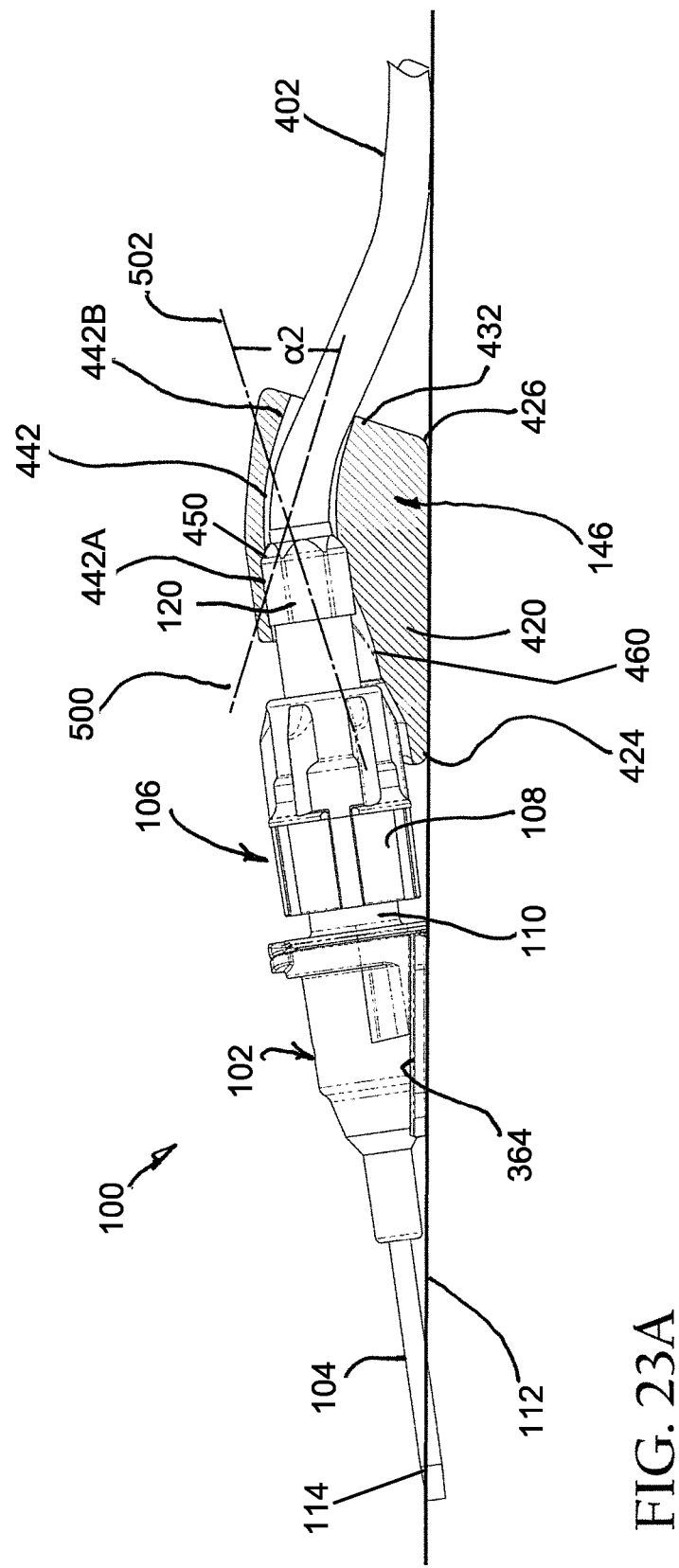
FIG. 23A is a partial cross-sectional and elevation view of an alternative support feature or support adaptor located below a male Luer connector with a tubing length of an extension set or IV administration set partially shown.

FIG. 23A is a side elevation view of an infusion system 100 comprising a catheter hub 102, a catheter tube 104, and a male Luer connector 106 comprising a male Luer tip 110, a spin lock collar 108 that is rotatable relative to the male Luer tip 110, and a tubing coupling 120 and be similar to the infusion system of FIG. 23. The infusion system 100 is shown positioned against a surface 112, which can be the skin of a patient. The catheter tube 104 has been artificially shortened to simplify the Figure. The skilled artisan will appreciate that the distal most portion of the catheter tube 104 will be located in a vein under surface 112 when in use for IV access.

A support adaptor 146 is shown pushed against the tubing coupling 120 so that the tubing coupling projects into the bore 442 of the support adaptor and rests against the lip or shoulder 450 of the body 420. The support adaptor 146 shares many similarities with the support adaptor of FIGS. 18-21 with some differences discussed herein.

Although shown in contact, the proximal end of the tubing coupling 120 can be spaced from the lip or shoulder 450 of the support adaptor 146. The lip or shoulder 450 prevents the tubing coupling 120 from moving further proximally of the lip or shoulder within the bore 442. A tubing length 402 is shown connected to the tubing coupling 120, which length can be part of an extension set or an IV administration set.

In the present embodiment, the support adaptor 146 is elongated and the bore 442 incorporates an angular offset α2. As shown, the bore 442 in the present embodiment is provided with a first bore section 442A having a first bore centerline 502 and a second bore section 442B having a second bore centerline 500, which is angled relative to the first bore centerline 502 by an angle of from about 140 degrees to about 179 degrees. The first bore centerline 502 can be collinear with the common centerline of the catheter hub, the male Luer connector, or be angled to the common centerline. In some examples, the angle between the first and second bore centerlines can be from about 150 degrees to about 170 degrees.

As the first bore section 442A and the second bore section 442B can have undulating surfaces or curves but still extend along a general direction, the first bore section 442A and the second bore section 442B can be described as having a first bore path and a second bore path, respectively, which can be understood to include some bending, non-linear sections, or linear sections. As shown, the bore 442 has a first bore section 442A having a first bore path 502 and a second bore section 442B having a second bore path 500 and wherein the two bore paths are angled relative to one another. The two bore paths 500, 502 being at an angle to one another can be employed to change the direction of a tubing length extending out a tubing coupling 120 to generally conform to the two bore paths, as further discussed below. In other examples, there can be more than two bore sections within the bore 442 with more than two bore paths to angle or bend the tubing along more discrete paths within the bore.

The proximal end of the tubing coupling 120 can fit snuggly within the bore 442 or the inside diameter of the bore 442 can be larger than the tubing coupling 120 and not grip the exterior of the tubing coupling. As shown, the tubing length 402 extends through the second bore section 442B having the second bore centerline or second bore path 500 and out the through opening 432 at the second end 426 of the support adaptor 146. The diameter of the second bore section 442B can be larger than the outside diameter of the tubing length 402 so that the exterior of the tubing length is not gripped by the interior surface of the second bore section, as shown. Alternatively, only part of the second bore section 442B is sized to snugly grip the exterior of the tubing length or the entire second bore section 442 snugly grips the exterior of the tubing length.

In some examples, the second bore section 442B can have a second bore path 500 that is parallel to the bottom surface of the body 420 and wherein the second bore path 500 is angled relative to the first bore path 502 of the first bore section 442A. When so configured, the through opening 432 at the second end can be made or sized to be wider or larger than the rest of second bore section 442B, at least wider or larger in the lower direction elevation-wise to allow the tubing 402 to bend towards the patient's skin as an adhesive dressing is applied. This acts as a stress relief to avoid kinking off flow through tubing 402 extending out the enlarged through opening 432. In an example, the through opening 432 can enlarge from the inside diameter of the second bore section 442, similar to an expander or enlarger. In another example, a proximal end of the second bore section 442B can have a frustoconical shape.

As configured, the tubing length 402 can be deflected towards the surface 112, such as the skin of a patient when in use for IV access, by the extended bore 442, and specifically by the second bore section 442B of the bore. The tubing length 402 can contact an upper interior surface of the bore 442 to be deflected towards the skin by the upper interior surface. However, the tubing length can contact other interior surface areas of the second bore section 442B to deflect towards the skin. The angle of the second bore centerline or second bore path 502 can be selected to deflect the tubing length 402 towards the surface 112 a gradual amount from its normal bend or a steeper amount from its normal bend to close the gap between the tubing and the skin. By incorporating a support adaptor 146 with a bore with an angular offset to direct the bend of the tubing length, this feature can eliminate the risk of kinking off the flow through the tubing 402 and allows full coverage by a sterile adhesive dressing.

Methods of making and of using the infusions systems and their components, such as catheter hubs, support adaptors, and connectors, described elsewhere herein are within the scope of the present disclosure.

Although limited embodiments of infusion systems and their components have been specifically described and illustrated herein, many modifications and variations will be apparent to those skilled in the art. Furthermore, it is understood and contemplated that features specifically discussed for one infusion system embodiment may be adopted for inclusion with another infusion system embodiment, provided the functions are compatible. For example, where a fixed collar is disclosed, a spin lock collar may be used provided there is space and room for its inclusion. As another example, where a straight collar is discussed, a conically shaped collar may be incorporated to increase surface contacts with a patient's skin. Still further, where a receptacle is disclosed for coupling with an IV tubing, a male nipple may be used instead. Yet in a further example, where a catheter hub and/or a male Luer connector are described as incorporating an angular offset α, the angular offset can be omitted. Accordingly, it is to be understood that the infusion systems and their components constructed according to principles of the disclosed devices, systems, and methods may be embodied other than as specifically described herein. The disclosure is also defined in the following claims.

What is claimed is:

1. An infusion system comprising:
    a catheter hub having a catheter tube extending from a distal end of a catheter body;
    an extension set or an IV administration set having a male Luer connector for fluid communication with an open proximal end of the catheter hub; and
    a support adaptor provided with the extension set or the IV administration set and wherein the support adaptor comprises a body with a length between a first end and a second end; the body further comprising a body wall and an internal wall, wherein the body wall and the internal wall define a bore that is continuous in a radial direction relative to the length, and wherein the bore has a first opening and a second opening;
    a tubing length located in the bore and extending out the second opening, said tubing length being bendable and attached to said male Luer connector;
    wherein the bore comprises (1) a single bore path or (2) a first bore section having a first bore path and a second bore section having a second bore path, which is angled relative to the first bore path by an angle (α2), and
    wherein the internal wall defines a support surface and having at least part of the male Luer connector resting on the support surface.

2. The infusion system of claim 1, wherein the internal wall is inclined from the first end and the second end of the body.

3. The infusion system of claim 2, wherein the male Luer connector comprises a body with a male Luer tip at a first end and a tubing coupling at a second end; and a collar located around the male Luer tip.

4. The infusion system of claim 3, wherein the internal wall has an undulating surface or ridges for engaging the tubing coupling.

5. The infusion system of claim 2, wherein the internal wall comprises an entry region and an end region joined by a middle region.

6. The infusion system of claim 1, wherein the body comprises a curved upper dome wall surface and a base, and wherein a width relative to a length at the base between the first end and the second end is wider than a width at the curved upper dome wall surface.

7. The infusion system of claim 6, wherein the internal wall and the base define a wedge shaped structure.

8. The infusion system of claim 7, further comprising a void defined by an interior surface of the base and a lower surface of the internal wall.

9. The infusion system of claim 8, further comprising a void space opening formed between the base and the internal wall.

10. The infusion system of claim 1, wherein a bevel is provided at an end of the bore adjacent the second opening and defines a smaller opening at the second opening relative to the bore diameter adjacent the second opening.

11. The infusion system of claim 8, wherein the bore is bounded by a retaining lip.

12. The infusion system of claim 1, wherein the first opening defines a plane that is angled relative to a base.

13. The infusion system of claim 1, wherein the bore is approximately frustoconical and tapers in a direction extending from the first end toward the second end of the body.

14. The infusion system of claim 1, wherein the body comprises a base and wherein the support surface and the base define a wedge.

15. The infusion system of claim 1, wherein an outer surface of the body wall defines a curved upper dome wall surface.

16. The infusion system of claim 1, wherein the catheter hub comprises a valve and a valve opener located in an interior cavity of the catheter hub.

17. A method of manufacturing an infusion system comprising:
- forming a catheter hub having a catheter tube extending from a distal end of a catheter body;
- forming an extension set or an IV administration set having a tubing length and a male Luer connector for fluid communication with an open proximal end of the catheter hub, wherein said tubing length being bendable and attached to said male Luer connector; and
- mounting a support adaptor around the tubing length, wherein the support adaptor comprises a body with a length between a first end and a second end, the body further comprises a body wall and an internal wall, wherein the body wall and the internal wall define a bore that is continuous in a radial direction relative to the length, and wherein the bore has a first opening and a second opening having the tubing length located in the bore and extending out the second opening;
- wherein the bore comprises (1) a single bore path or (2) a first bore section having a first bore path and a second bore section having a second bore path, which is angled relative to the first bore path by an angle; and
- wherein the internal wall defines a support surface and having at least part of the male Luer connector resting on the support surface.

* * * * *